United States Patent
Obika et al.

(10) Patent No.: US 9,611,479 B2
(45) Date of Patent: Apr. 4, 2017

(54) CROSSLINKED NUCLEOSIDE AND NUCLEOTIDE

(71) Applicant: OSAKA UNIVERSITY, Osaka (JP)

(72) Inventors: Satoshi Obika, Osaka (JP); Takao Yamaguchi, Osaka (JP); Masahiko Horiba, Osaka (JP); Reiko Waki, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/118,546

(22) PCT Filed: Feb. 17, 2015

(86) PCT No.: PCT/JP2015/054308
§ 371 (c)(1),
(2) Date: Aug. 12, 2016

(87) PCT Pub. No.: WO2015/125783
PCT Pub. Date: Aug. 27, 2015

(65) Prior Publication Data
US 2017/0044528 A1    Feb. 16, 2017

(30) Foreign Application Priority Data
Feb. 18, 2014  (JP) .................. 2014-028210

(51) Int. Cl.
*C07H 19/06*    (2006.01)
*C07H 19/16*    (2006.01)
*C12N 15/113*   (2010.01)

(52) U.S. Cl.
CPC ........... *C12N 15/113* (2013.01); *C07H 19/06* (2013.01); *C07H 19/16* (2013.01); *C12N 2310/31* (2013.01)

(58) Field of Classification Search
None
See application file for complete search history.

(56) References Cited

U.S. PATENT DOCUMENTS

| | | |
|---|---|---|
| 5,659,022 A | 8/1997 | Kutyavin et al. |
| 6,268,490 B1 | 7/2001 | Imanishi et al. |
| 7,427,672 B2 | 9/2008 | Imanishi et al. |
| 2006/0166908 A1 | 7/2006 | Imanishi et al. |
| 2011/0053881 A1 | 3/2011 | Seth et al. |
| 2014/0112887 A1* | 4/2014 | Mayes ............... C07H 19/20 424/85.7 |

FOREIGN PATENT DOCUMENTS

| | | |
|---|---|---|
| WO | 9419023 | 9/1994 |
| WO | 2004044137 | 5/2004 |
| WO | WO2009/006478 | * 1/2009 |

OTHER PUBLICATIONS

Satoshi Obika, "Soyaku Seeds to shite Kitai sereru Kakusan lyakuhin-sono Tenbo to Kadai-2. Tobu Kakyogata Kakusan no lyaku eno Oyo", Medicine and Drug Journal 2012, vol. 48, pp. 65 to 69.
PCT/JP2015/054308; PCT International Search Report of the International Searching Authority dated May 11, 2015 and its English translation.
C. Wahlestedt et al., Proc. Natl. Acad. Sci. USA, 2000, vol. 97, No. 10, pp. 5633-5638.
Y. Hari et al., Bioorg. Med. Chem., 2006, vol. 14, pp. 1029-1038.
K. Miyashita et al., Chem. Commun., 2007, pp. 3765-3767.
S.M.A. Rahman et al., J. Am. Chem. Soc., 2008, vol. 130, No. 14, pp. 4886-4896.
M. Kuwahara et al., Nucleic Acids Res., 2008, vol. 36, No. 13, pp. 4257-4265.
S. Obika et al., Bioorg. Med. Chem., 2001, vol. 9, pp. 1001-1011.
Partial English translation for Satoshi Obika, "Soyaku Seeds to shite Kitai sareru Kakusan lyakuhin-sono Tenbo to Kadai-2. Tobu Kakyogata Kakusan no lyaku eno Oyo", Medicine and Drug Journal 2012, vol. 48, pp. 65 to 69 (Previously Submitted).
Seth et al, J. Org. Chem., 2010, 75, pp. 1569-1581.

* cited by examiner

*Primary Examiner* — Traviss C McIntosh, III
(74) *Attorney, Agent, or Firm* — Renner, Otto, Boisselle & Sklar, LLP

(57) ABSTRACT

Disclosed are bridged nucleosides and nucleotides. The nucleosides of the present invention have a 2',4'-bridged structure and are represented by formula I below:

[Chemical 1]

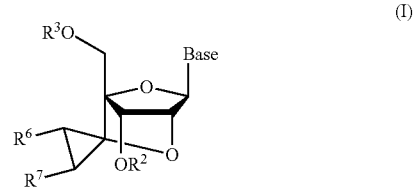

An oligonucleotide containing a 2',4'-bridged artificial nucleotide of the present invention has a binding affinity for single-stranded RNA comparable to that of known 2',4'-BNA/LNA and higher nuclease resistance than LNA. In particular, since the oligonucleotide has a much higher binding affinity for single-stranded RNA than S-oligo, it is expected that the oligonucleotide is applicable to nucleic acid drugs.

11 Claims, 3 Drawing Sheets

*P<0.00001, **P<0.05

CROSSLINKED NUCLEOSIDE AND NUCLEOTIDE

The present application is a U.S. National Stage Application under 35 USC §371 of International Application No. PCT/JP2015/054308, filed 17 Feb. 2015, published as WO 2015/125783 A1 on Aug. 27, 2015, which in turn claims priority to Japanese Application No. 2014-028210, filed 18 Feb. 2014, the entirety of both of which are incorporated herein by reference.

TECHNICAL FIELD

The present invention relates to bridged nucleosides and nucleotides. More specifically, the present invention relates to bridged nucleosides and nucleotides having high binding affinities for single-stranded RNAs and high nuclease resistance.

BACKGROUND ART

Treatments of disorders using nucleic acid drugs include antisense therapies, antigene therapies, aptamers, siRNAs, and the like. An antisense therapy is the procedure for treatment or prevention of diseases involving inhibiting a translation process of pathogenic RNAs by externally introducing oligonucleotides (antisense strands) complementary to disease-associated mRNAs to form the double strands. The mechanism of siRNAs is similar to that of the antisense therapies, which involves inhibiting translation from mRNAs to proteins by administration of double-stranded RNAs to the body. Meanwhile, in the antigene therapies, transcription of DNA to RNA is suppressed by externally introducing triple-strand-forming oligonucleotides corresponding to the DNA sites transcribed into the pathogenic RNA. Aptamers, which are small nucleic acid molecules (oligonucleotides), exert their functions by binding to disease-related biological components, such as proteins.

Although various artificial nucleic acids have been developed as materials for such nucleic acid drugs, there has not been found any ideal molecule yet. For example, the materials developed for nucleic acid drugs to date include S-oligo (phosphorothioate), 2',4'-BNA (bridged nucleic acid)/LNA (locked nucleic acid) (See Patent Documents 1 to 3 and Non-patent Documents 1 to 4). S-oligo is commercially available as an antisense drug for cytomegalovirus in United States. While this drug has high nuclease resistance, it has a weakness to be improved concerning about its low binding affinity for the target nucleic acid strands. All types of 2',4'-BNA/LNA which have ever been developed have high binding affinities for their target nucleic acid strands and they are the most promising molecules as the materials for the future nucleic acid drugs. However, they still remain to be improved with regard to their nuclease resistance which is not enough to be stable in vivo.

Furthermore, in recent years, application of oligonucleotides having nucleoside structures such as those represented by formulas a and b below:

[Chemical 1]

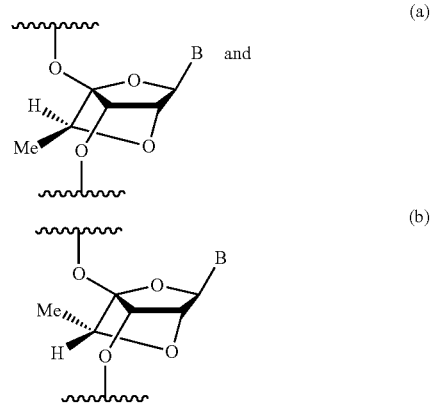

to the aforementioned materials has also been proposed (Patent Document 4).

However, extremely complicated processes are required for production of nucleosides themselves serving as a basis for structures such as those represented by the formulas a and b above. For this reason, development of oligonucleotides having equivalent or superior performance to such oligonucleotides and also having much higher industrial production efficiency is demanded.

CITATION LIST

Patent Documents

[Patent Document 1] WO98/39352
[Patent Document 2] WO2005/021570
[Patent Document 3] WO2003/068795
[Patent Document 4] WO2009/006478

Non Patent Documents

[Non-Patent Document 1] C. Wahlestedt et al., Proc. Natl. Acad. Sci. USA, 2000, Vol. 97, No. 10, pp. 5633-5638
[Non-Patent Document 2] Y. Hari et al., Bioorg. Med. Chem., 2006, Vol. 14, pp. 1029-1038
[Non-Patent Document 3] K. Miyashita et al., Chem. Commun., 2007, pp. 3765-3767
[Non-Patent Document 4] S. M. A. Rahman et al., J. Am. Chem. Soc., 2008, Vol. 130, No. 14, pp. 4886-4896
[Non-Patent Document 5] M. Kuwahara et al., Nucleic Acids Res., 2008, Vol. 36, No. 13, pp. 4257-4265
[Non-Patent Document 6] S. Obika et al., Bioorg. Med. Chem., 2001, Vol. 9, pp. 1001-1011

SUMMARY OF THE INVENTION

Problem to be Solved by the Invention

The present invention was made to address the above-described problems, and it is an object thereof to provide a novel molecule for antisense therapies and nucleic acid drugs, the molecule being not susceptible to nuclease degradation in vivo, having a high binding affinity and specificity for target mRNAs, being capable of effectively regulating expression of specific genes, and furthermore, being superior in terms of productivity.

Means for Solving the Problem

The present invention provides a compound represented by formula I below or a salt thereof:

[Chemical 2]

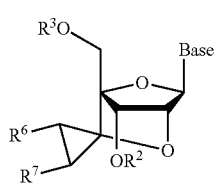

(I)

wherein Base represents a purine-9-yl group or a 2-oxo-1,2-dihydropyrimidine-1-yl group that may have any one or more substituents selected from group α, where the group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio group, an amino group, a $C_1$ to $C_6$ linear alkylamino group, an amino group protected by a protective group for nucleic acid synthesis, and a halogen atom;

$R^2$ and $R^3$ each independently represent a hydrogen atom, a protective group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the group α and that may contain a hetero atom, an aralkyl group having a $C_3$ to $C_{12}$ aryl moiety that may have any one or more substituents selected from the group α and that may contain a hetero atom, an acyl group that may have any one or more substituents selected from the group α, a silyl group that may have any one or more substituents selected from the group α, a phosphate group that may have any one or more substituents selected from the group α, a phosphate group protected by a protective group for nucleic acid synthesis, or —P($R^4$)$R^5$ (where $R^4$ and $R^5$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group); and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$— (where n is an integer from 2 to 5).

In one embodiments, the Base in the formula I is a 6-aminopurine-9-yl group, a 2,6-diaminopurine-9-yl group, a 2-amino-6-chloropurine-9-yl group, a 2-amino-6-fluoropurine-9-yl group, a 2-amino-6-bromopurine-9-yl group, a 2-amino-6-hydroxypurine-9-yl group, a 6-amino-2-methoxypurine-9-yl group, a 6-amino-2-chloropurine-9-yl group, a 6-amino-2-fluoropurine-9-yl group, a 2,6-dimethoxypurine-9-yl group, a 2,6-dichloropurine-9-yl group, a 6 mercaptopurine-9-yl group, a 2-oxo-4-amino-1,2-dihydropyrimidine-1-yl group, a 4-amino-2-oxo-5-fluoro-1,2-dihydropyrimidine-1-yl group, a 4-amino-2-oxo-5-chloro-1,2-dihydropyrimidine-1-yl group, a 2-oxo-4-methoxy-1,2-dihydropyrimidine-1-yl group, a 2-oxo-4 mercapto-1,2-dihydropyrimidine-1-yl group, a 2-oxo-4-hydroxy-1,2-dihydropyrimidine-1-yl group, a 2-oxo-4-hydroxy-5-methyl-1,2-dihydropyrimidine-1-yl group, or a 4-amino-5-methyl-2-oxo-1,2-dihydropyrimidine-1-yl group.

In one embodiments, the Base in the formula I is a 2-oxo-4-hydroxy-5-methyl-1,2-dihydropyrimidine-1-yl group.

In one embodiments, $R^6$ and $R^7$ in the formula I are both hydrogen atoms.

The present invention also provides an oligonucleotide containing at least one nucleoside structure represented by formula II below or a pharmacologically acceptable salt thereof:

[Chemical 3]

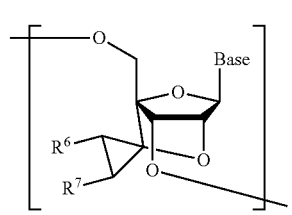

(II)

wherein Base represents a purine-9-yl group or a 2-oxo-1,2-dihydropyrimidine-1-yl group that may have any one or more substituents selected from group α, wherein the group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio groups, an amino group, a $C_1$ to $C_6$ linear alkylamino group, an amino group protected by a protective group for nucleic acid synthesis, and a halogen atom; and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$— (where n is an integer from 2 to 5).

In one embodiment, $R^6$ and $R^7$ in the formula II are both hydrogen atoms.

The present invention also provides a method for producing the oligonucleotide or pharmacologically acceptable salt thereof described above, comprising:

synthesizing an oligonucleotide using a compound represented by formula I below or a pharmacologically acceptable salt thereof:

[Chemical 4]

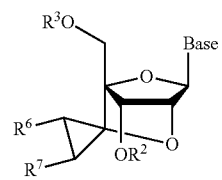

(I)

wherein Base represents a purine-9-yl group or a 2-oxo-1,2-dihydropyrimidine-1-yl group that may have any one or more substituents selected from group α, wherein group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio group, an amino group, a $C_1$ to $C_6$ linear alkylamino group, an amino group protected by a protective group for nucleic acid synthesis, and a halogen atom;

$R^2$ and $R^3$ each independently represent a hydrogen atom, a protective group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the group α and that may contain a hetero atom, an aralkyl group having a $C_3$ to $C_{12}$ aryl moiety that may have any one or more substituents selected from the group α and that may contain a hetero atom, an acyl group that may have any one or more substituents selected from the group α, a silyl group that may have any one or more substituents selected from the group α, a phosphate group that may have any one or more substituents selected from the group α, a phosphate group protected by a protective group for nucleic acid synthesis, or —P($R^4$)$R^5$ (where $R^4$ and $R^5$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group); and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —(CH$_2$)$_n$— (where n is an integer from 2 to 5).

Effects of the Invention

According to the present invention, novel 2',4'-bridged nucleosides and nucleotides are provided. An oligonucleotide containing a 2',4'-bridged artificial nucleotide of the present invention has a binding affinity for single-stranded RNA comparable to that of known 2',4'-BNA/LNA and has higher nuclease resistance than LNA. In particular, they are expected to the application for nucleic acid drugs because of their much stronger binding affinity for single-stranded RNAs than S-oligo's affinity. Moreover, the 2',4'-bridged nucleosides and nucleotides of the present invention can be produced by simpler reaction processes than conventional ones, and thus it is also possible to increase industrial production efficiency even more.

MODES FOR CARRYING OUT THE INVENTION

Figure 1:
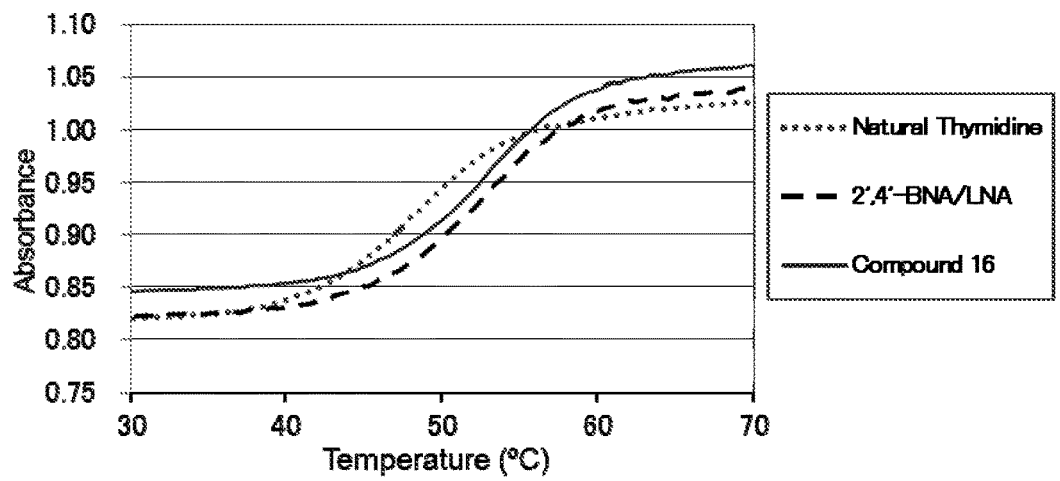
FIG. 1 is a graph illustrating $T_m$ curves indicating dissociation of double-stranded hybrids which various types of oligonucleotides having the sequence of 5'-d(GCGTTXTTTGCT)-3' have formed with a single-stranded oligoRNA target strand.

The following definitions shall apply throughout the specification.

The term "$C_1$ to $C_6$ linear alkyl group", as used herein, refers to any linear alkyl group having 1 to 6 carbon atoms and specifically a methyl group, an ethyl group, an n-propyl group, an n-butyl group, an n-pentyl group, or an n-hexyl group.

The term "$C_1$ to $C_6$ linear alkoxy group", as used herein, encompasses alkoxy groups having any linear alkyl group having 1 to 6 carbon atoms. The linear alkoxy groups include a methyloxy group, an ethyloxy group, an n-propyloxy group, and the like.

The term "$C_1$ to $C_6$ linear alkylthio group", as used herein, encompasses alkylthio groups having any linear alkyl group having 1 to 6 carbon atoms. The linear alkylthio groups include a methylthio group, an ethylthio group, an n-propylthio group, and the like.

The term "$C_1$ to $C_6$ linear alkylamino group", as used herein, encompasses alkylamino groups which contain one or two alkylamino groups having any linear alkyl group having 1 to 6 carbon atoms. The linear alkylamino groups include a methylamino group, a dimethylamino group, an ethylamino group, a methylethylamino group, a diethylamino group, and the like.

The term "$C_1$ to $C_7$ alkyl group that may be branched or form a ring", as used herein, encompasses any linear alkyl groups having 1 to 7 carbon atoms, any branched alkyl groups having 3 to 7 carbon atoms, and any cyclic alkyl groups having 3 to 7 carbon atoms. It may be simply referred to as "lower alkyl group". For example, the linear alkyl groups having 1 to 7 carbon atoms include a methyl group, an ethyl group, an n-propyl group, an n-butyl group, an n-pentyl group, an n-hexyl group, and an n-heptyl group, the branched alkyl groups having 3 to 7 carbon atoms include an isopropyl group, an isobutyl group, a tert-butyl group, an isopentyl group, and the like, and the cyclic alkyl groups having 3 to 7 carbon atoms include a cyclobutyl group, a cyclopentyl group, a cyclohexyl group, and the like.

The term "$C_2$ to $C_7$ alkenyl group that maybe branched or form a ring", as used herein, encompasses any linear alkenyl groups having 2 to 7 carbon atoms, any branched alkenyl groups having 3 to 7 carbon atoms, and any cyclic alkenyl groups having 3 to 7 carbon atoms. It may be simply referred to as "lower alkenyl group". For example, the linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, a 1-hexenyl group, and the like, the branched alkenyl groups having 3 to 7 carbon atoms include an isopropenyl group, a 1-methyl-1-prop enyl group, a 1-methyl-2-propenyl group, a 2-methyl- 1-propenyl group, a 2-methyl-2-propenyl group, a 1-methyl-2-butenyl group, and the like, and the cyclic alkenyl groups having 3 to 7 carbon atoms include a cyclobutenyl group, a cyclopentenyl group, a cyclohexenyl group, and the like.

The term "$C_3$ to $C_{10}$ aryl group that may contain a hetero atom", as used herein, encompasses any aryl groups having 6 to 10 carbon atoms and consisting of only hydrocarbons and any heteroaryl groups having 3 to 12 carbon atoms in which at least one carbon atom constituting the ring structure of the aryl groups was substituted with a hetero atom (e.g., a nitrogen atom, an oxygen atom, and a sulfur atom as well as a combination of these). The aryl groups having 6 to 10 carbon atoms include a phenyl group, a naphthyl group, an indenyl group, an azulenyl group, and the like, and the heteroaryl groups having 3 to 12 carbon atoms include a pyridyl group, a pyrrolyl group, a quinolyl group, an indolyl group, an imidazolyl group, a furyl group, a thienyl group, and the like.

Examples of the term "aralkyl group having a $C_3$ to $C_{12}$ aryl moiety that may contain a hetero atom", as used herein, include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, a 3-thienylpropyl group, and the like.

Examples of the term "acyl group", as used herein, include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group and a heneicosanoyl group; carboxylated alkylcarbonyl groups such as a succinoyl group, a glutaroyl group, and an adipoyl group; halogeno lower alkylcarbonyl groups such as a chloroacetyl group, a dichloroacetyl group, a trichloroacetyl group, and a trifluoroacetyl group; lower alkoxy lower alkylcarbonyl groups such as a methoxyacetyl group; and unsaturated alkylcarbonyl groups such as a (E)-2-methyl-2-butenoyl group. Examples of the aromatic acyl groups include arylcarbonyl groups such as a benzoyl group, an α-naphthoyl group, and a β-naphthoyl group; halogenoarylcarbonyl groups such as a 2-bromobenzoyl group and a 4-chlorobenzoyl group; lower alkylated arylcarbonyl groups such as a 2,4,6-trimethylbenzoyl group and a 4-toluoyl group; lower alkoxylated arylcarbonyl groups such as a 4-anisoyl group; carboxylated arylcarbonyl groups such as a 2-carboxybenzoyl group, 3-carboxybenzoyl group, and a 4-carboxybenzoyl group; nitrated arylcarbonyl groups such as a 4-nitrobenzoyl group and a 2-nitrobenzoyl group; lower alkoxycarbonylated arylcarbonyl groups such as a 2-(methoxycarbonyl)benzoyl group; and arylated arylcarbonyl groups such as a 4-phenylbenzoyl group. Preferably the acyl group is a formyl group, an acetyl group, a propionyl group, a butyryl group, an isobutyryl group, a pentanoyl group, a pivaloyl group, or a benzoyl group.

Examples of the term "silyl group", as used herein, include tri-lower alkylsilyl groups such as a trimethylsilyl group, a triethylsilyl group, an isopropyldimethylsilyl group, a t-butyldimethylsilyl group, a methyldiisopropylsilyl group, a methyl di-t-butylsilyl group, and a triisopropylsilyl group; and tri-lower alkylsilyl groups substituted with one or two aryl groups such as a diphenylmethylsilyl group, a butyldiphenylbutylsilyl group, a diphenylisopropylsilyl group, and a phenyldiisopropylsilyl group. Preferably the silyl group is a trimethylsilyl group, a triethylsilyl group, a triisopropylsilyl group, a t-butyldimethylsilyl group, or a t-butyldiphenylsilyl group, more preferably a trimethylsilyl group.

The term "halogen atom", as used herein, includes, for example, a fluorine atom, a chlorine atom, a bromine atom, and an iodine atom. Preferably, the halogen atom is a fluorine atom or a chlorine atom.

The term "protective group" in phrases "a protective group for an amino group on nucleic acid synthesis", "a protective group for a hydroxyl group on nucleic acid synthesis", "a hydroxyl group protected by a protective group for nucleic acid synthesis", "a phosphate group protected by a protective group for nucleic acid synthesis", and "a mercapto group protected by a protective group for nucleic acid synthesis", as used herein, is not limited to specific groups as far as the protective group can stably protect an amino group, a hydroxyl group, a phosphate group, or a mercapto group during nucleic acid synthesis. Specifically, the protective group refers to those which are stable in acid or neutral condition and may be cleaved by chemical methods such as hydrogenolysis, hydrolysis, electrolysis, and photodissociation. Examples of such protective groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower alkoxymethyl groups, lower alkoxylated lower alkoxymethyl groups, halogeno lower alkoxymethyl groups, lower alkoxylated ethyl groups, halogenated ethyl groups, methyl groups substituted with one to three aryl groups, "methyl groups substituted with one to three aryl groups having the aryl ring substituted with a lower alkyl group, a lower alkoxy group, a halogen atom, or a cyano group", lower alkoxycarbonyl groups, "aryl groups substituted with a halogen atom, a lower alkoxy group, or a nitro group", "lower alkoxycarbonyl groups substituted with a halogen atom or a tri-lower alkylsilyl group", alkenyloxycarbonyl groups, "aralkyloxycarbonyl groups having aryl rings that may be substituted with a lower alkoxy or a nitro group", and the like.

More specifically, the tetrahydropyranyl groups or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, a 4-methoxytetrahydrothiopyran-4-yl group, and the like. The tetrahydrofuranyl groups or tetrahydrothiofuranyl groups include a tetrahydrofuran-2-yl group and a tetrahydrothiofuran-2-yl group. The lower alkoxymethyl groups include a methoxymethyl group, a 1,1-dimethyl-1-methoxymethyl group, an ethoxymethyl group, a propoxymethyl group, an isopropoxymethyl group, a butoxymethyl group, a t-butoxymethyl group, and the like. The lower alkoxylated lower alkoxymethyl groups include a 2-methoxyethoxymethyl group and the like. The halogeno lower alkoxymethyl groups include a 2,2,2-trichloroethoxymethyl group, a bis(2-chloroethoxy)methyl group, and the like. The lower alkoxylated ethyl groups include a 1-ethoxyethyl group, a 1-(isopropoxy) ethyl group, and the like. The halogenated ethyl groups include a 2,2,2-trichloroethyl group and the like. The methyl groups substituted with one to three aryl groups include a benzyl group, an α-naphthylmethyl group, a β-naphthylmethyl group, a diphenylmethyl group, a triphenylmethyl group, an α-naphthyldiphenylmethyl group, a 9-anthrylmethyl group, and the like. The "methyl groups substituted with one to three aryl groups having aryl rings substituted with a lower alkyl group, a lower alkoxy group, a halogen atom, or a cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, a 4-cyanobenzyl group, and the like. The lower alkoxycarbonyl groups include a methoxycarbonyl group, an ethoxycarbonyl group, a t-butoxycarbonyl group, an isobutoxycarbonyl group, and the like. The "aryl groups substituted with a halogen atom, a lower alkoxy group, or a nitro group" include a 4-chlorophenyl group, a 2-fluorophenyl group, a 4-methoxyphenyl group, a 4-nitrophenyl group, a 2,4-dinitrophenyl group, and the like. The "lower alkoxycarbonyl groups substituted with a halogen atom or a tri-lower alkylsilyl group" include a 2,2,2-trichloroethoxycarbonyl group, a 2-trimethylsilyl ethoxycarbonyl group, and the like. The alkenyloxycarbonyl groups include a vinyloxycarbonyl group, an aryloxycarbonyl group, and the like. The "aralkyloxycarbonyl groups having an aryl ring that may be substituted with a lower alkoxy or a nitro group" include a benzyloxycarbonyl group, a 4-methoxybenzyloxycarbonyl group, a 3,4-dimethoxybenzyloxycarbonyl group, a 2-nitrobenzyloxycarbonyl group, a 4-nitrobenzyloxycarbonyl group, and the like.

The "protective group for an hydroxyl group on nucleic acid synthesis" is preferably an aliphatic acyl group, an aromatic acyl group, a methyl group substituted with one to three aryl groups, a "methyl group substituted with one to three aryl groups having aryl rings substituted with a lower alkyl, a lower alkoxy, a halogen, or a cyano group", or a silyl group, and more preferably an acetyl group, a benzoyl group, a benzyl group, a p-methoxybenzoyl group, a dimethoxytrityl group, a monomethoxytrityl group, or a tert-butyldiphenylsilyl group. The protective group in the phrase "a hydroxyl group protected by a protective group for nucleic acid synthesis" is preferably an aliphatic acyl group, an aromatic acyl group, "a methyl group substituted with one to three aryl groups", "an aryl group substituted with a halogen atom, lower alkoxy group, or a nitro group", a lower alkyl group, or a lower alkenyl group, and more preferably a benzoyl group, a benzyl group, a 2-chlorophenyl group, a 4-chlorophenyl group, or a 2-propenyl group. The "protective group for an amino group on nucleic acid synthesis" is preferably an acyl group, and more preferably a benzoyl group. The "protective group" in the phrase "a phosphate group protected by a protective group for nucleic acid synthesis" is preferably a lower alkyl group, a lower alkyl group substituted with a cyano group, an aralkyl group, "an aralkyl group having an aryl ring substituted with a nitro group or a halogen atom", or "an aryl group substituted with a lower alkyl group, a halogen atom, or a nitro group", and more preferably a 2-cyanoethyl group, a 2,2,2-trichloroethyl group, a benzyl group, a 2-chlorophenyl group, or a 4-chlorophenyl group. The "protective group" in the phrase "a mercapto group protected by a protective group for nucleic acid synthesis" is preferably an aliphatic acyl group or an aromatic acyl group, and more preferably a benzoyl group.

Herein, among the groups represented by —P(R$^4$)R$^5$ (where R$^4$ and R$^5$ each independently represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 6 carbon atoms), the ones where R$^4$ can be represented by OR$^{4a}$ and R$^5$ can be represented by NR$^{5a}$ are referred to as a "phosphoramidite group". The phosphoramidite groups include, preferably, groups represented by the formula —P(OC$_2$H$_4$CN)(N(iPr)$_2$) or the formula —P(OCH$_3$)(N(iPr)$_2$). In these formulas, iPr represents an isopropyl group.

The terms "nucleoside" and "nucleoside analogue", as used herein, refer to an unnatural "nucleoside" in which a purine or a pyrimidine base is bonded to sugar, as well as those in which a heteroaromatic ring and an aromatic hydrocarbon ring other than purine and pyrimidine, serving to substitute for a purine or a pyrimidine base, are bonded with sugars.

The terms "artificial oligonucleotide" and "oligonucleotide analogue", as used herein, refer to unnatural derivatives of "oligonucleotides" in which 2 to 50 of same or different "nucleosides" or "nucleoside analogues" are bonded via phosphodiester bonds. Such analogues include preferably sugar derivatives with sugar moieties modified; thioated derivatives with phosphate diester moiety thioated; esters with terminal phosphate moiety esterificated; and amides in which amino groups on a purine base is amidated, and preferably sugar derivatives with sugar moiety modified.

The term "salt thereof", as used herein, refers to salts of compounds represented by the formula I or II according to the present invention. Examples of these salts include metal salts including alkaline metal salts such as sodium salts, potassium salts, and lithium salts, alkaline earth metal salts such as calcium salts and magnesium salts, aluminum salts, iron salts, zinc salts, cuprous salts, nickel salts, and cobalt salts; amine salts including inorganic salts such as ammonium salts and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and Tris (hydroxymethyl)aminomethane salts; inorganic acid salts such as halide acid salts (for example hydrofluoride, hydrochloride, hydrobromide and hydriodide), nitrate, perchlorate, sulfate, and phosphate; organic acid salts including lower alkanesulfonates such as methanesulfonates, trifluoromethanesulfonates and ethanesulfonates, arylsulfonates such as benzenesulfonates and p-toluenesulfonates, acetates, malates, fumarates, succinates, citrates, tartrates, oxalates, and maleates; and amino acid salts such as glycine salts, lysine salts, arginine salts, ornithine salts, glutamates, and aspartates.

The term "pharmacologically acceptable salt thereof", as used herein, refers to salts of oligonucleotide analogues containing at least one of nucleoside structures represented by the formula II of the present invention. Examples of these salts include metal salts including alkaline metal salts such as sodium salts, potassium salts, and lithium salts, alkaline earth metal salts such as calcium salts and magnesium salts, aluminum salts, iron salts, zinc salts, cuprous salts, nickel salts, and cobalt salts; amine salts including inorganic salts such as ammonium salts and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and Tris(hydroxymethyl)aminomethane salts; inorganic acid salts such as halide acid salts (for example hydrofluoride, hydrochloride, hydrobromide, hydriodide), nitrates, perchlorates, sulfates, and phosphates; organic acid salts including lower alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates, and maleates; and amino acid salts such as glycine salts, lysine salts, arginine salts, ornithine salts, glutamates, and aspartates.

The present invention is described in more detail below.

2',4'-bridged nucleosides and nucleotides or salts (preferably, pharmacologically acceptable salts) thereof according to the present invention (hereinafter, the term "2',4'-bridged nucleosides" collectively refers to 2',4'-bridged nucleosides themselves, salts of 2',4'-bridged nucleosides, and pharmacologically acceptable salts of 2',4'-bridged nucleosides, unless otherwise stated) have the structures represented by formula I below:

[Chemical 5]

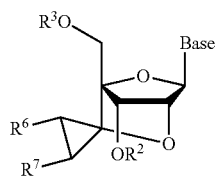
(I)

where "Base" represents a purine-9-yl group or a 2-oxo-1,2-dihydropyrimidine-1-yl group that may have any one or more substituents selected from group α, where the group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio group, an amino group, a $C_1$ to $C_6$ linear alkylamino group, an amino group protected by a protective group for nucleic acid synthesis, and a halogen atom;

$R^2$ and $R^3$ each independently represent a hydrogen atom, a protective group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the group α and that may contain a hetero atom (preferably, a $C_3$ to $C_9$ aryl group that may have any one or more substituents selected from the group α that may contain a hetero atom), an aralkyl group having a $C_3$ to $C_{12}$ aryl moiety that may have any one or more substituents selected from the group α and that may contain a hetero atom, an acyl group that may have any one or more substituents selected from the group α, a silyl group that may have any one or more substituents selected from the group α, a phosphate group that may have any one or more substituents selected from the group α, a phosphate group protected by a protective group for nucleic acid synthesis, or —P($R^4$)$R^5$ (where $R^4$ and $R^5$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group); and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$— (where n is an integer from 2 to 5).

In the formula I described above, "Base" is a purine base (i.e., purine-9-yl group) or a pyrimidine base (i.e., 2-oxo-1,2-dihydropyrimidine-1-yl group). These bases may have any one or more substituents selected from group α consisting of a hydroxyl group, a $C_1$ to $C_6$ linear alkyl group, a $C_1$ to $C_6$ linear alkoxy group, a mercapto group, a $C_1$ to $C_6$ linear alkylthio group, an amino group, a $C_1$ to $C_6$ linear alkylamino group, and a halogen atom.

Specific examples of "Base" described above include a 6-aminopurine-9-yl group (adeninyl group), a 2,6-diaminopurine-9-yl group, a 2-amino-6-chloropurine-9-yl group, a 2-amino-6-fluoropurine-9-yl group, a 2-amino-6-bromopurine-9-yl group, a 2-amino-6-hydroxypurine-9-yl group (guaninyl group), a 2-amino-6-methoxypurine-9-yl group, a 6-amino-2-chloropurine-9-yl group, a 6-amino-2-fluoropurine-9-yl group, a 2,6-dimethoxypurine-9-yl group, a 2,6-dichloropurine-9-yl group, a 6 mercaptopurine-9-yl group, a 2-oxo-4-amino-1,2-dihydropyrimidine-1-yl group (cytosinyl group), a 4-amino-2-oxo-5-fluoro-1,2-dihydropyrimidine-1-yl group, a 4-amino-2-oxo-5-chloro-1,2-dihydropyrimidine-1-yl group, a 2-oxo-4-methoxy-1,2-dihydropyrimidine-1-yl group, a 2-oxo-4 mercapto-1,2-dihydropyrimidine-1-yl group, a 2-oxo-4-hydroxy-1,2-dihydropyrimidine-1-yl group (uracilyl group), a 2-oxo-4-hydroxy-5-methyl-1,2-dihydropyrimidine-1-yl group (thyminyl group), and a 4-amino-5-methyl-2-oxo-1,2-dihydropyrimidine-1-yl group.

Among them, considering the introduction into nucleic acid drugs, "Base" is preferably one of compounds which have the structural formulas represented as follows:

[Chemical 6]

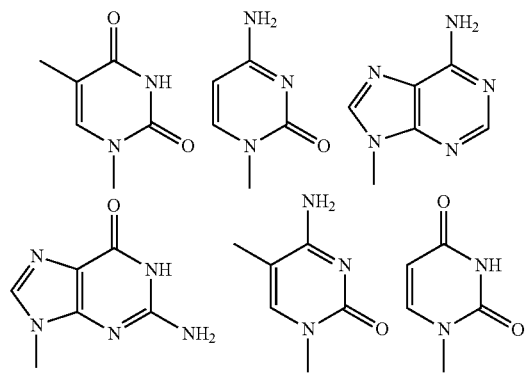

such as a 2-oxo-4-hydroxy-5-methyl-1,2-dihydropyrimidine-1-yl group (thyminyl group), a 2-oxo-4-amino-1,2-dihydropyrimidine-1-yl group (cytosinyl group), a 6-aminopurine-9-yl group (adeninyl group), a 2-amino-6-hydroxypurine-9-yl group (guaninyl group), a 4-amino-5-methyl-2-oxo-1,2-dihydropyrimidine-1-yl group, or a 2-oxo-4-hydroxy-1,2-dihydropyrimidine-1-yl group (uracilyl group), and more particularly a 2-oxo-4-hydroxy-5-methyl-1,2-dihydropyrimidine-1-yl group (thyminyl group). During the synthesis of the oligonucleotides, a hydroxyl group is preferably protected by a protective group.

Furthermore, in the formula I above, an example of the combination of $R^6$ and $R^7$ is the case where both of $R^6$ and $R^7$ are hydrogen atoms. Other examples of the combination of $R^6$ and $R^7$ include combinations which can be created in accordance with the type of a linear or branched Grignard reagent to be used in the Kulinkovich reaction and the type of an alkene to be added and with which the formula I can be represented as formulas below:

[Chemical 7]

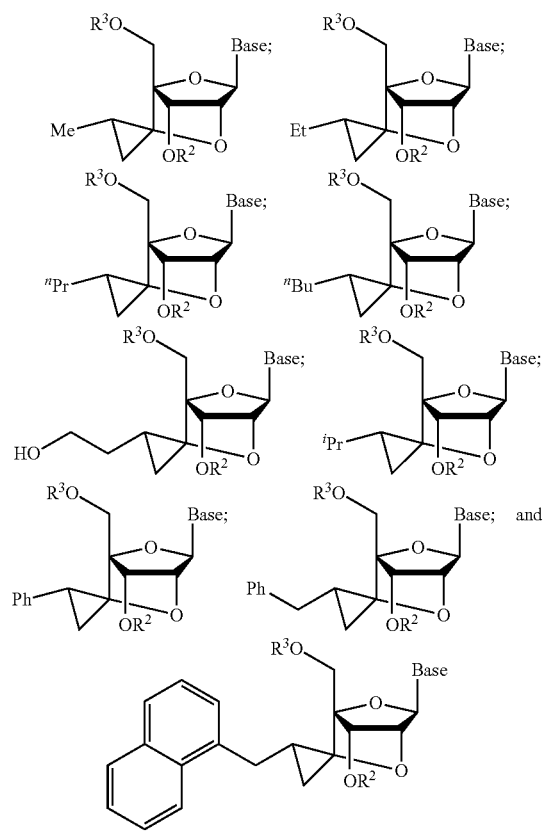

and

[Chemical 8]

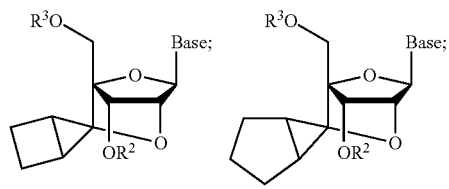

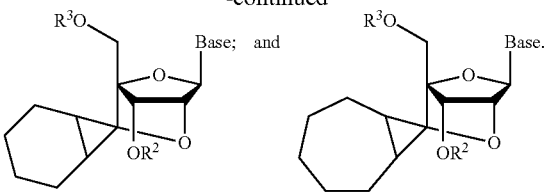

for example.

The 2',4'-bridged nucleosides of the present invention have, for example, a spirocyclopropane group introduced into the position 6' in the bridged structure of conventional 2',4'-BNA/LNA, and thus improve the enzyme-resistance of oligonucleotides, which will be described later. Moreover, a distortion of the ring of such a cyclopropane group has a direct effect on the conformation of the sugar moiety. Thus, the 2',4'-bridged nucleosides of the present invention can further improve the binding affinity of the resultant oligonucleotide for ssRNA due to this effect. Furthermore, during the synthesis of the 2',4'-bridged nucleosides of the present invention, a known reaction (Kulinkovich reaction) can be easily used for introduction of the spirocyclopropane group into the position 6' in the bridged structure. This holds true for 2',4'-bridged nucleoside of the present invention with the spirocyclopropane group at least partially substituted. Thus, 2',4'-bridged nucleosides of the present invention can be even more efficiently synthesized than conventional 2',4'-BNA/LNA having other substituents such as a methyl group, a methoxymethyl group, or the like introduced into the position 6'.

In the present invention, oligonucleotides (2',4'-bridged artificial nucleotides) may be prepared using such 2',4'-bridged nucleosides. For example, triphosphorylation may be easily carried out according to the method described in Non-patent Document 5.

The oligonucleotides or pharmacologically acceptable salts thereof of the present invention contain at least one nucleoside structure represented by formula II below:

[Chemical 9]

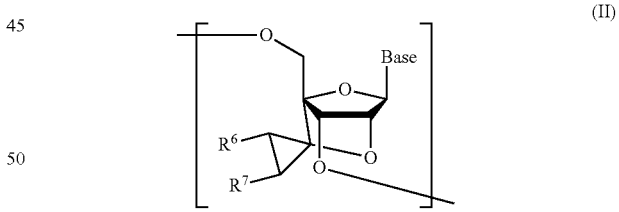

(where "Base", $R^6$ and $R^7$ are as defined for the formula I above).

The oligonucleotides of the present invention have at least one of the nucleoside structures above at any positions in the structures. The position and number of the nucleoside structures, which are not limited to the specific position and number, may be appropriately selected depending on the purposes.

An oligonucleotide analogue (antisense molecule) containing such a nucleoside structure has significantly improved enzyme-resistance when compared with the cases where conventional 2',4'-BNA/LNA is used, and also has a good binding affinity for ssRNA comparable to that of known 2',4'-BNA/LNA.

With all these facts, the oligonucleotide analogues synthesized using the 2',4'-bridged nucleosides of the present invention are expected their usefulness as pharmaceutical agents (antisense molecules) inhibiting a function of a specific gene to treat a disease, such as antitumor agents and antiviral drugs.

In particular, for antisense therapies, both of a binding affinity for complementary sense strand RNAs and a resistance to in vivo DNA-degrading enzymes are required. Generally, a nucleic acid in the form of a single strand is known to constantly have a structural fluctuation of a sugar moiety between the form close to a sugar moiety in a double-stranded DNA and the form close to a sugar moiety in a double-stranded DNA-RNA or a double-stranded RNA. When a single-stranded nucleic acid forms a double strand with the complementary RNA strand, its structure of the sugar moiety is fixed. Therefore, the 2',4'-bridged nucleosides of the present invention form readily double strands with the intended RNA strands, which may be then maintained stably, because the sugar moiety has been already kept to the structure capable of forming double strands. Furthermore, a double-stranded nucleic acid is known to be stabilized with hydrated water with a chain-like structure referred to as "network of water molecules".

Additives typically used in the art of pharmaceuticals such as excipients, binders, preservatives, oxidation stabilizers, disintegrants, lubricants, and flavoring substances can be added to the oligonucleotide analogues of the present invention to prepare parenteral formulations or liposomal formulations. Also, for example, topical formulations such as liquids, creams, and ointments may be prepared by adding pharmaceutical carriers typically used in the art.

EXAMPLES

Hereinafter, the present invention will be more specifically described using examples; however, the present invention is not limited to these examples.

Example 1

Synthesis of 2',4'-Bridged Nucleoside (1): Synthesis of Spirocyclopropane BNA-T (scpBNA-T) Amidite Block

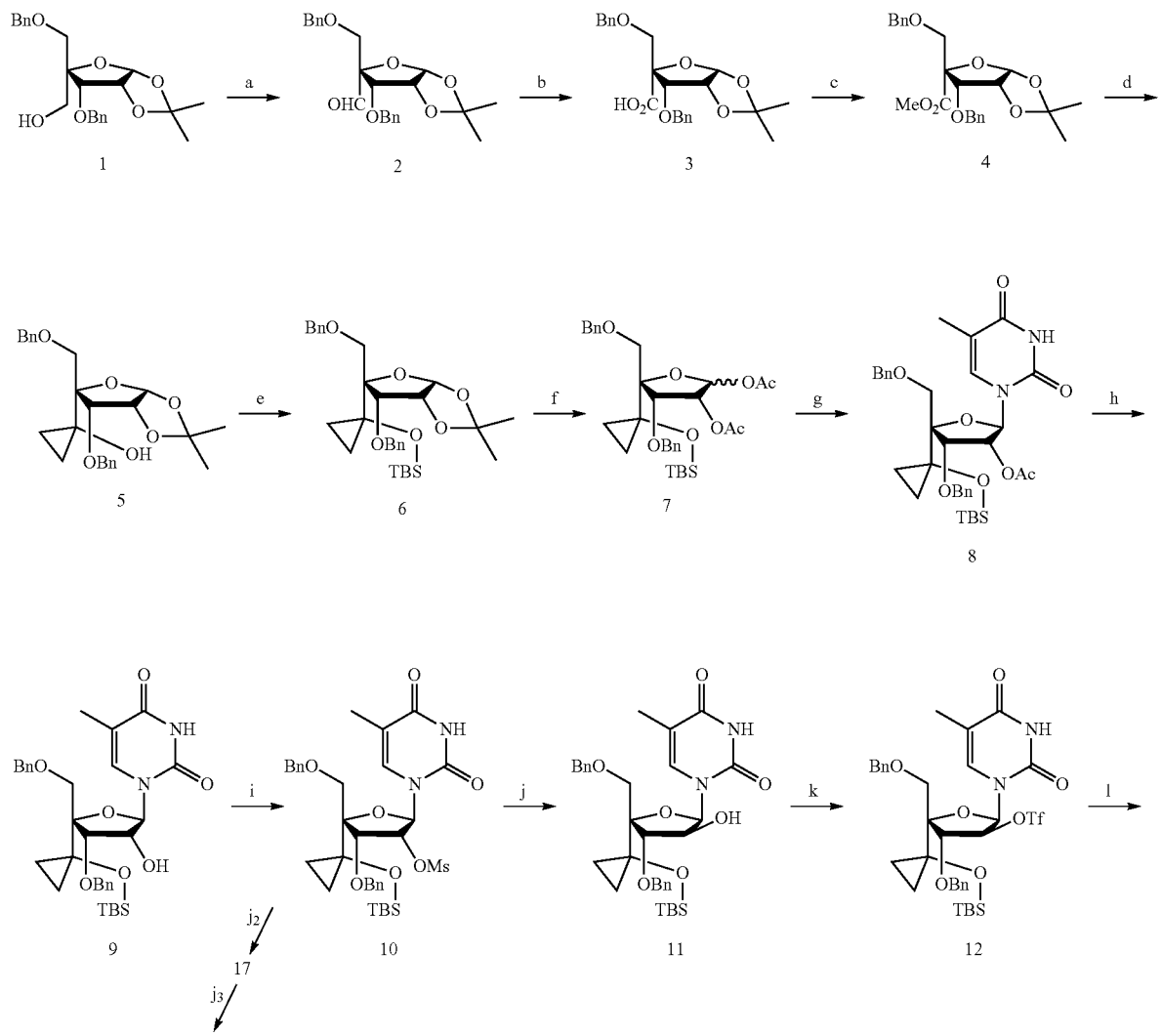

[Chemical 10]

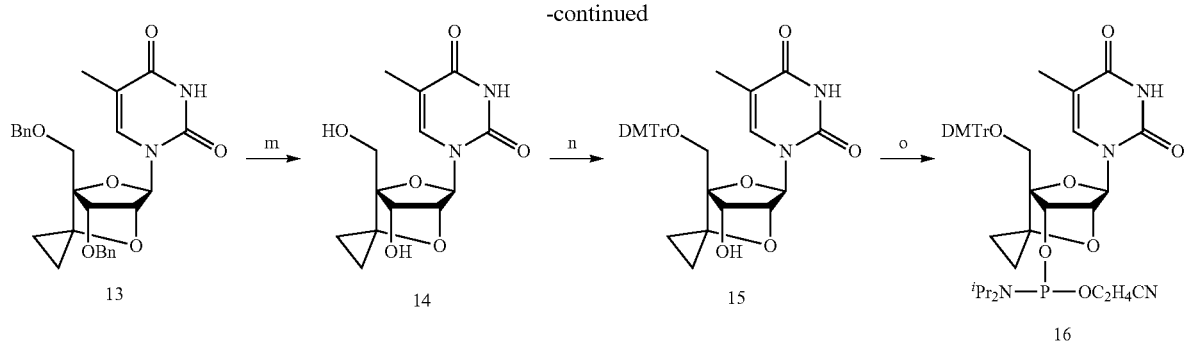

(1) Synthesis of Compound 2

(2) Synthesis of Compound 3

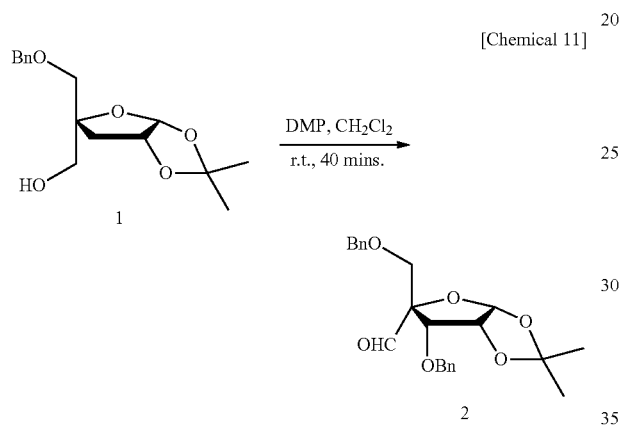

[Chemical 11]

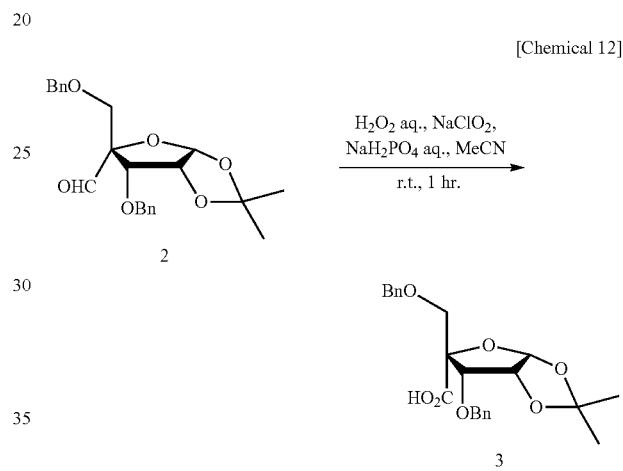

[Chemical 12]

Under nitrogen stream, to a solution (100 mL) of compound 1 (7.38 g, 18.5 mmol) in anhydrous dichloromethane was added Dess-Martin perioddinane (9.41 g, 22.2 mmol), and the mixture was stirred for 40 minutes at room temperature. After completion of the reaction, a saturated aqueous solution of sodium thiosulfate and a saturated aqueous solution of sodium bicarbonate (2:1 (v/v)) were added at 0° C., and the mixture was stirred at room temperature for 10 minutes. After the solvent was distilled away under reduced pressure, diethylether was added to the mixture which was then washed with water and saturated saline. Then, after the mixture was dried over anhydrous sodium sulfate, the solvent was distilled away to afford compound 2 (7.61 g, quantitative) as a colorless oil.

Table 1 shows the physical property data of the obtained compound 2.

TABLE 1

Physical property data of the obtained compound 2

$^1$H NMR (400 MHz, CDCl$_3$) δ 1.34 (s, 3H), 1.60 (s, 3H), 3.61 (d, J = 11.0 Hz, 1H), 3.67 (d, J = 11.0 Hz, 1H), 4.36 (d, J = 4.1 Hz, 1H), 4.46 (d, J = 12.4 Hz, 1H), 4.52 (d, J = 11.9 Hz, 1 H), 4.59 (d, J = 11.9 Hz, 1H), 4.60 (dd, J = 3.7, 4.6 Hz, 1H), 4.71 (d, J = 11.9 Hz, 1H), 5.84 (d, J = 3.7 Hz, 1H), 7.21-7.37 (m, 10H), 9.91 (s, 1H); $^{13}$C NMR (100 MHz, CDCl$_3$) δ 26.1, 26.5, 69.1, 72.8, 73.8, 78.3, 79.6, 89.7, 104.8, 114.1, 127.7, 127.8, 128.0, 128.1, 128.4, 128.5, 137.0, 137.5, 200.0; IR (KBr): 2985, 2973, 2866, 1731, 1496, 1213, 1165, 1103, 1020, 739, 699 cm$^{-1}$; $[α]_D^{29}$ +27.1 (c 1.03, MeOH); HRMS (MALDI) Calculated for C$_{23}$H$_{26}$O$_6$Na: 421.1622, Found: 421.1620.

To a solution (10 mmL) of compound 2 (7.61 g, 19.1 mmol) obtained above in acetonitrile were added sodium dihydrogenphosphate (0.2 M aqueous solution, 20 mL, 3.82 mmol) and a hydrogen peroxide solution (30 wt %, 2.3 mL, 21.0 mmol). To this mixture was added dropwise chlorous acid (0.75 M aqueous solution, 38 mL, 28.6 mmol) for 10 minutes, and then the mixture was stirred at room temperature for 1 hour. Then, to the reaction solution was added sodium sulfite (4.8 g, 19.1 mmol) at 0° C., and the mixture was stirred at room temperature for 10 minutes. After the solvent was distilled away under reduced pressure, extraction with ethyl acetate and washing with water and saturated saline were performed. After drying over anhydrous sodium sulfate, the solvent was distilled away under reduced pressure to afford compound 3 (7.61 g, 96%) as a white solid.

Table 2 shows the physical property data of the obtained compound 3.

TABLE 2

Physical property data of the obtained compound 3

M.P. 100-103° C.; $^1$H NMR (400 MHz, CDCl$_3$) δ 1.34 (s, 3H), 1.58 (s, 3H), 3.72 (d, J = 10.5 Hz, 1H), 3.77 (d, J = 11.0 Hz, 1H), 4.30 (d, J = 4.6 Hz, 1H), 4.49 (d, J = 11.9 Hz, 1H), 4.55 (d, J = 11.9 Hz, 1H), 4.65 (dd, J = 4.4, 4.4 Hz, 1H), 4.69 (d, J = 11.9 Hz, 1H), 4.80 (d, J = 11.9 Hz, 1H), 5.83 (d, J = 4.1 Hz, 1H), 7.21-7.40 (m, 10H); $^{13}$C NMR (100 MHz, CDCl$_3$) δ 25.2, 26.3, 71.6, 73.5, 74.1, 78.0, 78.2, 87.4, 104.8,

TABLE 2-continued

Physical property data of the obtained compound 3

114.6, 127.9, 128.1, 128.2, 128.5, 128.6, 128.8, 136.4, 137.4, 169.6; IR (KBr): 3171, 2985, 2937, 2870, 1768, 1497, 1163, 1098, 1020, 740, 698 cm$^{-1}$; $[\alpha]_D^{26}$ +42.3 (c 1.01, MeOH); HRMS (MALDI) Calculated for $C_{23}H_{26}O_7Na$: 437.1571, Found: 437.1570.

(3) Synthesis of Compound 4

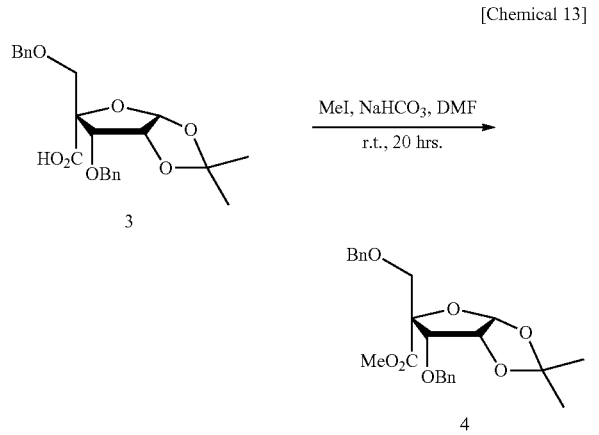

[Chemical 13]

Under nitrogen stream, to a solution (30 mL) of compound 3 (7.61 g, 18.4 mmol) obtained above in anhydrous N,N-dimethylformamide were added sodium bicarbonate (15.4 g, 184 mmol) and iodomethane (2.86 mL, 45.9 mmol), and the mixture was stirred for 20 hours. After completion of the reaction, a saturated aqueous solution of sodium thiosulfate and water were added to this mixture, and then extraction with diethyl ether was performed. After washing with water and saturated saline and drying over anhydrous sodium sulfate, the solvent was distilled away under reduced pressure to afford compound 4 (7.35 g, 93%) as a white solid.

Table 3 shows the physical property data of the obtained compound 4.

TABLE 3

Physical property data of the obtained compound 4

$^1$H NMR (400 MHz, CDCl$_3$) δ 1.38 (s, 3H), 1.64 (s, 3H), 3.67 (d, J = 10.1 Hz, 1H), 3.75 (s, 1H), 3.82 (d, J = 10.5 Hz, 1H), 4.25 (d, J = 5.0 Hz, 1H), 4.49 (d, J = 12.2 Hz, 1H), 4.54 (d, J = 11.9 Hz, 1H), 4.59 (d, J = 12.4 Hz, 1H), 4.67 (dd, J = 4.1, 5.0 Hz, 1H), 4.77 (d, J = 11.9 Hz, 1H), 5.89 (d, J = 4.2 Hz, 1H), 7.24-7.27 (m, 10H); $^{13}$C NMR (100 MHz, CDCl$_3$) δ 26.3, 27.3, 73.0, 73.7, 73.9, 79.4, 80.5, 89.7, 127.7, 127.7, 127.8, 127.9, 128.4, 128.6, 137.7, 169.4; IR (KBr): 2985, 2949, 2869, 1763, 1733, 1497, 1160, 1106, 1028, 738, 698 cm$^{-1}$; $[\alpha]_D^{27}$ +31.5 (c 1.00, MeOH); HRMS (MALDI) Calculated for $C_{24}H_{28}O_7Na$: 451.1727, Found: 451.1732.

(4) Synthesis of Compound 5

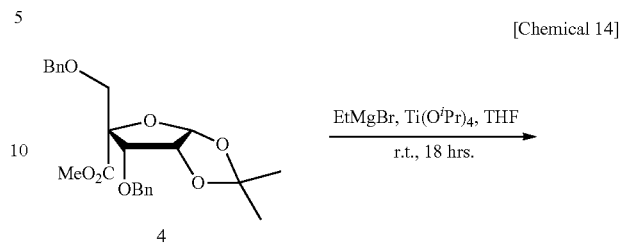

[Chemical 14]

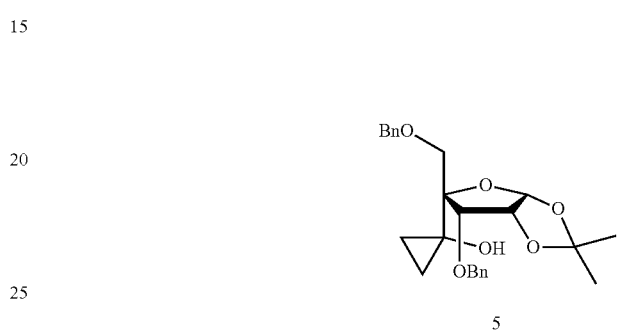

Under nitrogen stream, to a solution (14 mL) of compound 4 (500 mg, 1.17 mmol) obtained above in anhydrous tetrahydrofuran were added tetraisopropyl orthotitanate (0.35 mL, 1.17 mmol) and ethylmagnesium bromide (1 M tetrahydrofuran solution, 5.83 mL, 5.83 mmol) at 0° C., and the mixture was stirred at room temperature for 18 hours. After completion of the reaction, to this mixture was added a saturated aqueous solution of ammonium chloride, and the mixture was stirred for 10 minutes. After the solvent was distilled away under reduced pressure, extraction with ethyl acetate was performed, followed by washing with water and saturated saline. Furthermore, after drying over anhydrous sodium sulfate, the solvent was distilled away under reduced pressure to afford compound 5 (0.442 g, 89%) as a red paste.

Table 4 shows the physical property data of the obtained compound 5.

TABLE 4

Physical property data of the obtained compound 5

$^1$H NMR (400 MHz, CDCl$_3$) δ 0.55-0.67 (m, 3H), 1.16-1.21 (m, 1H), 1.39 (s, 3H), 1.61 (s, 3H), 3.36 (s, 1H), 3.48 (d, J = 9.6 Hz, 1H), 3.93 (d, J = 9.6 Hz, 1H), 4.33 (d, J = 6.0 Hz, 1H), 4.43 (d, J = 11.4 Hz, 1H), 4.45 (d, J = 11.9 Hz, 1H), 4.54 (d, J = 11.9 Hz, 1H), 4.84 (dd, J = 4.1, 6.0 Hz, 1H), 5.00 (d, J = 11.4 Hz, 1H), 5.88 (d, J = 4.1 Hz, 1H), 7.26-7.39 (m, 10H); $^{13}$C NMR (100 MHz, CDCl$_3$) δ 8.48, 11.0, 27.0, 27.8, 56.1, 73.0, 73.6, 75.3, 80.1, 81.9, 89.0, 106.4, 114.5, 127.4, 127.4, 127.7, 127.9, 128.4, 128.6, 137.7, 138.0; IR (KBr): 2935, 2867, 1496, 1454, 1252, 1099, 1027, 741, 699 cm$^{-1}$; $[\alpha]_D^{29}$ +93.5 (c 1.02, MeOH); HRMS (MALDI) Calculate for $C_{25}H_{30}O_6Na$: 449.1935, Found: 449.1939.

21
(5) Synthesis of Compound 6

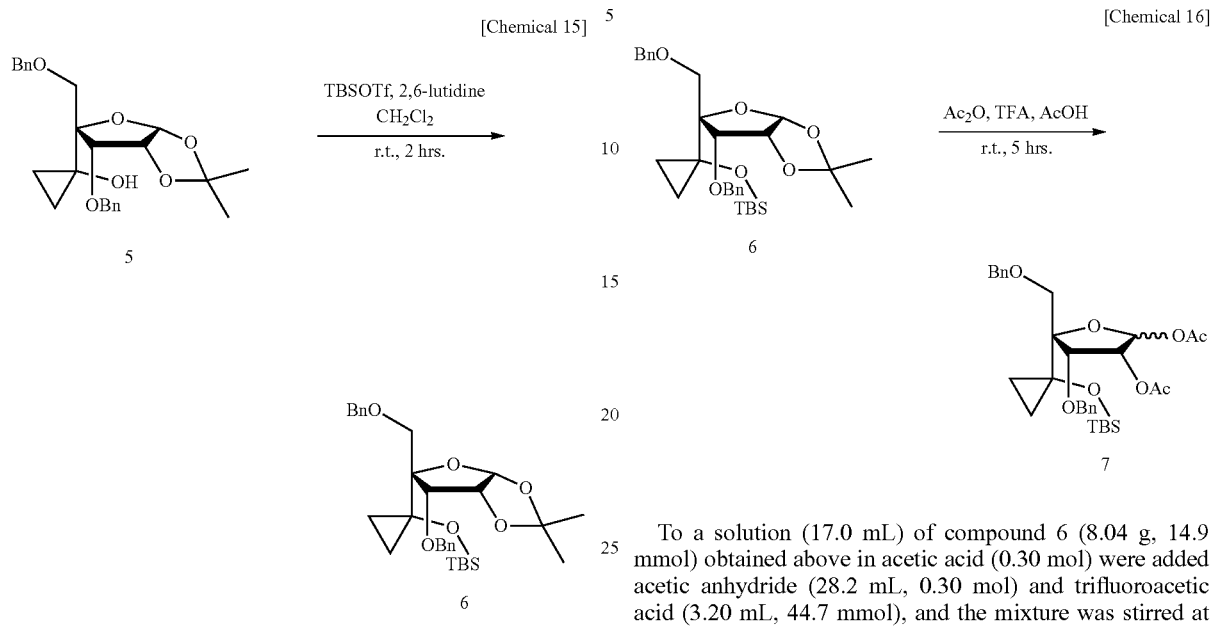

Under nitrogen stream, to a solution (50 mL) of compound 5 (2.55 g, 5.99 mmol) obtained above in anhydrous dichloromethane were added 2,6-lutidine (2.09 mL, 18.0 mmol) and tert-butyldimethylsilyl trifluoromethanesulfonate (2.75 mL, 12.0 mmol), and the mixture was stirred at room temperature for 2 hours. Then, to this mixture was added a saturated aqueous solution of sodium bicarbonate, followed by extraction with ethyl acetate and then washing with water and saturated saline. After drying over anhydrous sodium sulfate, the solvent was distilled away under reduced pressure. The resultant crude product was purified by silica-gel column chromatography (ethyl acetate:hexane=1:15 (v/v)→1:5 (v/v)) to afford compound 6 (2.92 g, 90%) as a yellow oil.

Table 5 shows the physical property data of the obtained compound 6.

TABLE 5

| Physical property data of the obtained compound 6 |
| --- |
| $^1$H NMR (400 MHz, CDCl$_3$) δ −0.06 (s, 3H), −0.02 (s, 3H), 0.56-0.63 (m, 1H), 0.70-0.77 (m, 2H), 0.72 (s, 9H), 1.18-1.25 (m, 1H), 1.34 (s, 3H), 1.43 (s, 3H), 3.46 (d, J = 9.6 Hz, 1H), 3.92 (d, J = 9.6 Hz, 1H), 4.00 (d, J = 6.0 Hz, 1H), 4.42 (d, J = 11.9 Hz, 1H), 4.52 (d, J = 11.0 Hz, 1H), 4.61 (d, J = 11.9 Hz, 1H), 4.87 (d, J = 11.4 Hz, 1H), 4.95 (dd, J = 4.6, 6.0 Hz, 1H), 5.88 (d, J = 4.6 Hz, 1H), 7.19-7.43 (m, 10H); $^{13}$C NMR (100 MHz, CDCl$_3$) δ −3.4, −3.1, 7.7, 10.2, 17.8, 25.7, 27.1, 28.5, 57.5, 73.4, 73.8, 76.2, 80.0, 83.3, 90.3, 106.1, 114.5, 126.8, 126.9, 127.6, 127.8, 127.8, 128.5, 138.0, 139.2; IR (KBr): 2929, 2858, 1497, 1455, 1279, 1254, 1106, 1040, 733, 696 cm$^{-1}$; [α]$_D^{29}$ +53.6 (c 1.01, MeOH); HRMS (MALDI) Calculated for C$_{31}$H$_{44}$O$_6$NaSi: 563.2799, Found: 563.2809. |

22
(6) Synthesis of Compound 7

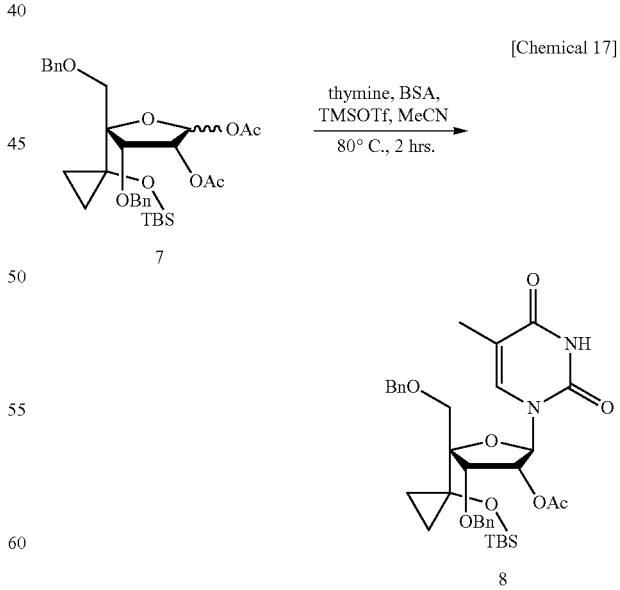

To a solution (17.0 mL) of compound 6 (8.04 g, 14.9 mmol) obtained above in acetic acid (0.30 mol) were added acetic anhydride (28.2 mL, 0.30 mol) and trifluoroacetic acid (3.20 mL, 44.7 mmol), and the mixture was stirred at room temperature for 5 hours. To this mixture was added a saturated aqueous solution of sodium bicarbonate, followed by extraction with ethyl acetate and then washing with water and saturated saline. After drying over anhydrous sodium sulfate, the solvent was distilled away under reduced pressure to afford compound 7 (9.43 g, crude product) as a reddish-brown oil. Compound 7 was immediately used for the next reaction without purification.

(7) Synthesis of Compound 8

Under nitrogen stream, to a solution (140 mL) of compound 7 (9.43 g, crude product) obtained above in anhydrous acetonitrile were added thymine (5.63 g, 44.6 mmol), N,O-bis(trimethylsilyl)acetamide (25% acetonitrile solution, 18.2 mL, 74.3 mmol), and trimethylsilyl trifluoromethanesulfonate (4.03 mL, 22.3 mmol) at room temperature, and the mixture was stirred at 80° C. for 2 hours. After completion of the reaction, to this mixture was added a saturated aqueous solution of sodium bicarbonate at 0° C., followed by extraction with ethyl acetate and then washing with water and saturated saline. After drying over anhydrous sodium sulfate, the solvent was distilled away under reduced pressure to afford compound 8 (8.26 g) as a reddish-brown oil.

Table 6 shows the physical property data of the obtained compound 8.

TABLE 6

Physical property data of the obtained compound 8

M.P. 47-50° C.; $^1$H NMR (400 MHz, CDCl$_3$) δ −0.01 (s, 3H), 0.03 (s, 3H), 0.65-0.70 (m, 2H), 0.77-1.03 (m, 2H), 0.78 (s, 9H), 1.56 (d, J = 0.9 Hz, 1H), 1.96 (s, 3H), 3.63 (d, J = 9.6 Hz, 1H), 4.03 (d, J = 10.1 Hz, 1H), 4.45 (d, J = 5.0 Hz, 1H), 4.51 (d, J = 11.0 Hz, 1H), 4.62 (d, J = 11.9 Hz, 1H), 4.72 (d, J = 11.5 Hz, 1H), 4.95 (d, J = 11.4 Hz, 1H), 5.50 (dd, J = 4.6, 8.7 Hz, 1 H), 6.24 (d, J = 8.7 Hz, 1H), 7.26-7.45 (m, 10H), 7.67 (d, J = 1.4 Hz, 1H), 8.31 (s, 1H); $^{13}$C NMR (100 MHz, CDCl$_3$) δ −4.7, −4.4, 5.9, 9.3, 10.9, 12.1, 16.6, 19.4, 24.4, 56.7, 72.6, 72.9, 73.8, 73.9, 79.5, 83.5, 86.3, 110.2, 126.0, 126.1, 126.6, 126.9, 127.0, 127.5, 134.6, 135.7, 137.3, 149.4, 162.2, 169.3; IR (KBr): 3499, 2955, 2929, 1714, 1683, 1470, 1274, 1233, 1127, 1075, 1036, 733, 699 cm$^{-1}$; [α]$_D^{24}$ −46.9 (c 0.99, MeOH); HRMS (MALDI) Calculated for C$_{35}$H$_{46}$N$_2$O$_8$NaSi: 673.2916, Found: 673.2917.

(8) Synthesis of Compound 9

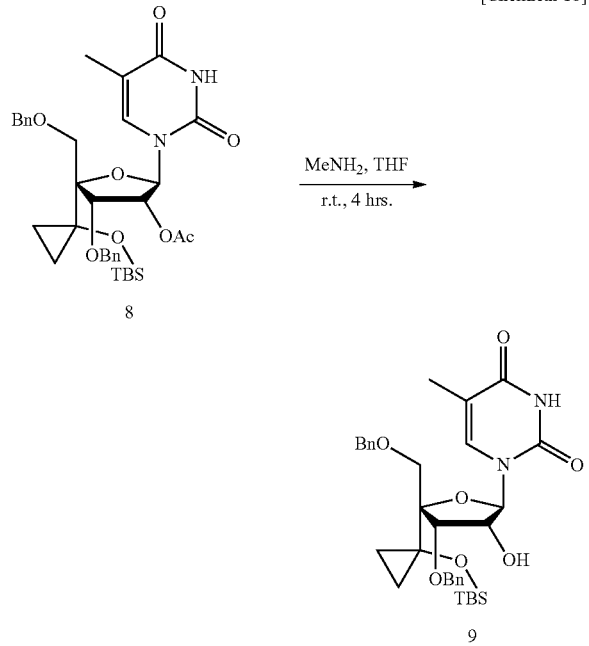

[Chemical 18]

To a solution (150 mL) of compound 8 (8.26 g, crude product) obtained above in tetrahydrofuran was added methylamine (40% aqueous solution, 30.4 mL, 0.73 mol), and the mixture was stirred at room temperature for 4 hours. After completion of the reaction, tetrahydrofuran was distilled away under reduced pressure. Extraction with ethyl acetate was performed, followed by washing with water and saturated saline. After drying over anhydrous sodium sulfate, the solvent was distilled away under reduced pressure to afford compound 9 (7.50 g) as a yellow foam.

Table 7 shows the physical property data of the obtained compound 9.

TABLE 7

Physical property data of the obtained compound 9

M.P. 36-39° C.; $^1$H NMR (400 MHz, CDCl$_3$) δ 0.03 (s, 3H), 0.06 (s, 3H), 0.69-0.77 (m, 3H), 0.80 (s, 9H), 0.94-1.00 (m, 1H), 1.60 (s, 3H), 2.88 (d, J = 11.9 Hz, 1H), 3.60 (d, J = 9.6 Hz, 1H), 4.02 (d, J = 9.6 Hz, 1H), 4.21 (d, J = 5.0 Hz, 1H), 4.55-4.59 (m, 3H), 4.69 (d, J = 11.4 Hz, 1H), 5.19 (d, J = 11.0 Hz, 1H), 5.84 (d, J = 8.2 Hz, 1H), 7.32-7.41 (m, 10H), 7.59 (d, J = 0.9 Hz, 1H), 8.47 (s, 1H); $^{13}$C NMR (100 MHz, CDCl$_3$) δ −3.4, −3.1, 7.2, 10.6, 12.1, 17.9, 25.7, 58.0, 74.0, 74.3, 74.5, 75.7, 82.5, 86.7, 87.6, 111.3, 127.8, 127.8, 128.0, 128.3, 128.6, 128.8, 135.9, 136.9, 137.7, 150.9, 163.4; IR (KBr): 3422, 2955, 2929, 1699, 1470, 1277, 1254, 1129, 1087, 1036, 751, 698 cm$^{-1}$; [α]$_D^{26}$ −45.1 (c 1.00, MeOH); HRMS (MALDI) Calculated for C$_{33}$H$_{44}$N$_2$O$_7$NaSi: 631.2810, Found: 631.2814.

(9) Synthesis of Compound 10

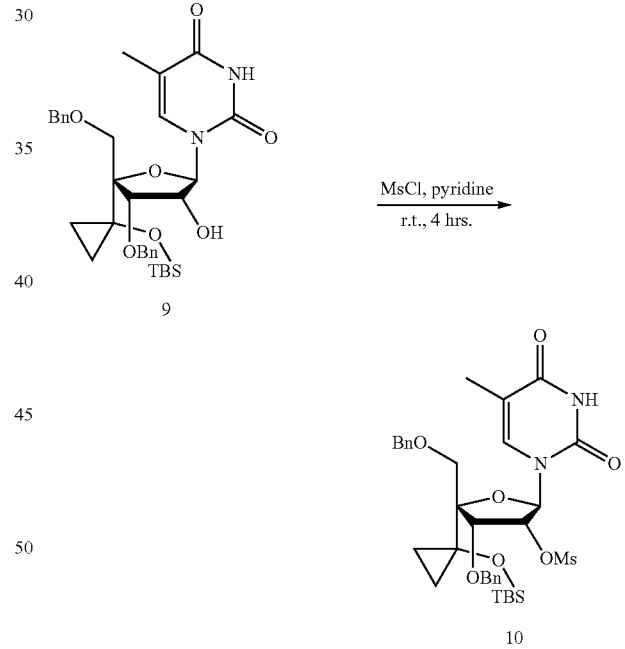

[Chemical 19]

Under nitrogen stream, to a solution (120 mL) of compound 9 (7.50 g, crude product) obtained above in anhydrous pyridine was added methanesulfonyl chloride (1.43 mL, 18.5 mmol), and the mixture was stirred at room temperature for 4 hours. After completion of the reaction, to this mixture was added water, followed by extraction with ethyl acetate and then washing with water and saturated saline. After drying over anhydrous sodium sulfate, the solvent was distilled away under reduced pressure. The resultant crude product was purified by silica-gel column chromatography (ethyl acetate:hexane=1:5 (v/v)) to afford compound 10 (7.39 g, 4 steps) as a white foamy solid.

Table 8 shows the physical property data of the obtained compound 10.

TABLE 8

Physical property data of the obtained compound 10

$^1$H NMR (400 MHz, CDCl$_3$) δ −0.01 (s, 3H), 0.04 (s, 3H), 0.61-0.84 (m, 3H), 0.78 (s, 9H), 0.94-1.01 (m, 1H), 1.56 (d, J = 0.9 Hz, 1H), 3.63 (d, J = 10.1 Hz, 1H), 4.03 (d, J = 9.6 Hz, 1H), 4.37 (d, J = 4.8 Hz, 1H), 4.63 (d, J = 11.5 Hz, 1H), 4.71 (d, J = 11.9 Hz, 1H), 4.78 (d, J = 11.0 Hz, 1H), 4.94 (d, J = 11.0 Hz, 1H), 5.58 (dd, J = 4.8, 8.5 Hz, 1H), 6.23 (d, J = 8.2 Hz, 1H), 7.26-7.42 (m, 10H), 7.60 (d, J = 1.4 Hz, 1H), 8.25 (s, 1H); $^{13}$C NMR (100 MHz, CDCl$_3$) δ −3.4, −3.1, 7.1, 10.6, 12.2, 17.9, 25.7, 38.2, 57.9, 73.9, 74.0, 75.1, 77.2, 81.0, 84.5, 87.6, 111.9, 127.4, 127.5, 127.9, 128.2, 128.4, 128.9, 135.3, 136.7, 138.3, 150.6, 163.2; IR (KBr): 3414, 2926, 1696, 1454, 1363, 1127, 1072, 1038, 748, 698 cm$^{-1}$; [α]$_D^{31}$ −48.2 (c 0.96, MeOH); HRMS (MALDI) Calculated for C$_{34}$H$_{46}$N$_2$O$_9$NaSiS: 709.2586, Found: 709.2582.

TABLE 9

Physical property data of the obtained compound 11

M.P.129-131° C.; $^1$H NMR (400 MHz, CDCl$_3$) δ − 0.06 (s, 3H), 0.00 (s, 3H), 0.57-0.91 (m, 4H), 0.74 (s, 9H), 1.80 (d, J = 0.9 Hz, 1H), 3.81 (d, J = 9.6 Hz, 1H), 4.15 (d, J = 10.1 Hz, 1H), 4.15 (s, 1H), 4.22 (dd, J = 3.5, 9.7 Hz, 1H), 4.63 (d, J = 11.5 Hz, 1H), 4.67 (d, J = 11.9 Hz, 1H), 4.72 (d, J = 11.9 Hz, 1H), 4.76 (d, J = 11.4 Hz, 1H), 4.96 (d, J = 11.9 Hz, 1H), 6.03 (d, J = 3.2 Hz, 1H), 7.26-7.44 (m, 11H), 8.13 (s, 1H); $^{13}$C NMR (100 MHz, CDCl$_3$) δ −3.3, −3.2, 8.0, 10.9, 12.6, 17.9, 25.7, 58.1, 73.2, 74.3, 74.4, 74.5, 87.0, 87.2, 87.5, 108.8, 127.0, 127.5, 128.2, 128.4, 129.0, 129.1, 135.6, 137.4, 138.0, 150.0, 163.5; IR (KBr): 2954, 1703, 1669, 1472, 1286, 1254, 1097, 1042, 738, 696 cm$^{-1}$; [α]$_D^{30}$ +36.3 (c 1.00, MeOH); HRMS (MALDI) Calculated for C$_{33}$H$_{44}$N$_2$O$_7$NaSi: 631.2810, Found: 631.2813.

(10) Synthesis of Compound 11

[Chemical 20]

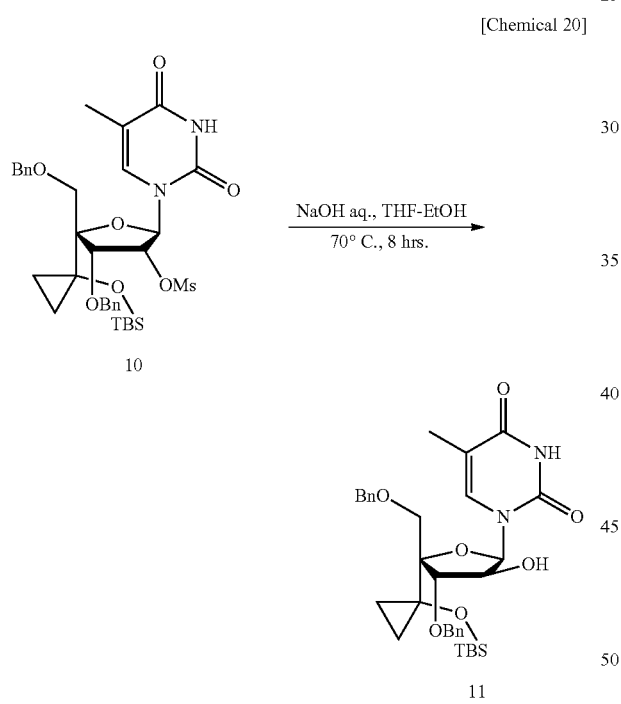

(11) Synthesis of Compound 12

[Chemical 21]

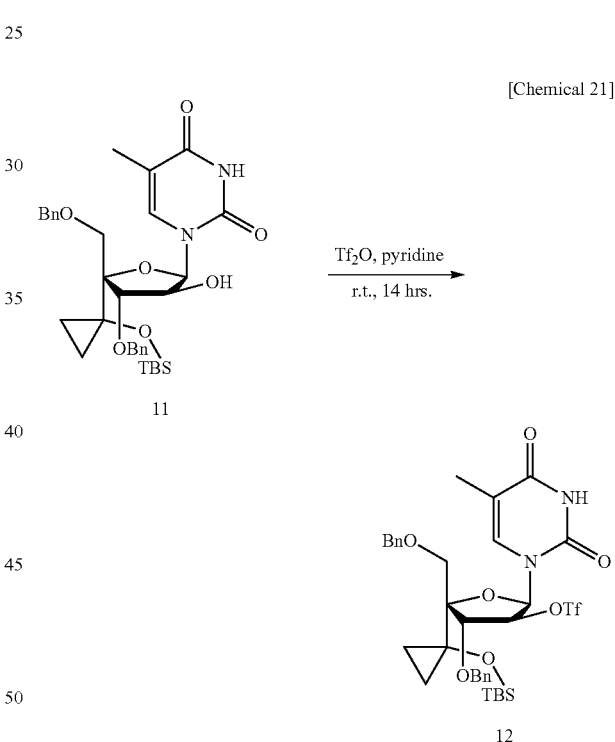

To a solution (150 mL) of compound 10 (3.19 g, 4.64 mmol) obtained above in tetrahydrofuran-ethanol (3:2 (v/v)) was added sodium hydroxide (4 M, aqueous solution, 60 mL, 0.23 mol), and the mixture was stirred at 70° C. for 8 hours. After completion of the reaction, the mixture was neutralized with hydrochloric acid, and the solvent was distilled away under reduced pressure. After extraction with ethyl acetate, washing with saturated saline and water was performed. After drying over anhydrous sodium sulfate, the solvent was distilled away under reduced pressure to afford compound 11 (2.71 g, crude product) as a white solid.

Table 9 shows the physical property data of the obtained compound 11.

Under nitrogen stream, to a solution (50 mL) of compound 11 (2.71 g, crude product) in anhydrous pyridine was added trifluoroacetic anhydride (3.65 mL, 22.3 mmol), and the mixture was stirred at room temperature for 12 hours. Furthermore, to this mixture was added trifluoroacetic anhydride (0.73 mL, 4.45 mmol), and the mixture was stirred at room temperature for 2 hours. Then, to this mixture was added water, followed by extraction with ethyl acetate and then washing with water and saturated saline. After drying over anhydrous sodium sulfate, the solvent was distilled away under reduced pressure to afford compound 12 (4.12 g, crude product) as a brown foamy solid. Compound 12 was immediately used for the next reaction without purification.

(12) Synthesis of Compound 13 (A)

(12)-2 Synthesis of Compound 13 (B)

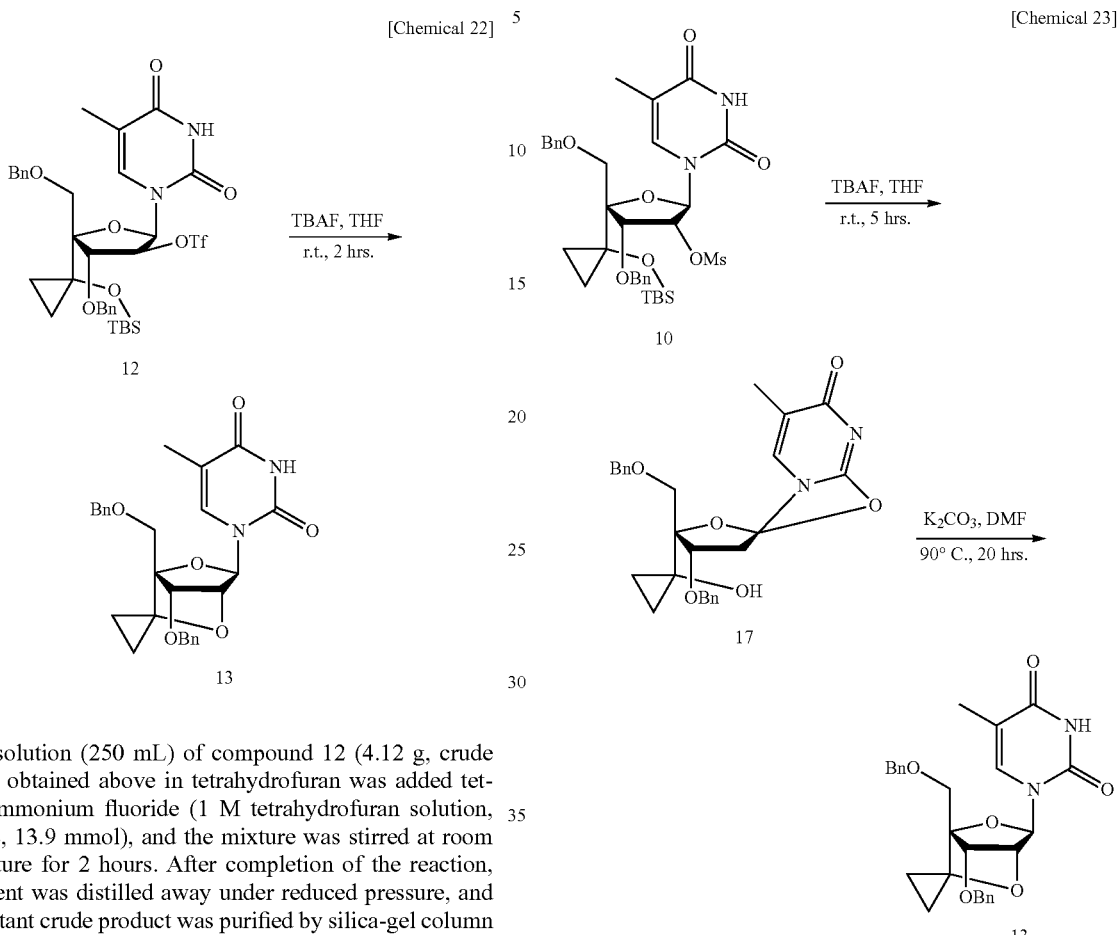

To a solution (250 mL) of compound 12 (4.12 g, crude product) obtained above in tetrahydrofuran was added tetrabutylammonium fluoride (1 M tetrahydrofuran solution, 13.9 mL, 13.9 mmol), and the mixture was stirred at room temperature for 2 hours. After completion of the reaction, the solvent was distilled away under reduced pressure, and the resultant crude product was purified by silica-gel column chromatography (ethyl acetate:hexane=2:3 (v/v)) to afford compound 13 (710 mg, 32%, 3 steps) as a yellow foamy solid.

Table 10 shows the physical property data of compound 13 obtained by synthesis (A) above.

TABLE 10

Physical property data of the compound 13 obtained by synthesis (A) above

M.P. 37-40° C.; $^1$H NMR (400 MHz, CDCl$_3$) δ 0.68-0.74 (m, 2H), 0.88-1.00 (m, 2H), 1.62 (d, J = 0.9 Hz, 1H), 3.50 (d, J = 10.5 Hz, 1H), 3.63 (d, J = 10.6 Hz, 1H), 4.04 (s, 1H), 4.51 (s, 1H), 4.56 (s, 2H), 4.58 (d, J = 11.0 Hz, 1H), 4.70 (d, J = 11.9 Hz, 1H), 5.73 (s, 1H), 7.26-7.42 (m, 10H), 7.51 (d, J = 0.9 Hz, 1H), 8.13 (s, 1H); $^{13}$C NMR (100 MHz, CDCl$_3$) δ 5.3, 9.9, 12.4, 64.1, 68.4, 72.2, 74.0, 77.1, 87.1, 87.6, 110.3, 127.7, 127.8, 128.2, 128.2, 128.6, 128.7, 135.1, 137.3, 137.5, 150.0, 164.1; IR (KBr): 3512, 3031, 1693, 1455, 1269, 1108, 1054, 761, 738, 699 cm$^{-1}$; $[\alpha]_D^{22}$ +55.3 (c 1.00, MeOH); HRMS (MALDI) Calculated for C$_{27}$H$_{28}$N$_2$O$_6$Na: 499.1840, Found: 499.1829.

Instead of "synthesis of compound 13 (A) above", in "synthesis (B)", compound 13 was newly synthesized from compound 10 via compound 17 in the following manner.

Under nitrogen stream, to a solution (25 mL) of compound 10 (459 mg, 0.67 mmol) in anhydrous tetrahydrofuran was added tetrabutylammonium fluoride (1 M tetrahydrofuran solution, 0.67 mL, 0.67 mmol), and the mixture was stirred at room temperature for 5 hours. After completion of the reaction, water was added, followed by extraction with ethyl acetate and then washing with water and saturated saline. After drying over anhydrous sodium sulfate, the solvent was distilled away under reduced pressure. The resultant crude product was purified by silica-gel column chromatography ((chloroform:methanol=50:1 (v/v)→20:1 (v/v)) to afford compound 17 (290 mg, 91%) as a white solid.

Table 11 shows the physical property data of the obtained compound 17.

TABLE 11

Physical property data of the obtained compound 17

M.P. 56-60° C.; $^1$H NMR (300 MHz, CDCl$_3$) δ 0.65-0.75 (m, 4H), 1.92 (d, J = 0.9 Hz, 1H), 3.24 (s, 1H), 3.31 (d, J = 10.5 Hz, 1H), 3.60 (d, J = 10.5 Hz, 1H), 4.24 (d, J = 12.0 Hz, 1H),

TABLE 11-continued

Physical property data of the obtained compound 17

4.33 (d, J = 12.3 Hz, 1H), 4.59-4.63 (m, 2H), 4.85 (d, J = 11.7 Hz, 1H), 5.36 (dd, J = 2.1, 6.0 Hz, 1H), 6.15 (d, J = 6.3 Hz, 1H), 7.08-7.12 (m, 3H), 7.26-7.40 (m, 8H); $^{13}$C NMR (75 MHz, CDCl$_3$) δ 10.0, 10.8, 14.2, 56.5, 70.9, 73.3, 73.8, 85.9, 87.0, 89.7, 90.8, 118.9, 128.0, 128.1, 128.1, 128.5, 128.7, 129.0, 130.2, 136.1, 136.9, 159.6, 172.6; IR (KBr): 3330, 3069, 2923, 1665, 1633, 1556, 1487, 128, 1087, 736, 700 cm$^{-1}$; $[\alpha]_D^{26}$ −2.24 (c 1.00, MeOH); HRMS (MALDI) Calculated for C$_{27}$H$_{29}$N$_2$O$_6$: 477.2020, Found: 477.2024.

Then, to a solution (35 mL) of compound 17 (1.62 g, 3.40 mmol) in N,N-dimethylformamide was added potassium carbonate (1.1 g, 10.2 mmol), and the mixture was stirred at 90° C. for 20 hours. After completion of the reaction, water was added, followed by extraction with diethyl ether and then washing with water and saturated saline. After drying over anhydrous sodium sulfate, the solvent was distilled away under reduced pressure. The resultant crude product was purified by silica-gel column chromatography (hexane:ethyl acetate=1:1 (v/v)) to afford compound 13 (1.23 g, 77%) as a white solid.

Table 12 shows the physical property data of compound 13 obtained by synthesis (B) above.

TABLE 12

Physical property data of the compound 13 obtained by synthesis (B) above $^1$H NMR (300 MHz, CDCl$_3$) δ 0.65-0.76 (m, 2H), 0.91-1.01 (m, 2H), 1.62 (s, 3H), 3.50 (d, J = 11.1 Hz, 1H), 3.63 (d, J = 10.8 Hz, 1H), 4.04 (s, 1H), 4.51-4.59 (m, 4H), 4.70 (d, J = 12.0 Hz, 1H), 5.73 (s, 1H), 7.26-7.39 (m, 10H), 7.51 (d, J = 0.9 Hz, 1H), 8.33 (s, 1H); $^{13}$C NMR (100 MHz, CDCl$_3$) δ 5.3, 9.9, 12.4, 64.1, 68.4, 72.2, 74.0, 77.1, 87.1, 87.6, 110.3, 127.7, 127.8, 127.8, 128.2, 128.6, 128.7, 128.7, 135.1, 137.3, 137.5, 150.0, 164.1; IR (KBr): 3512, 3031, 1693, 1455, 1269, 1108, 1054, 761, 738, 699 cm$^{-1}$; $[\alpha]_D^{22}$ +55.3 (c 1.00, MeOH); HRMS (MALDI) Calculated for C$_{27}$H$_{28}$N$_2$O$_6$Na: 499.1840, Found: 499.1829.

(13) Synthesis of Compound 14

[Chemical 24]

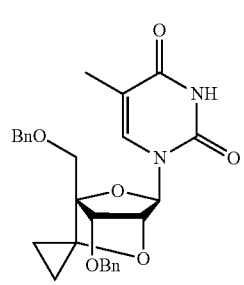

13

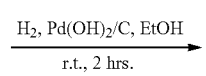

H$_2$, Pd(OH)$_2$/C, EtOH
r.t., 2 hrs.

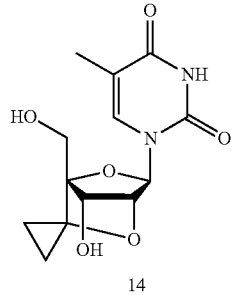

14

Under hydrogen stream, to a solution (20 mL) of compound 13 (350 mg, 1.50 mmol) obtained above in ethanol was added 20% palladium hydroxide/carbon (palladium 20%, 170 mg), and the mixture was stirred at room temperature for 2 hours. After filtration of the reaction mixture, the solvent was distilled away under reduced pressure to afford compound 14 (230 mg, crude product) as a white foamy solid.

Table 13 shows the physical property data of the obtained compound 14.

TABLE 13

Physical property data of the obtained compound 14

$^1$H NMR (400 MHz, CD$_3$OD) δ 0.72-0.79 (m, 3H), 0.86-0.89 (m, 1H), 1.88 (d, J = 0.9 Hz, 3H), 3.55 (d, J = 12.4 Hz, 1H), 3.72 (d, J = 12.4 Hz, 1H), 4.18 (s, 1H), 4.31 (s, 1H), 5.62 (s, 1H), 7.78 (d, J = 1.4 Hz, 1H); $^{13}$C NMR (76 MHz, CD$_3$OD) δ 5.1, 9.9, 12.6, 56.8, 68.7, 71.9, 81.0, 88.1, 89.9, 110.7, 137.0, 151.9, 166.5; IR (KBr): 3479, 3076, 1695, 1472, 1269, 1105, 1041 cm$^{-1}$; $[\alpha]_D^{20}$ +25.2 (c 1.01, MeOH); HRMS (MALDI) Calculated for C$_{13}$H$_{16}$N$_2$O$_6$Na: 319.0901, Found: 319.0882.

(14) Synthesis of Compound 15

[Chemical 25]

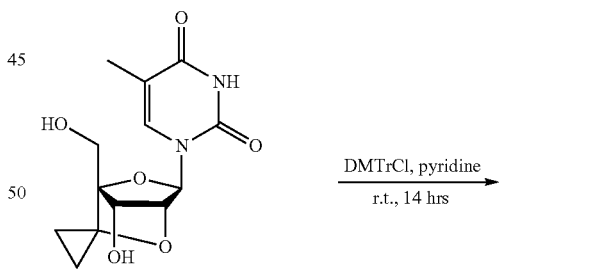

DMTrCl, pyridine
r.t., 14 hrs

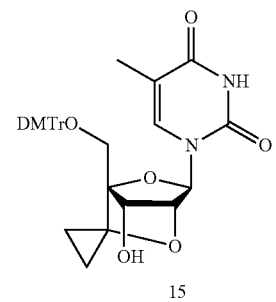

15

Under nitrogen stream, to a solution (15 mL) of compound 14 (130 mg, crude product) obtained above in anhydrous pyridine was added 4,4'-dimethoxytrityl chloride (892 mg, 2.63 mmol), and the mixture was stirred at room temperature for 14 hours. To this mixture was added water, followed by extraction with dichloromethane, and then washing with water and saturated saline. After drying over anhydrous sodium sulfate, the solvent was distilled away under reduced pressure. The resultant crude product was purified by silica-gel column chromatography (0.5% triethylamine-containing chloroform:methanol=50:1 (v/v)) to afford compound 15 (160 mg, 60%) as a white foamy solid.

Table 14 shows the physical property data of the obtained compound 15.

TABLE 14

Physical property data of the obtained compound 15

$^1$H NMR (400 MHz, CDCl$_3$) δ 0.49-0.57 (m, 1H), 0.74-0.78 (m, 1H), 0.85-0.94 (m, 2H), 1.73 (d, J = 0.9 Hz, 3H), 3.15 (d, J = 11.0 Hz, 1H), 3.35 (d, J = 11.0 Hz, 1H), 3.79 (s, 4H), 4.32 (s, 1H), 4.47 (s, 1H), 5.76 (s, 1H), 6.84 (d, J = 8.2 Hz, 4H), 7.22-7.35 (m, 9H), 7.45 (dd, J = 1.4, 8.7 Hz, 2H), 7.66 (d, J = 1.4 Hz, 1H); $^{13}$C NMR (100 MHz, CDCl$_3$) δ 5.3, 9.6, 12.7, 55.3, 58.0, 68.0, 72.6, 79.7, 86.8, 87.0, 88.0, 110.6, 113.4, 127.2, 128.1, 128.2, 130.1, 130.2, 134.8, 135.2, 135.4, 144.4, 150.1, 158.8, 164.3; IR (KBr): 3430, 2933, 1696, 1509, 1254, 1177, 1053, 829, 757 cm$^{-1}$; [α]$_D^{21}$ −16.2 (c 1.00, MeOH); HRMS (MALDI) Calculated for C$_{34}$H$_{34}$N$_2$O$_8$Na: 621.2207, Found: 621.2208.

(15) Synthesis of Compound 16

[Chemical 26]

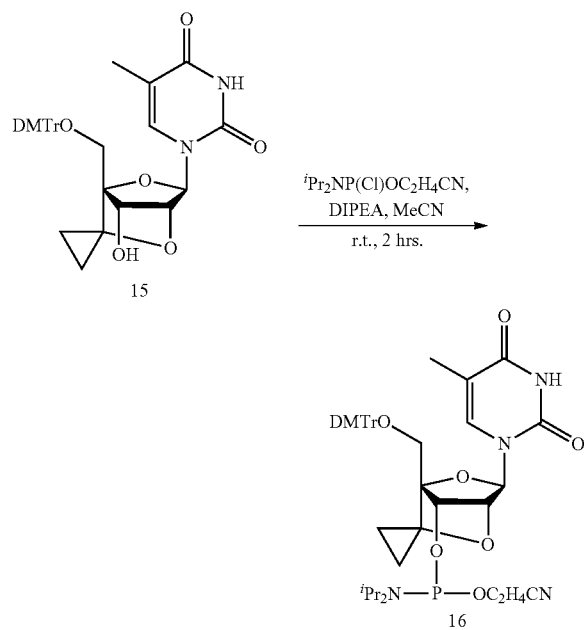

Under nitrogen stream, to a solution (1.0 mL) of compound 15 (30.0 mg, 0.05 mmol) obtained above in anhydrous acetonitrile were added N,N-diisopropylethylamine (34.8 μL, 0.20 mmol) and 2-cyanoethyl-N,N-diisopropyl phosphorochloridate (22.3 μL, 0.10 mmol), and the mixture was stirred at room temperature for 2 hours. The solvent was distilled away under reduced pressure, and the resultant crude product was purified by silica-gel column chromatography (0.5% triethylamine-containing ethyl acetate:hexane=2:1 (v/v)) to afford compound 16 (24 mg, 60% (scpBNA-T amidite block)) as a white foamy solid.

Table 15 shows the physical property data of the obtained compound 16.

TABLE 15

Physical property data of the obtained compound 16

$^1$H NMR (300 MHz, CDCl$_3$) δ 0.36-0.45 (m, 1H), 0.70-0.89 (m, 3H), 1.00 (d, J = 6.5 Hz, 3H), 1.07 (d, J = 6.5 Hz, 3H), 1.12 (d, J = 6.9 Hz, 3H), 1.15 (d, J = 6.9 Hz, 3H), 1.68 (d, J = 0.7 Hz, ½H), 1.69 (d, J = 1.1 Hz, ½H), 2.40 (m, 1H), 2.56 (m, 1H), 3.18 (d, J = 10.3 Hz, ½H), 3.20 (d, J = 10.3 Hz, ½H), 3.28 (d, J = 10.7 Hz, ½H), 3.28 (d, J = 10.7 Hz, ½H), 3.46-3.58 (m, 3H), 3.64-3.76 (m, 1H), 3.80 (s, 3H), 3.81 (s, 3H), 4.37 (d, J = 6.5 Hz, ½H), 4.42 (d, J = 8.6 Hz, ½H), 4.61 (s, ½H), 4.64 (s, ½H), 5.78 (s, 1H), 6.82-6.87 (m, 4H), 7.21-7.34 (m, 6H), 7.43-7.47 (m, 2H), 7.71 (d, J = 1.0 Hz, ½H), 7.74 (d, J = 1.1 Hz, ½H), 8.72 (s, 1H); $^{31}$P NMR (161.8 MHz, CDCl$_3$) δ 148.6; HRMS (FAB) Calculated for C$_{43}$H$_{52}$O$_9$N$_4$P: 799.3472, Found: 799.3475.

Example 2

Synthesis and Purification of Oligonucleotides

Compound 16 (amidite block) obtained in Example 1 and dG(iBu), dC(Bz), and T phosphoramidites (all of which are manufactured by Sigma-Aldrich) were individually prepared as 0.1 M anhydrous acetonitrile solutions, and oligonucleotides (5'-d(GCGTTXTTTGCT)-3', 5'-d(GCGTTX-TXTGCT)-3', 5'-d(GCGTTXXTTGCT)-3', 5'-d(GCGXTXTXTGCT)-3', 5'-d(GCGTTXXXTGCT)-3', and 5'-d(TTTTTTTTXT)-3') were synthesized using an nS-8 Oligonucleotides Synthesizer (oligonucleotide synthesizer manufactured by GeneDesign, Inc.) according to a phosphoramidite method that is known in the art (here, X corresponds to compound 16 (amidite block) obtained in Example 1).

In this synthesis, the synthesis scale was 0.2 μmol, and the synthesis was performed trityl-on. Activator 42 (0.25 M acetonitrile solution manufactured by Sigma-Aldrich) was used as an activator. Condensation time was 8 minutes for the synthesis using compound 16 and 32 seconds for the synthesis using the other natural amidite blocks. After completion of the synthesis, the oligonucleotides were treated with 28% aqueous ammonia at room temperature for 1.5 hours, thus cleaved from the column support, and subsequently allowed to stand at 55° C. for 12 hours to thereby deprotect the base moiety and the phosphoric diester moiety. Then, the oligonucleotides were purified on a simplified reverse-phase column (Sep-Pak (registered trademark) Plus C18 Environmental Cartridges manufactured by Waters) and further purified by reverse-phase HPLC.

It should be noted that this HPLC was performed under the following conditions.

Xbridge (registered trademark) MS C$_{18}$ columns 2.5 μmol (4.6 mm×50 mm, 10 mm×50 mm) manufactured by Waters were used as the columns. A 0.1 M triethyl ammonium acetate (TEAA) buffer (pH 7.0) and 0.1 M TEAA buffer: acetonitrile=1:1 (v/v) were prepared as the solution A and the solution B, respectively, of the mobile phase, and with respect to the concentration of the solution B, a gradient of 6 to 12% (30 minutes) was performed. The analysis was performed at 1 mL/min, and the fractionation was performed at 3 mL/min. The detection UV was at 254 nm.

Furthermore, oligonucleotides were synthesized in the same manner as described above using, instead of compound 16 (amidite block) above, 2',4'-BNA/LNA (having the same structure as compound 16 obtained in Example 1 above except that no spirocyclopropane group is present at the position 6' in the bridge portion) synthesized using the method described in Obika et al., Tetrahedron Lett., 1997, 38, pp. 8735-8738.

Also, oligonucleotides were synthesized in the same manner as described above using natural thymidine (manufactured by Sigma-Aldrich) instead of compound 16 (amidite block) above.

Example 3

Determination and Quantification of the Composition of Oligonucleotides

The compositions of the oligonucleotides obtained in Example 2 were determined by MALDI-TOF-MASS. For this measurement, first, a matrix (1 μL) obtained by mixing an aqueous solution of 3-hydroxypicolinic acid (10 mg/mL) and an aqueous solution of ammonium citrate (1 mg/mL) in a volume ratio of 1:1 was dried on a measurement plate. An oligonucleotide (50 μM, 1 μL) dissolved in water was placed on the dried matrix and then dried. After that, measurement was performed. The molecular weight was measured in a negative reflector mode, and oligothymidylic acids (7 mer, 15 mer, and 23 mer) were used as external standards. Also, the synthesized oligonucleotides were quantified by measuring ultraviolet absorption spectra at 260 nm using an absorbance measurement apparatus (SHIMADZU UV-1800 manufactured by Shimadzu Corporation).

Table 16 shows the results.

TABLE 16

| | MALDI-TOF MS | | |
|---|---|---|---|
| Oligonucleotide | Yield (%) | Calcd.[M − H]⁻ | Found [M − H]⁻ |
| 5'-d(GCGTTXTTTGCT)-3' | 26 | 3686.4 | 3686.8 |
| 5'-d(GCGTTXTXTGCT)-3' | 36 | 3740.5 | 3740.3 |
| 5'-d(GCGTTXXTTGCT)-3' | 12 | 3740.5 | 3741.0 |
| 5'-d(GCGXTXTXTGCT)-3' | 41 | 3794.5 | 3794.6 |
| 5'-d(GCGTTXXXTGCT)-3' | 8 | 3794.5 | 3794.6 |
| 5'-d(TTTTTTTTXT)-3' | 23 | 3033.0 | 3032.5 |

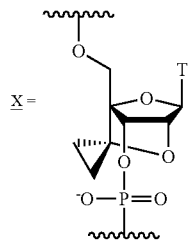

Example 4

Determination of the Melting Temperature ($T_m$)

In this example, with respect to target strands, that is, a single-stranded oligo-DNA and a single-stranded oligo-RNA (each synthesized according to a phosphoramidite method as in Example 1) having the sequence (SEQ ID NO: 1) of 5'-(AGCAAAAAACGC)-3', the hybridization ability (binding affinity) of the various types of oligonucleotides from Example 2 was determined.

After the various types of oligonucleotides and the target strands were subjected to an annealing treatment to form double strands, their $T_m$ values were measured to determine the hybridization ability of the oligonucleotides. The $T_m$ values of the formed double strands were measured.

Specifically, phosphate buffers (10 mM, pH 7.2, 130 μL) containing respective oligonucleotides (final concentration 4 μM) and sodium chloride (final concentration 100 mM) were bathed in boiled water and then slowly cooled to room temperature. SHIMADZU UV-1650PC and SHIMADZU UV-1800 spectrometers (manufactured by Shimadzu Corporation) were used as measurement apparatuses. Under nitrogen stream, each measurement solution was cooled to 5° C. before starting the measurement. The temperature was raised to 90° C. at the rate of 0.5° C./min while absorbance at 260 nm was plotted at intervals of 0.5° C. The $T_m$ value was calculated using a median method, and a mean value of three independent measurements was adopted.

Table 17 shows the results in the cases where the single-stranded oligo-DNA was used as the target strand, and Table 18 shows the results in the cases where the single-stranded oligo-RNA was used as the target strand. Both of the tables show the $T_m$ value, which means the temperature at which 50% of the double strands dissociate, and the difference in $T_m$ value per modification unit (in the cases where compound 16 (amidite block) was used and in the cases where 2',4'-BNA/LNA was used).

TABLE 17

| | $T_m$ ($\Delta T_m$/mod.) (° C.) | | |
|---|---|---|---|
| Oligonucleotide | T = Natural thymidine | 2',4'-BNA/LNA | Compound 16 |
| 5'-d(GCGTT<u>T</u>TTTGCT)-3' | 51.5 | 52.6 (+1.1) | 52.5 (+1.0) |
| 5'-d(GCGTT<u>T</u>T<u>T</u>TGCT)-3' | | 54.1 (+1.3) | 53.5 (+1.0) |
| 5'-d(GCGTT<u>TT</u>TTGCT)-3' | | 53.1 (+0.8) | 52.3 (+0.4) |
| 5'-d(GCGTT<u>TTT</u>TGCT)-3' | | 56.4 (+1.6) | 55.2 (+1.2) |
| 5'-d(GCGTT<u>TTTT</u>GCT)-3' | | 55.0 (+1.2) | 53.6 (+0.7) |

TABLE 18

| | $T_m$ ($\Delta T_m$/mod.) (° C.) | | |
|---|---|---|---|
| Oligonucleotide | T = Natural thymidine | 2',4'-BNA/LNA | Compound 16 |
| 5'-d(GCGTT<u>T</u>TTTGCT-3' | 47.8 | 51.8 (+4.0) | 52.6 (+4.8) |
| 5'-d(GCGTT<u>T</u>T<u>T</u>TGCT-3' | | 57.7 (+5.0) | 58.0 (+5.1) |
| 5'-d(GCGTT<u>TT</u>TTGCT-3' | | 57.3 (+4.8) | 57.3 (+4.8) |
| 5'-d(GCGTT<u>TTT</u>TGCT-3' | | 62.6 (+5.0) | 62.6 (+4.9) |
| 5'-d(GCGTT<u>TTTT</u>GCT-3' | | 62.0 (+4.7) | 62.1 (+4.8) |

As is clear from Tables 17 and 18, the oligonucleotides containing compound 16 (amidite block) had higher $T_m$ values with respect to both of the single-stranded oligo-DNA and the single-stranded oligo-RNA than the natural oligonucleotide, thereby exhibiting high binding affinities. In particular, with respect to the single-stranded oligo-RNA, the oligonucleotides containing compound 16 (amidite block) exhibited high binding affinities comparable to the binding affinities of those containing 2',4'-BNA/LNA.

FIG. 1 shows $T_m$ curves indicating dissociation of the double-stranded hybrids which the various types of oligonucleotides having the sequence of 5'-d(GCGTTXTTT-GCT)-3' have formed with the single-stranded oligo-RNA target strand. In FIG. 1, the vertical axis indicates absorbance at 260 nm, and the horizontal axis indicates temperature (° C.).

It was also clear from FIG. 1 that the oligonucleotides containing compound 16 (amidite block) exhibit high binding affinities for the single-stranded oligo-RNA which are comparable to the binding affinities of those containing 2',4'-BNA/LNA.

Example 5

Assessment of the Nuclease-Resistant Ability

Various types of 10-mer oligonucleotides in which compound 16 (amidite block) of Example 1, 2',4'-BNA/LNA (T), and natural thymidine were respectively used as X in the sequence of 5'-d(TTTTTTTTXT)-3' were prepared in the following manner. That is to say, for oligo synthesis, phosphoramidites of the raw material nucleosides were adjusted as 0.1 M anhydrous acetonitrile solutions, and the synthesis was performed using an nS-8 Oligonucleotides Synthesizer (oligonucleotide synthesizer manufactured by GeneDesign, Inc.) according to an ordinary phosphoramidite method. In this synthesis, the synthesis scale was 1.0 μmol, and the synthesis was performed trityl-on. Activator 42 (0.25 M acetonitrile solution manufactured by Sigma-Aldrich) was used as the activator. The condensation time was 10 minutes for the synthesis using compound 16, and 40 seconds for the synthesis using the other natural amidite blocks. After completion of the synthesis, the column support was transferred into a microtube and allowed to stand overnight at 55° C. in 28% aqueous ammonia to cleave the oligonucleotides from the column support and deprotect the base moiety and the phosphoric diester moiety. Then, the oligonucleotides were purified on a simplified reverse-phase column (Sep-Pak (registered trademark) Plus C18 Environmental Cartridges manufactured by Waters) and further purified by reverse-phase HPLC. The conditions for the HPLC were as follows. Xbridge (registered trademark) MS $C_{18}$ columns 2.5 μmol (4.6 mm×50 mm, 10 mm×50 mm) manufactured by Waters were used as the columns, and a 0.1 M triethyl ammonium acetate (TEAA) buffer (pH 7.0) and 0.1 M TEAA buffer:acetonitrile=1:1 (v/v) were prepared as the solution A and the solution B, respectively, of the mobile phase. With respect to the concentration of the solution B, a gradient of 6 to 12% (30 minutes) was performed. The analysis was performed at 1 mL/min, and the fractionation was performed at 3 mL/min. The detection UV was at 260 nm.

The nuclease resistance was assessed in the following manner. To Tris-hydrochloric acid buffers (50 mM, pH 8.0, 100 μL) containing the various types of oligonucleotides respectively (final concentration 4 μM) and magnesium chloride (final concentration 10 mM) was added 3'-exonuclease (*Crotalus Admanteus* Venom Phosphodiesterase: CAVP manufactured by Pharmacia Biotech) to a concentration of 1 μg/mL, and the mixtures were allowed to stand at 37° C. At 2.5, 5, 10, 20, 40, and 80 minutes after the start of the reaction, a 20-μL aliquot was taken from each reaction solution and allowed to stand at 90° C. for 2.5 minutes to thereby inactivate the enzyme, and the remaining amount of the raw material oligonucleotides was quantified by reverse-phase HPLC. The conditions for the HPLC were as follows. Waters Xbridge (registered trademark) MS $C_{18}$ columns 2.5 μmol (4.6 mm×50 mm) were used as the columns. A 0.1 M triethyl ammonium acetate (TEAA) buffer (pH 7.0) and 0.1 M TEAA buffer:acetonitrile=1:1 (v/v) were prepared as the solution A and the solution B, respectively, of the mobile phase, and the HPLC was performed using a gradient of the solution B concentration from 6 to 12% (20 minutes). Analysis was performed at a flow rate of 1 mL/min with UV detection at 260 nm.

Figure 2:
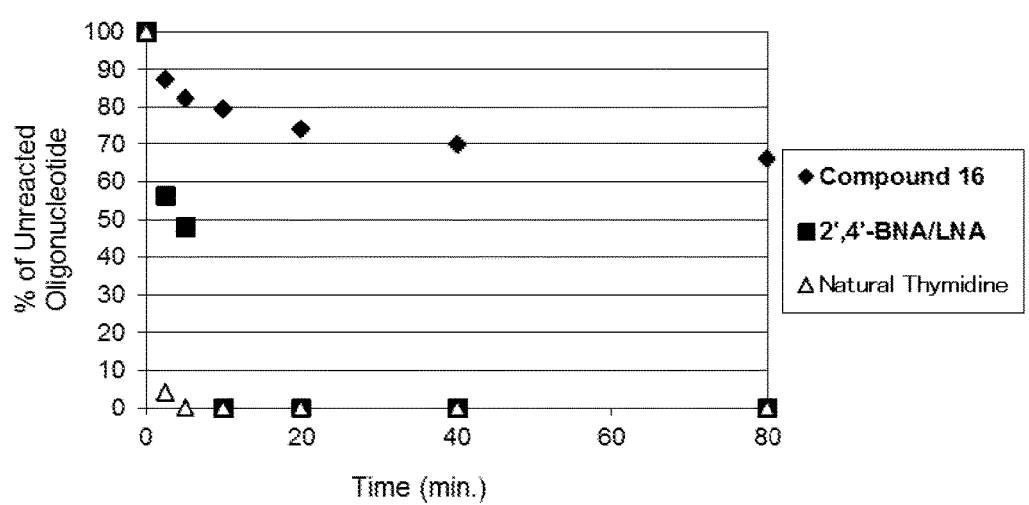
FIG. 2 is a graph illustrating changes in the proportion of unreacted oligonucleotides over time when various types of oligonucleotides having the sequence of 5'-d(TTTTTTTTXT)-3' have been treated with 3'-exonuclease.

The remaining amount of 10-mer and 9-mer oligonucleotides was calculated as the proportion (%) of unreacted oligonucleotides and plotted against the reaction time. FIG. 2 shows the results.

FIG. 2 is a graph illustrating changes in the proportion of unreacted oligonucleotides over time when the various types of oligonucleotides having the sequence of 5'-d(TTTTTTTTXT)-3' were treated with 3'-exonuclease. In FIG. 1, the vertical axis indicates the proportion (%) of oligonucleotides unreacted in the nuclease treatment, and the horizontal axis indicates the nuclease treatment time (min).

Symbols in FIG. 2 indicate the following: rhombuses, oligonucleotides containing compound 16 (amidite block) of Example 1; squares, oligonucleotides containing 2',4'-BNA/LNA; and triangles, oligonucleotides containing natural thymidine.

As is clear from FIG. 2, the oligonucleotides containing compound 16 (amidite block) were not readily degraded, with 60% or more remaining unreacted even at 80 minutes after the nuclease treatment. In contrast, the oligonucleotides containing 2',4'-BNA/LNA and the oligonucleotides containing natural thymidine were almost completely degraded at 20 minutes after the nuclease treatment. Thus, it was shown that the oligonucleotides containing compound 16 (amidite block) have much higher enzyme-resistant ability than the oligonucleotides containing 2',4'-BNA/LNA.

Example 6

Synthesis of 2',4'-Bridged Nucleoside (2): Synthesis of Spirocyclopropane BNA-$^m$C (scpBNA-$^m$C) Amidite Block

[Chemical 27]

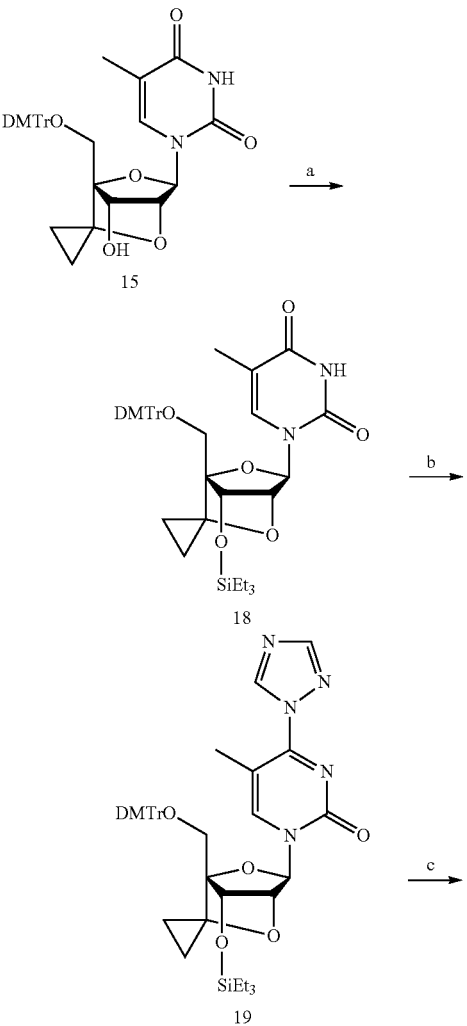

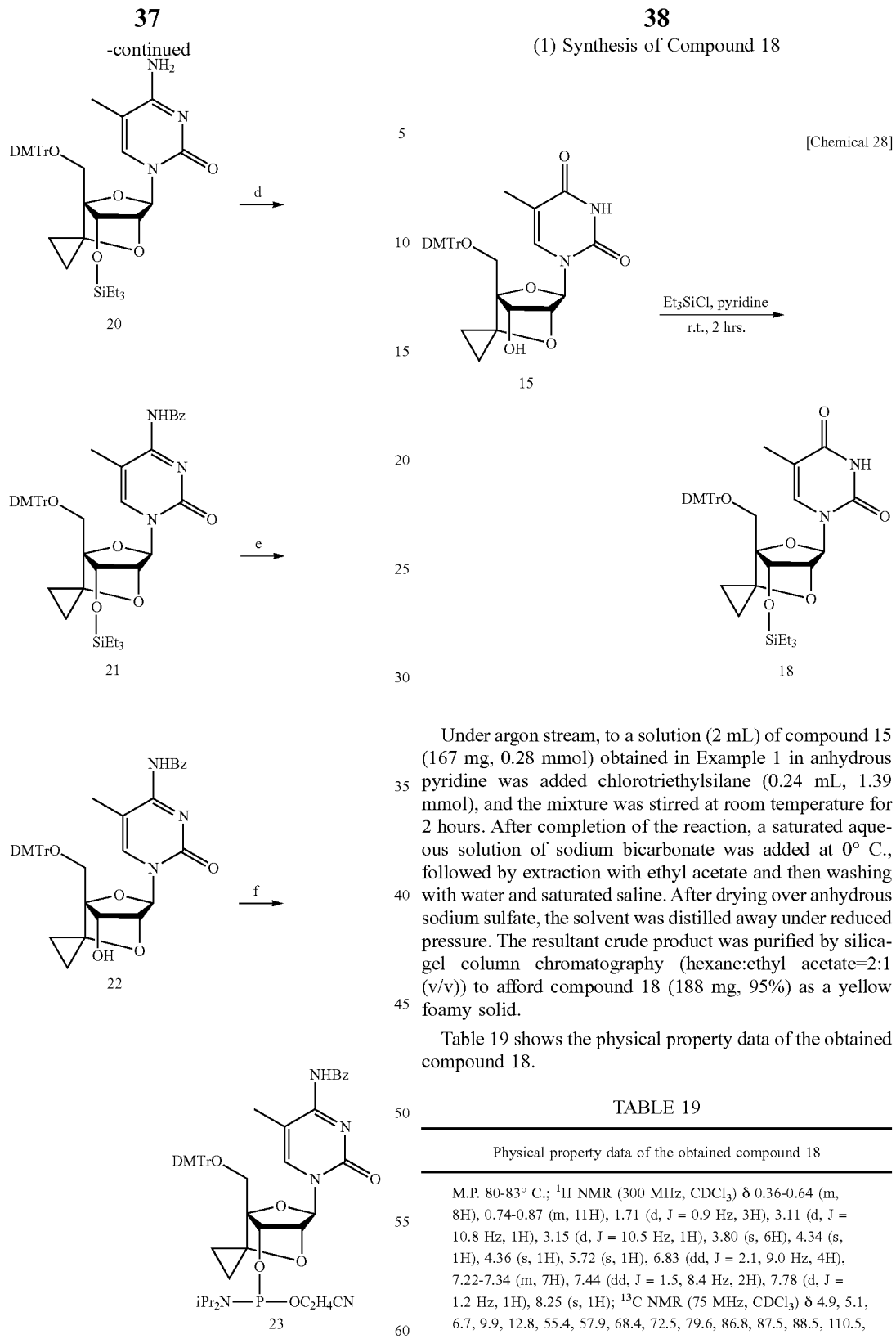

(1) Synthesis of Compound 18

[Chemical 28]

Under argon stream, to a solution (2 mL) of compound 15 (167 mg, 0.28 mmol) obtained in Example 1 in anhydrous pyridine was added chlorotriethylsilane (0.24 mL, 1.39 mmol), and the mixture was stirred at room temperature for 2 hours. After completion of the reaction, a saturated aqueous solution of sodium bicarbonate was added at 0° C., followed by extraction with ethyl acetate and then washing with water and saturated saline. After drying over anhydrous sodium sulfate, the solvent was distilled away under reduced pressure. The resultant crude product was purified by silica-gel column chromatography (hexane:ethyl acetate=2:1 (v/v)) to afford compound 18 (188 mg, 95%) as a yellow foamy solid.

Table 19 shows the physical property data of the obtained compound 18.

TABLE 19

Physical property data of the obtained compound 18

M.P. 80-83° C.; $^1$H NMR (300 MHz, CDCl$_3$) δ 0.36-0.64 (m, 8H), 0.74-0.87 (m, 11H), 1.71 (d, J = 0.9 Hz, 3H), 3.11 (d, J = 10.8 Hz, 1H), 3.15 (d, J = 10.5 Hz, 1H), 3.80 (s, 6H), 4.34 (s, 1H), 4.36 (s, 1H), 5.72 (s, 1H), 6.83 (dd, J = 2.1, 9.0 Hz, 4H), 7.22-7.34 (m, 7H), 7.44 (dd, J = 1.5, 8.4 Hz, 2H), 7.78 (d, J = 1.2 Hz, 1H), 8.25 (s, 1H); $^{13}$C NMR (75 MHz, CDCl$_3$) δ 4.9, 5.1, 6.7, 9.9, 12.8, 55.4, 57.9, 68.4, 72.5, 79.6, 86.8, 87.5, 88.5, 110.5, 113.4, 113.4, 127.2, 128.1, 128.2, 130.1, 130.2, 135.0, 135.4, 135.5, 144.4, 150.0, 158.8, 164.2; IR (KBr): 3166, 3036, 2954, 2876, 1691, 1509, 1254, 1177, 1054, 835, 734 cm$^{-1}$; $[\alpha]_D^{24}$ −13.6 (c 1.01, MeOH); HRMS (MALDI) Calculated for C$_{40}$H$_{48}$N$_2$O$_8$NaSi: 735.3058, Found: 735.3072.

Reagents and conditions under each step:
a Et$_3$SiCl, pyridine, r.t., 2 hrs., 95%;
b 1,2,4-triazole, POCl$_3$, Et$_3$N, MeCN, r.t., 2 hrs., 77%;
c NH$_3$aq, 1,4-dioxane, r.t., 2 hrs., 98% (2 steps);
d BzCl, pyridine, r.t., 3 hrs., 83%;
e TBAF, THF, r.t., 10 mins., 88%;
f iPr$_2$NP(Cl)OCH$_2$CH$_2$CN, DIPEA, MeCN, r.t., 2 hrs., 78%.

(2) Synthesis of Compound 19

[Chemical 29]

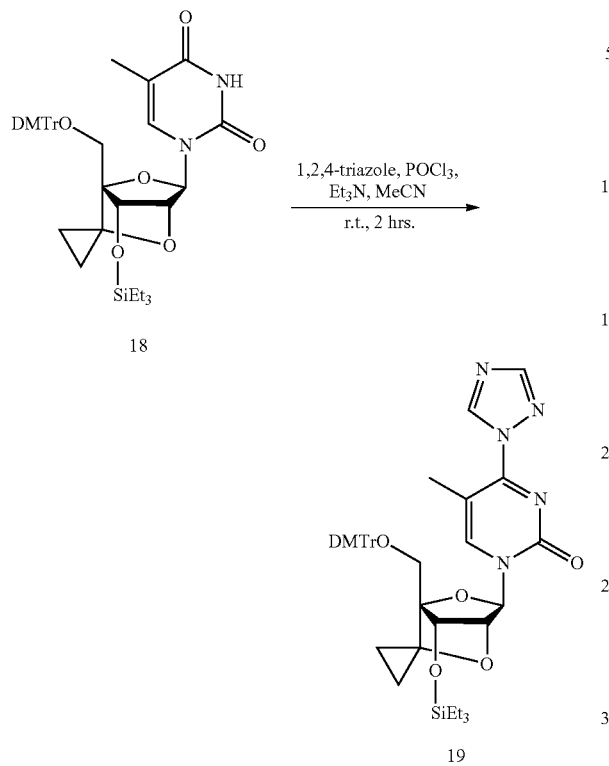

Under argon stream, to a solution (15 mL) of compound 18 (969 mg, 1.36 mmol), triethylamine (2.79 mL, 20.1 mmol), and 1,2,4-triazole (1.39 g, 20.1 mmol) in anhydrous acetonitrile was added dropwise phosphoryl chloride (0.38 mL, 4.03 mmol) at 0° C. After the mixture was stirred at room temperature for 2 hours, to the reaction solution was added a saturated aqueous solution of sodium bicarbonate, followed by extraction with ethyl acetate and then washing with water and saturated saline. After drying over anhydrous sodium sulfate, the solvent was distilled away under reduced pressure to afford compound 19 (1.06 g, 77%). Compound 19 was immediately used for the next reaction without purification.

(3) Synthesis of Compound 20

[Chemical 30]

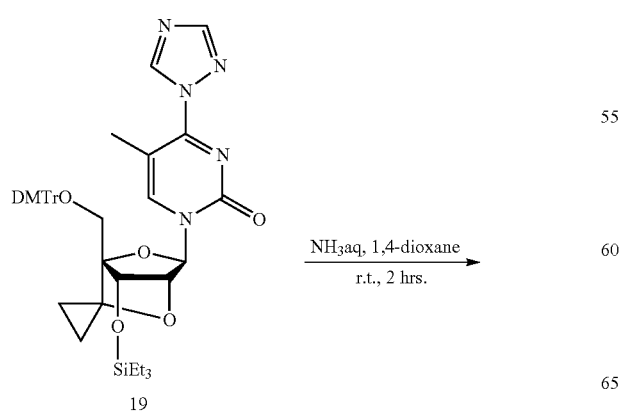

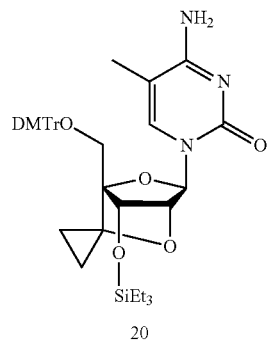

To a solution (10 mL) of compound 19 (1.06 g) in 1,4-dioxane was added an aqueous solution of ammonia (28 wt %, 1.26 mL, 67.0 mmol) at 0° C., and the mixture was stirred at room temperature for 2 hours. After completion of the reaction, the solvent was distilled away under reduced pressure. The resultant crude product was purified by silica-gel column chromatography (chloroform:methanol=30:1 (v/v)) to afford compound 20 (958 mg, 98%, 2 steps) as a white foamy solid.

Table 20 shows the physical property data of the obtained compound 20.

TABLE 20

Physical property data of the obtained compound 20

M.P. 74-77° C.; $^1$H NMR (300 MHz, CDCl$_3$) δ 0.34-0.64 (m, 8H), 0.74-0.85 (m, 11H), 1.76 (s, 3H), 3.13 (d, J = 10.5 Hz, 1H), 3.15 (d, J = 10.2 Hz, 1H), 3.80 (s, 6H), 4.33 (s, 1H), 4.47 (s, 1H), 5.81 (s, 1H), 6.84 (dd, J = 2.7, 9.3 Hz, 4H), 7.22-7.36 (m, 7H), 7.46 (dd, J = 1.5, 8.4 Hz, 2H), 7.86 (s, 1H), 8.20 (s, 2H); $^{13}$C NMR (75 MHz, CDCl$_3$) δ 4.9, 5.1, 6.7, 9.8, 13.5, 55.4, 58.0, 68.3, 72.3, 79.6, 86.7, 88.0, 88.1, 102.4, 113.3, 113.4, 127.2, 128.1, 128.2, 130.1, 130.3, 135.4, 135.6, 137.6, 144.5, 156.2, 158.8, 166.3; IR (KBr): 3351, 3085, 2954, 2876, 1661, 1607, 1509, 1253, 1177, 1045, 832, 738 cm$^{-1}$; $[\alpha]_D^{28}$ −0.4 (c 1.00, MeOH); HRMS (MALDI) Calculated for C$_{40}$H$_{49}$N$_3$O$_7$NaSi: 734.3238, Found: 734.3232.

(4) Synthesis of Compound 21

[Chemical 31]

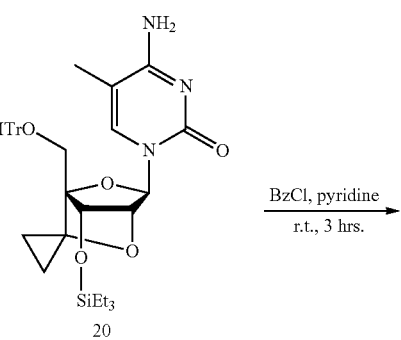

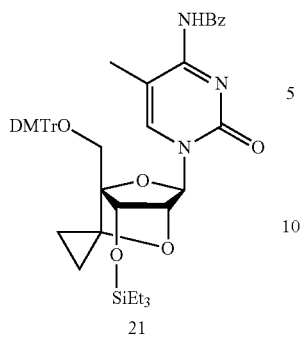

21

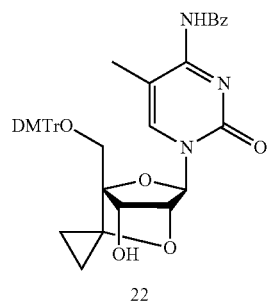

22

Under argon stream, to a solution (13 mL) of compound 20 (902 mg, 1.27 mmol) in anhydrous pyridine was added benzoyl chloride (0.22 mL, 1.90 mmol) at 0° C., and the mixture was stirred at room temperature for 3 hours. After completion of the reaction, a saturated aqueous solution of sodium bicarbonate was added, followed by extraction with ethyl acetate and then washing with water and saturated saline. After drying over anhydrous sodium sulfate, the solvent was distilled away under reduced pressure. The resultant crude product was purified by silica-gel column chromatography (hexane:ethyl acetate=5:1 (v/v)) to afford compound 21 (861 mg, 83%) as a yellow foamy solid.

Table 21 shows the physical property data of the obtained compound 21.

TABLE 21

Physical property data of the obtained compound 21

M.P. 81-84° C.; $^1$H NMR (300 MHz, CDCl$_3$) δ 0.40-0.60 (m, 8H), 0.79-0.87 (m, 11H), 1.91 (d, J = 0.9 Hz, 3H), 3.14 (d, J = 12.0 Hz, 1H), 3.16 (d, J = 10.5 Hz, 1H), 3.81 (s, 6H), 4.36 (s, 1H), 4.42 (s, 1H), 5.77 (s, 1H), 6.83-6.87 (m, 4H), 7.26-7.36 (m, 7H), 7.42-7.54 (m, 5H), 7.96 (d, J = 0.9 Hz, 1H), 8.33 (dd, J = 1.8, 8.4 Hz, 2H); $^{13}$C NMR (75 MHz, CDCl$_3$) δ 4.9, 5.1, 6.7, 9.9, 13.9, 55.4, 57.8, 68.4, 72.3, 79.4, 86.8, 87.8, 88.6, 111.6, 113.4, 113.4, 127.2, 128.1, 128.2, 128.3, 130.0, 130.1, 130.2, 132.6, 135.3, 135.4, 136.2, 137.3, 144.5, 147.7, 158.9, 160.0, 179.7; IR (KBr): 3071, 2954, 2875, 1703, 1570, 1509, 1251, 1176, 1051, 832, 735 cm$^{-1}$; $[\alpha]_D^{25}$ +47.4 (c 1.00, CHCl$_3$); HRMS (MALDI) Calculated for C$_{47}$H$_{53}$N$_3$O$_8$NaSi: 838.3497, Found: 838.3494.

(5) Synthesis of Compound 22

To a solution (8 mL) of compound 21 (701 mg, 0.86 mmol) in tetrahydrofuran was added tetrabutylammonium fluoride (1 M tetrahydrofuran solution, 2.58 mL, 2.58 mmol) at 0° C., and the mixture was stirred at room temperature for 10 minutes. After completion of the reaction, the solvent was distilled away under reduced pressure. The resultant crude product was purified by silica-gel column chromatography (hexane:ethyl acetate=2:1 (v/v)) to afford compound 22 (528 mg, 88%) as a white foamy solid.

Table 22 shows the physical property data of the obtained compound 22.

TABLE 22

Physical property data of the obtained compound 22

M.P. 113-115° C.; $^1$H NMR (300 MHz, CDCl$_3$) δ 0.51-0.54 (m, 1 H), 0.75-0.94 (m, 3H), 1.92 (s, 3H), 2.03 (d, J = 9.9 Hz, 1H), 3.18 (d, J = 11.1 Hz, 1H), 3.34 (d, J = 10.8 Hz, 1H), 3.81 (s, 6 H), 4.32 (d, J = 9.9 Hz, 1H), 4.48 (s, 1H), 5.82 (s, 1H), 6.86 (d, J = 8.7 Hz, 4H), 7.26-7.56 (m, 12H), 7.83 (s, 1H), 8.32 (d, J = 6.6 Hz, 1H); $^{13}$C NMR (75 MHz, CDCl$_3$) δ 5.3, 9.7, 13.9, 55.4, 57.9, 67.9, 72.6, 79.5, 87.0, 87.1, 88.2, 111.8, 113.5, 127.3, 128.1, 128.2, 128.3, 130.0, 130.2, 130.2, 132.6, 135.3, 135.4, 136.0, 137.2, 144.4, 147.7, 158.8, 159.9, 179.7; IR (KBr): 3068, 2955, 2836, 1702, 1568, 1508, 1251, 1176, 1047, 834, 714 cm$^{-1}$; $[\alpha]_D^{25}$ +34.5 (c 0.99, MeOH); HRMS (MALDI) Calculated for C$_{41}$H$_{39}$N$_3$O$_8$Na: 724.2634, Found: 724.2629.

(6) Synthesis of Compound 23

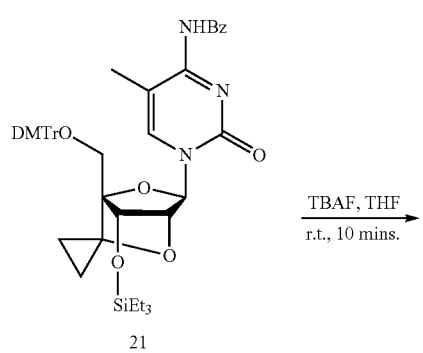

[Chemical 32]

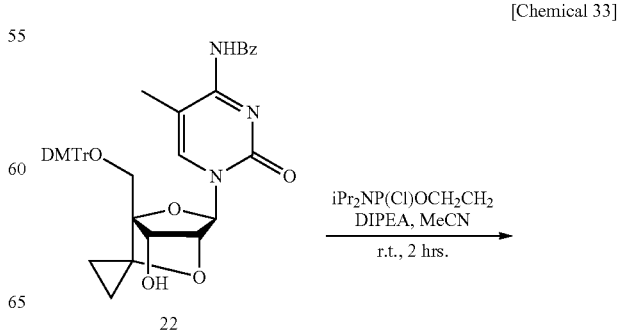

[Chemical 33]

-continued

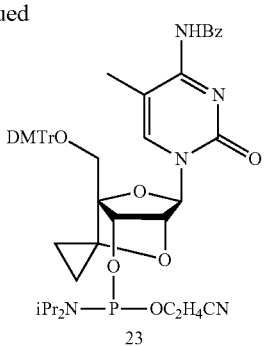

Under argon stream, to a solution (7 mL) of compound 22 (528 mg, 0.75 mmol) in anhydrous acetonitrile were added N,N-diisopropylethylamine (0.39 mL, 2.26 mmol) and 2-cyanoethyl-N,N-diisopropyl phosphorochloridate (0.25 mL, 1.13 mmol) at 0° C., and the mixture was stirred at room temperature for 2 hours. After completion of the reaction, a saturated aqueous solution of sodium bicarbonate was added, followed by extraction with ethyl acetate and then washing with water and saturated saline. After drying over anhydrous sodium sulfate, the solvent was distilled away under reduced pressure. The resultant crude product was purified by silica-gel column chromatography (0.5% triethylamine-containing hexane:ethyl acetate=2:1 (v/v)) to afford compound 23 (529 mg, 78%: scpBNA-$^m$C amidite block) as a white foamy solid.

Table 23 shows the physical property data of the obtained compound 23.

TABLE 23

Physical property data of the obtained compound 23

$^1$H NMR (300 MHz, CDCl$_3$) δ 0.39-0.43 (m, 1H), 0.71-0.88 (m, 3H), 0.98 (d, J = 6.6 Hz, 3H), 1.07 (d, J = 6.6 Hz, 3H), 1.11 (d, J = 6.9 Hz, 3H), 1.14 (d, J = 6.9 Hz, 3H), 1.86 (s, 3/2H), 1.88 (s, 3/2H), 2.36-2.40 (m, 1H), 2.52-2.57 (m, 1H), 3.17-3.31 (m, 2H), 3.49-3.57 (m, 3H), 3.64-3.77 (m, 1H), 3.81 (s, 3H), 3.81 (s, 3H), 4.40 (d, J = 6.6 Hz, 1/2H), 4.44 (d, J = 9.0 Hz, 1/2 H), 4.65 (s, 1/2H), 4.69 (s, 1/2H), 5.82 (s, 1H), 6.82-6.89 (m, 4 H), 7.25-7.52 (m, 12H), 7.88 (s, 1/2H), 7.91 (s, 1/2H), 8.33 (d, J = 6.9 Hz, 2H); $^{31}$P NMR (121 MHz, CDCl$_3$) δ 148.8, 148.9; HRMS (MALDI) Calculated for C$_{50}$H$_{56}$N$_5$O$_9$NaP: 924.3722, Found: 924.3708.

Example 7

Animal Experiment (1) Design and Synthesis of Oligonucleotides for Animal Experiment As a target gene, mouse phosphatase and tensin homolog (Pten) mRNA was selected (NCBI Reference Number: NM_008960.2), and an oligonucleotide complementary to a sequence from the 60th to the 73th base of the complete 8229 bases was synthesized. It should be noted that with respect to the sequence, a reported sequence was used (Molecular Therapy—Nucleic Acids, 2012, 1, e47).

With regard to the synthesis of oligonucleotides, first, for comparison, a 2',4'-BNA/LNA-incorporated oligonucleotide (oligonucleotide 1) as shown in Table 24 was produced in which all of the linkages were phosphorothioated. On the other hand, a scpBNA-incorporated oligonucleotide (oligonucleotide 2) was produced using the scpBNA-T amidite block (compound 16) obtained in Example 1 and the scpBNA-$^m$C amidite block (compound 23) obtained in Example 6. These oligonucleotides were produced through custom synthesis by GeneDesign, Inc. The produced oligonucleotides were endotoxin-free, in vivo-grade oligonucleotides that were in sodium form.

(2) Determination of the Melting Temperature ($T_m$)

The binding affinities of oligonucleotides 1 and 2 above for a complementary strand RNA (5'-agcugcagccauga-3' (SEQ ID NO: 2)) were assessed in the following manner.

Oligonucleotide 1 and oligonucleotide 2 were added separately to a phosphate buffer (10 mM NaH$_2$PO$_4$.10 mM Na$_2$HPO$_4$, 100 mM NaCl, pH 7.0) to a final concentration of 2 µM to prepare respective oligonucleotide solutions. With respect to each of the prepared solutions, the temperature was raised at the rate of 0.5° C./min within a temperature range of 4° C. to 95° C. while absorbance at 260 nm was monitored. The $T_m$ value was calculated using a median method, and a mean value of three independent measurements was adopted. Table 24 shows the results together with the results of mass spectrometry of oligonucleotides 1 and 2.

TABLE 24

| | | MALDI-TOF-MS[c] | | $T_m$ |
|---|---|---|---|---|
| | Sequences (5'--->3')[a,b] | Calcd. [M-H]$^-$ | Found [M-H]$^-$ | value (° C.) |
| Oligo-nucleo-tide 1 | T$^m$Catggctgcag$^m$CT | 4603.79 | 4604.40 | 63.0 |
| Oligo-nucleo-tide 2 | T$^m$<u>C</u>atggctgcag<u>$^m$C</u><u>T</u> | 4707.97 | 4707.44 | 62.4 |

[a]All linkages were phosphorothioated.
[b]Each case was indicated as follows: lower case, DNA; upper case, 2',4'-BNA/LNA; underlined upper case, scpBNA.
[c]Each oligonucleotide was identified by MALDI-TOF-MS, and was analyzed by GeneDesign, Inc.

As shown in Table 24, there was no significant difference between the $T_m$ values of oligonucleotide 1 (2',4'-BNA/LNA-incorporated oligonucleotide) and oligonucleotide 2 (scpBNA-incorporated oligonucleotide), and it can be seen that the binding affinities of oligonucleotides 1 and 2 were almost equivalent to each other.

(3) Administration Experiment

Seven-week-old mice C$_{57}$BL/6J (male) (Japan SLC, Inc.) were purchased as subjects and acclimated for 1 week. Then, oligonucleotide 1 (35 mg/kg) or oligonucleotide 2 (35 mg/kg) dissolved in physiological saline, or physiological saline was administered to these mice by intraperitoneal injection at a total dose of 200 µL (administered group N=4). After 72 hours, the mice were dissected under anesthesia with isoflurane. Blood was collected from the inferior vena cava, and then heart perfusion was performed with PBS. After that, the livers were extirpated and stored in RNA later (registered trademark) Stabilization Solution (Thermo Fisher Scientific, AM7021) at 4° C.

Next, sections were taken from the preserved livers above, to which 500 µL of LRT (containing 2-mercaptoethanol) of a QuickGene RNA tissue kit SII (RT-S2 manufactured by Wako Pure Chemical Industries, Ltd.) was added. A single stainless steel bead was placed in the mixture, and the mixture was homogenized (µT-12 manufactured by TAITEC, rotation speed: 2,000 rpm, 3 minutes). After that, the mixture was centrifuged at room temperature at 12,000 rpm for 3 minutes, and 385 μL of the supernatant was collected. To the supernatant was added 175 μL of SRT of the kit, and the mixture was vortexed for 15 seconds and then spinned down. After that, 140 μL of special grade ethanol was added, and the mixture was further vortexed for 1 minute and then spinned down. The whole amount of the thus obtained mixture was placed in an automated RNA extractor (QuickGene-800 manufactured by Wako Pure Chemical Industries, Ltd.), and total RNA was extracted.

Next, reverse transcription of 2 μg of total RNA was performed. A High Capacity cDNA Reverse Transcription Kit (Thermo Fisher Scientific, 4368813) was used, and cDNA was produced according to the protocol of this kit.

Then, cDNA above was diluted 30-fold to prepare a cDNA solution, which was subjected to real-time PCR for the target gene Pten. With regard to analysis of the expression level of Pten, the Pten expression level relative to the expression level of the housekeeping gene Gapdh was assessed. This reaction was performed using a TaqMan (registered trademark) Fast Universal PCR Master Mix (Thermo Fisher Scientific, 4352042) and a TaqMan probe (Thermo Fisher Scientific, Pten: Mm00477208_m1, Gapdh: Mm99999915_g1) according to the protocols of these products.

Furthermore, serum was separated from the blood samples collected from the inferior vena cava of the mice above in the following manner.

The collected blood samples were each added into a tube (BD,365967) containing a blood coagulation accelerator and a serum separator, and centrifugation was performed at 5,000 rpm for 20 minutes at 4° C. Serum was collected and used for the subsequent blood test.

With respect to the collected serum, the GOT (AST) value and the GPT (ALT) value, which are indices of hepatotoxicity, were calculated using a Transaminase CII-Test Wako (431-30901 manufactured by Wako Pure Chemical Industries, Ltd.). Equal amounts of a substrate enzyme solution and a coloring reagent were mixed to form a substrate coloring solution. Then, 100 μL of the substrate coloring solution was dispensed into a 96-well plate, which was then heated at 37° C. for 5 minutes. After that, 2 μL of the serum obtained above was added to the coloring solution, followed by heating at 37° C. for 20 minutes. Then, 200 μL of a quenching solution was added, and absorbance at 555 nm was measured using a plate reader (SpectraMax M5e manufactured by Molecular Devices). The AST/ALT values were calculated from the obtained absorbance using a calibration curve method according to the protocol included in the product.

Figure 3:
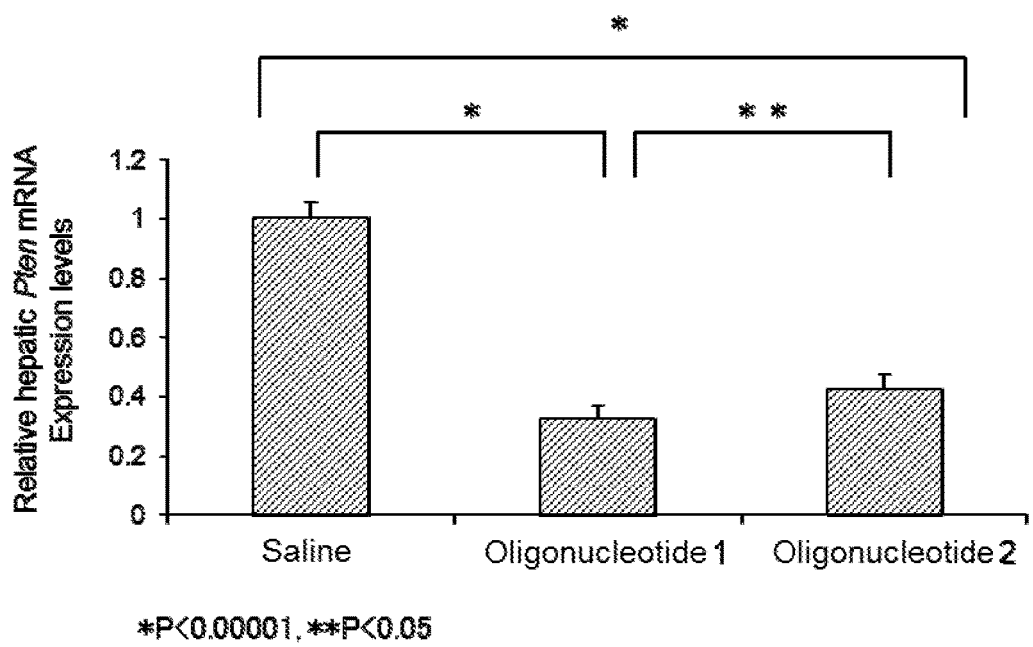
FIG. 3 is a graph illustrating the results, with respect to knockdown efficiency of target mRNA, of in vivo administration of oligonucleotides to mice in Example 7.
Figure 4:
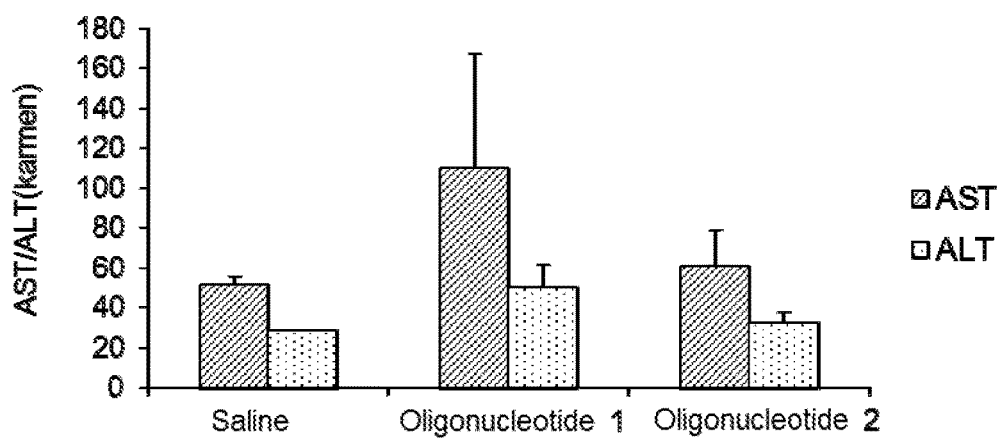
FIG. 4 is a graph illustrating the results, with respect to hematotoxicity, of the in vivo administration of the oligonucleotides to the mice in Example 7.

FIGS. 3 and 4 show the results.

As shown in FIG. 3, quantification of the expression level of Pten mRNA expressed in the liver showed high knockdown efficiencies (60% to 70%) both in the oligonucleotide 1-administered group and in the oligonucleotide 2-administered group, and it was thus found that the scpBNA-incorporated oligonucleotide (oligonucleotide 2) exhibited an antisense activity equivalent to that of the 2',4'-LNA/BNA-incorporated oligonucleotides (oligonucleotide 1).

In contrast, as shown in FIG. 4, in the group to which the 2',4'-LNA/BNA-incorporated oligonucleotide (oligonucleotide 1) was administered, the AST/ALT value exceeded 100/30 Karmen, and toxicity was observed. In the group to which the scpBNA-incorporated oligonucleotide (oligonucleotide 2) was administered, the AST/ALT value was reduced to about half that in the oligonucleotide 1-administered group, and hematotoxicity was not observed.

Example 8

Assessment In Vitro Antisense Activity (1) Introduction of Antisense Nucleic Acid into Cell and Production of Cell Lysate A mouse liver cancer-derived cell line NMuLi was seeded into a 96-well plate at a density of $2.5 \times 10^3$ cells/well and cultured for 24 hours. Oligonucleotide 1 or 2 obtained in Example 7 was complexed with Lipofectamine 2000 in Opti-MEM according to the protocol supplied with the plate, and 50 μL of the resultant complex was added to 100 μL of 10% FBS/DMEM (containing no antibiotic) in each well. After 24 hours, the culture medium was removed from the wells. After washing with PBS, a mixed solution (SuperPrep™, manufactured by Toyobo Co., Ltd., SCQ-101) of 49.7 μL of Lysis Solution and 0.3 μL of gDNA Remover was added at 50 μL/well, followed by gentle shaking, and then incubation was performed for 5 minutes at room temperature. Then, a mixed solution (SuperPrep™, manufactured by Toyobo Co., Ltd., SCQ-101) of 9.5 μL of Stop Solution and 0.5 μL of RNase Inhibitor was added at 10 μL/well, followed by gentle shaking, and then incubation was performed for 2 minutes at room temperature to afford a cell lysate.

After that, 8 μL of the cell lysate prepared above was added to 32 μL of a mixed solution (SuperPrep™, manufactured by Toyobo Co., Ltd., SCQ-101) of 8 μL of 5×RT Master Mix and 24 μL of Nuclease-free Water. Reverse transcription was performed by applying temperatures in the order of 37° C. for 15 minutes→50° C. for 5 minutes→98° C. for 5 minutes→4° C. for 10 minutes to produce a cDNA solution. Next, the obtained cDNA solution was diluted 30-fold, followed by real-time PCR for the target gene Pten. With regard to analysis of the expression level of Pten, the Pten expression level relative to the expression level of the housekeeping gene Gapdh was assessed. The reaction was performed using a TaqMan (registered trademark) Fast Universal PCR Master Mix (Thermo Fisher Scientific, 4352042) and a TaqMan probe (Thermo Fisher Scientific, Pten: Mm00477208_m1, Gapdh: Mm99999915_g1) according to the protocols of these products.

Moreover, the relative remaining amount of Pten mRNA was plotted against the logarithm of concentration, fitting was performed (Sigmoid mode) using a graph software (Igor Pro manufactured by Hulinks Inc.), and $IC_{50}$ was calculated.

Figure 5:
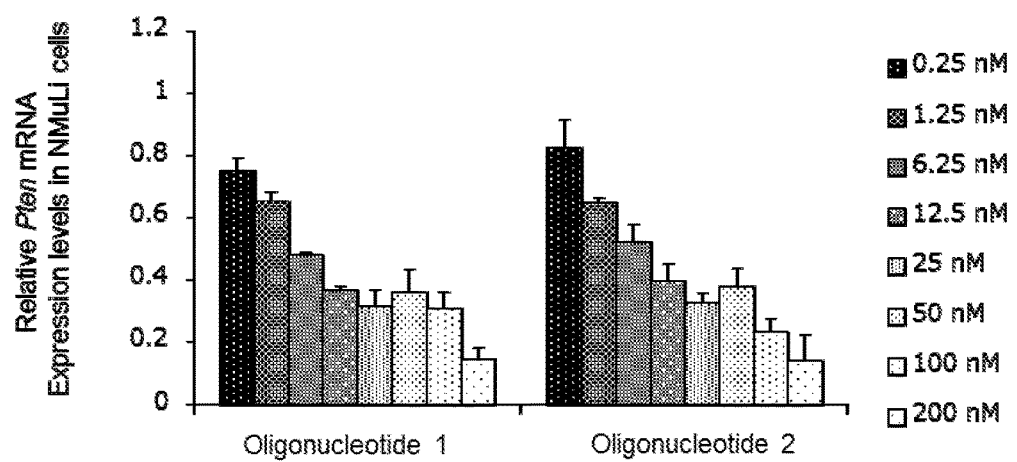
FIG. 5 is a graph illustrating the results with respect to relative expression level of Pten mRNA in NMuLi cells using oligonucleotides at various concentrations in Example 8.

FIG. 5 shows the results of introduction of individual oligonucleotides 1 and 2 to concentrations from 0.25 nM to 200 nM (N=4 for each concentration). Furthermore, Table 25 shows the results with respect to $IC_{50}$ calculated as described above.

TABLE 25

| | Modification | $IC_{50}$ (nM)[a] |
|---|---|---|
| Oligonucleotide 1 | 2',4'-BNA/LNA | 4.8 |
| Oligonucleotide 2 | scpBNA | 6.1 |

[a]$IC_{50}$ for Pten mRNA knockdown after transfection using a lipofection method in NMuLi cells.

As is clear from FIG. 5 and Table 25, it was found that although oligonucleotide 2 showed a slightly higher $IC_{50}$ value than oligonucleotide 1, there was no significant difference in the Pten mRNA expression level in the NMuLi cells between oligonucleotide 1 and oligonucleotide 2. Thus, it was found that even in vitro, the scpBNA-incorporated oligonucleotide (oligonucleotide 2) exhibits an antisense activity equivalent to that of the 2',4'-LNA/BNA-incorporated oligonucleotide (oligonucleotide 1).

Heretofore, many cases have been reported in which when a 2',4'-LNA/BNA-incorporated oligonucleotide retaining a high antisense activity was administered, the oligonucleotide also exhibited a high hematotoxicity value. However, according to the results of Examples 7 and 8 above, when the scpBNA-incorporated oligonucleotide was administered, the oligonucleotide did not develop hematotoxicity while maintaining a high antisense activity, and these results indicate that the oligonucleotides according to the present invention are useful for development of novel bridged artificial nucleic acid analogues for application to nucleic acid drugs.

Example 9

Synthesis of 2',4'-Bridged Nucleoside (3): Synthesis of Spirocyclopropane BNA-A (scpBNA-A) Amidite Block

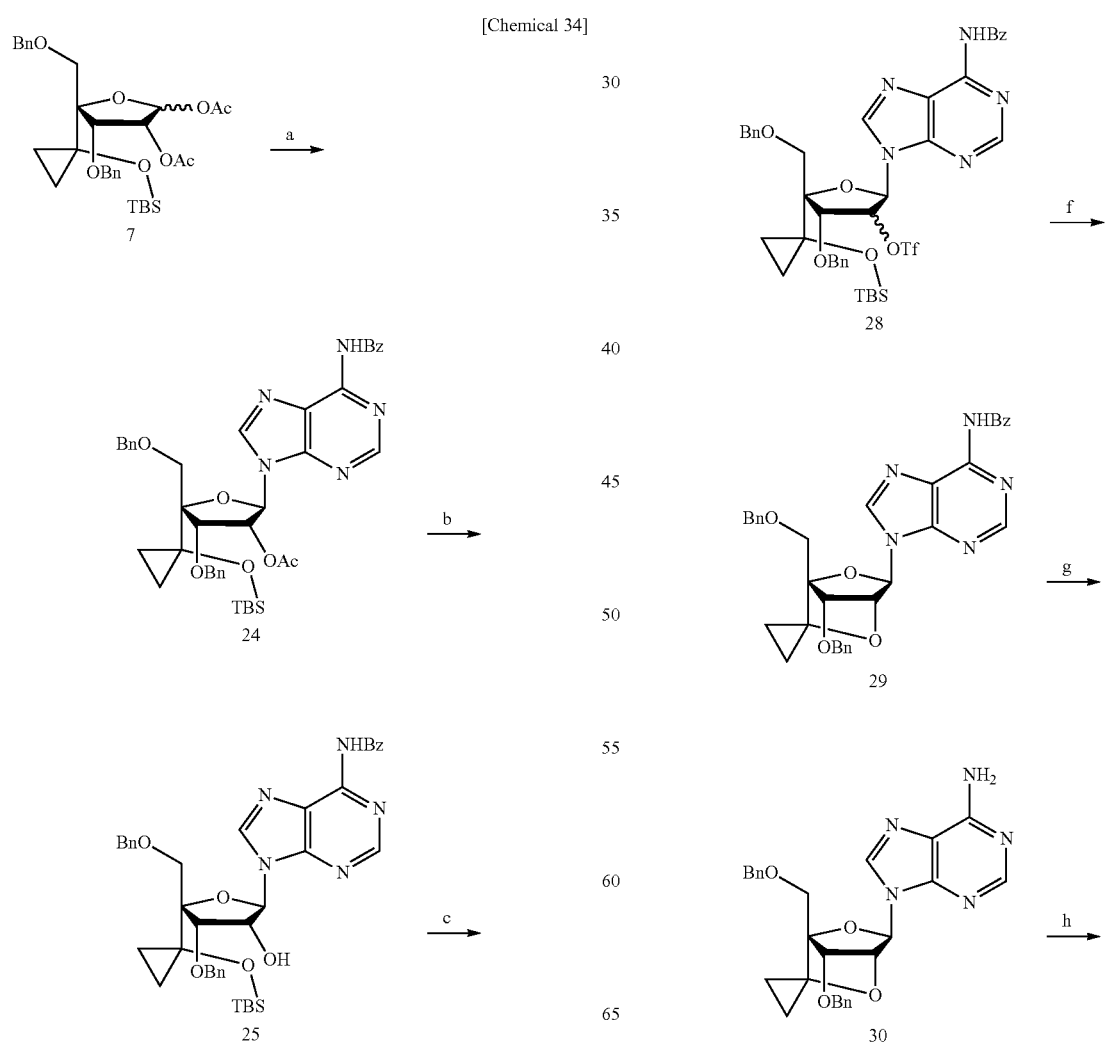

-continued

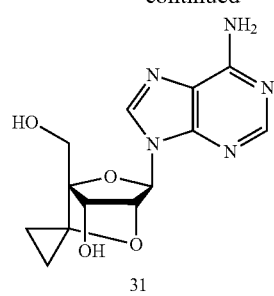

31

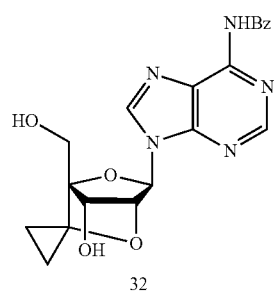

32

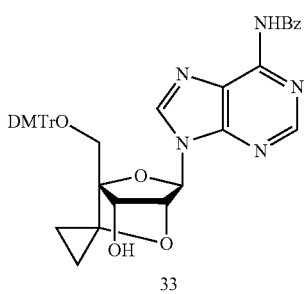

33

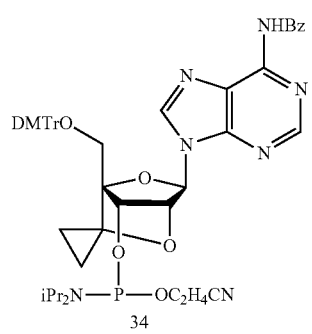

34

Reagents and conditions under each step:
a N⁶-benzoyladenine, BSA, TMSOTf, MeCN, 80° C., 26 hrs., 50% (2 steps);
b K₂CO₃, MeOH, 0° C., 20 mins., 99%;
c AZADOL, PhI(OAc)₂, CH₂Cl₂, r.t., 6 hrs., 89%;
d NaBH₄, EtOH, 0° C., 20 mins., 70% (2 steps, R:S = 2.6:1);
e Tf₂O, DMAP, CH₂Cl₂, r.t., 1 hr.;
f TBAF, THF, r.t., 1 hr., 14% (2 steps);
g MeNH₂aq, THF, r.t., 1 hr., 83%;
h H₂, Pd(OH)₂/C, HCO₂NH₄, EtOH/AcOH, reflux, 5 hrs., 46%;
i (1) TMSCl, pyridine, 0° C., 40 mins., (2) BzCl, r.t., 2 hrs., (3) NH₃aq, 0° C., 3 hrs. 61% (3 steps);
j DMTrCl, pyridine, r.t., 19 hrs., 72%;
k iPr₂NP(Cl)OC₂H₄CN, DIPEA, MeCN, r.t., 4 hrs., 67%.

(1) Synthesis of Compound 24

[Chemical 35]

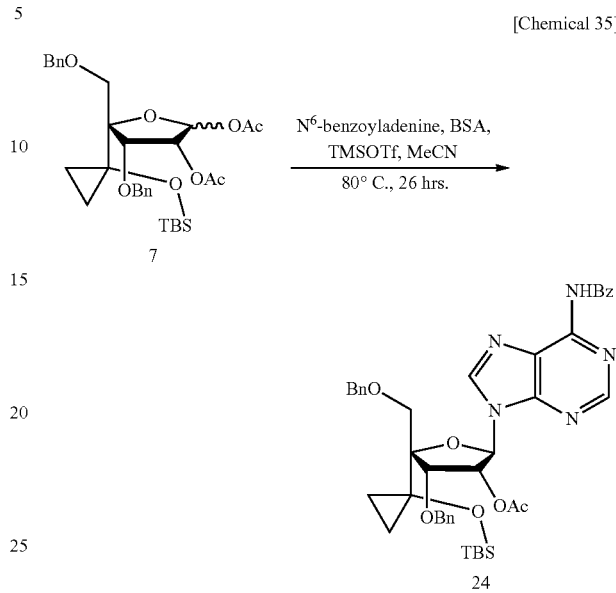

Under nitrogen stream, to a solution of compound 7 (6.14 g) obtained in Example 1 in anhydrous acetonitrile (70 mL) were added N⁶-benzoyladenine (2.58 g, 10.8 mmol) and N,O-bis(trimethylsilyl)acetamide (5.65 mL, 23.1 mmol) at 0° C., and the mixture was stirred for 10 minutes. Then, trimethylsilyl trifluoromethanesulfonate (2.78 mL, 15.4 mmol) was added dropwise at 0° C., and the mixture was stirred at 80° C. for 22 hours. After completion of the reaction, a saturated aqueous solution of sodium bicarbonate was added at 0° C., followed by extraction with ethyl acetate and then washing with water and saturated saline. After drying over anhydrous sodium sulfate, the solvent was distilled away under reduced pressure. The resultant crude product was purified by silica-gel column chromatography (hexane:ethyl acetate=2:1 (v/v)) to afford compound 24 (2.91 g, 50% (2 steps)) as a white foamy solid.

Table 26 shows the physical property data of the obtained compound 24.

TABLE 26

Physical property data of the obtained compound 24

M.P. 70-72° C.; ¹H NMR (300 MHz, CDCl₃) δ 0.00 (s, 6H), 0.65-0.88 (m, 3H), 0.75 (s, 9H), 1.08-1.11 (m, 1H), 1.90 (s, 3H), 3.59 (d, J = 9.9 Hz, 1H), 4.01 (d, J = 9.9 Hz, 1H), 4.45-4.62 (m, 3H), 4.85 (d, J = 12.0 Hz, 1H), 5.00 (d, J = 11.1 Hz, 1H), 5.90 (dd, J = 4.8, 8.4 Hz, 1H), 6.42 (d, J = 8.4 Hz, 1H), 7.30-7.61 (m, 13H), 8.02 (d, J = 7.2 Hz, 2H), 8.51 (s, 1H), 8.78 (s, 1H), 8.99 (s, 1H); IR (KBr): 3062, 3029, 2952, 2930, 2858, 1747, 1609, 1454, 1240, 1072, 836, 700 cm⁻¹; [α]_D²⁷ −48.1 (c 1.02, CHCl₃); HRMS (MALDI) Calculated for C₄₂H₄₉N₅O₇NaSi: 786.3296, Found: 786.3294.

(2) Synthesis of Compound 25

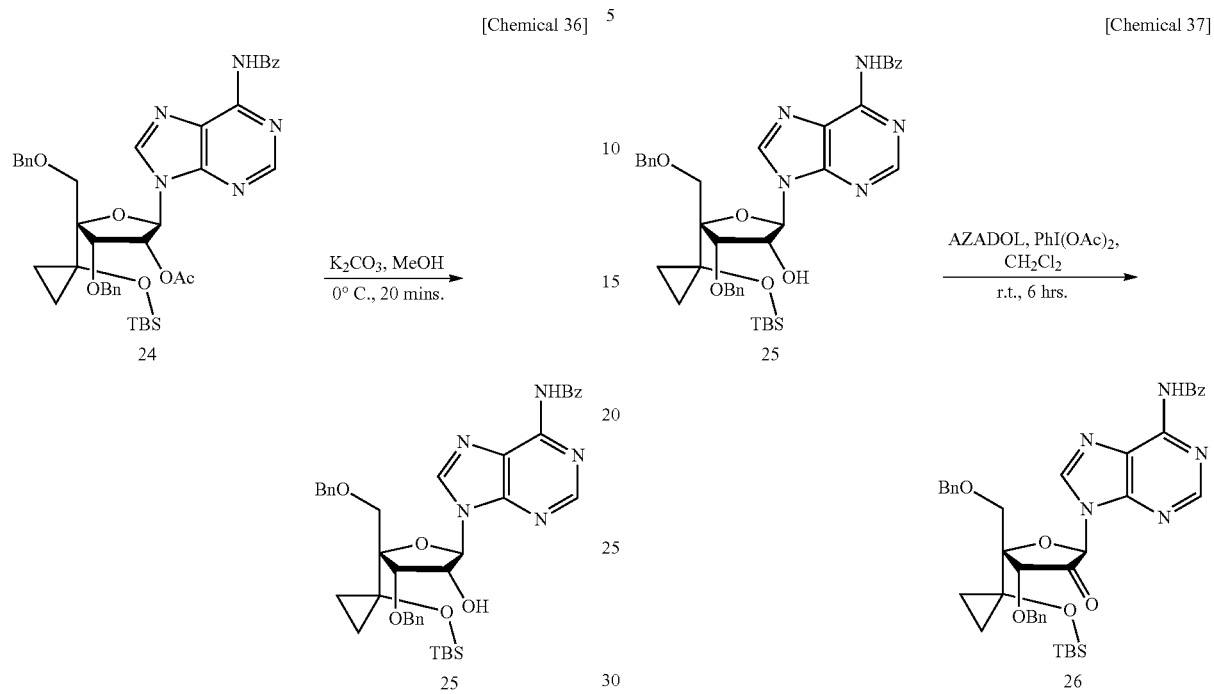

[Chemical 36]

To a solution of compound 24 (2.20 g, 2.88 mmol) in methanol (40 mL) was added potassium carbonate (795 mg, 5.75 mmol), and the mixture was stirred at 0° C. for 20 minutes. After completion of the reaction, water was added at 0° C., followed by extraction with ethyl acetate and then washing with water and saturated saline. After drying over anhydrous sodium sulfate, the solvent was distilled away under reduced pressure. The resultant crude product was purified by silica-gel column chromatography (hexane:ethyl acetate=3:2 (v/v)) to afford compound 25 (2.05 g, 99%) as a white foamy solid.

Table 27 shows the physical property data of the obtained compound 25.

TABLE 27

| Physical property data of the obtained compound 25 |
|---|
| M.P. 80-83° C.; $^1$H NMR (300 MHz, CDCl$_3$) δ 0.03 (s, 6H), 0.69-0.84 (m, 3H), 0.79 (s, 9H), 1.06-1.09 (m, 1H), 3.17 (d, J = 10.8 Hz, 1H), 3.57 (d, J = 10.2 Hz, 1H), 4.01 (d, J = 9.6 Hz, 1H), 4.27 (d, J = 5.1 Hz, 1H), 4.51 (d, J = 11.7 Hz, 1H), 4.58 (d, J = 10.5 Hz, 1H), 4.80 (d, J = 12.0 Hz, 1H), 4.97 (m, 1H), 5.24 (d, J = 10.5 Hz, 1H), 5.99 (d, J = 7.5 Hz, 1H), 7.37-7.39 (m, 10H), 7.49-7.63 (m, 3H), 8.02 (d, J = 7.5 Hz, 2H), 8.46 (s, 1H), 8.76 (s, 1H), 8.98 (s, 1H); $^{13}$C NMR (75 MHz, CDCl$_3$) δ −3.3, −3.0, 7.3, 10.7, 18.0, 25.8, 58.2, 74.1, 75.8, 76.9, 83.1, 88.0, 88.3, 122.9, 128.0, 128.1, 128.2, 128.3, 128.5, 128.7, 128.9, 128.9, 132.8, 133.8, 137.0, 137.9, 141.6, 149.4, 152.5, 152.7, 164.8; IR (KBr): 3328, 3030, 2929, 1615, 1455, 1256, 1069, 836, 730 cm$^{-1}$; [α]$_D^{23}$ −62.5 (c 1.02, CHCl$_3$); HRMS (MALDI) Calculate for C$_{40}$H$_{47}$N$_5$O$_6$NaSi: 744.3186, Found: 744.3188. |

(3) Synthesis of Compound 26

[Chemical 37]

To a solution of compound 25 (1.08 g, 1.50 mmol) in dichloromethane (15 mL) were added diacetoxyiodobenzene (724 mg, 2.25 mmol) and 2-hydroxy-2-azaadamantane (11.5 mg, 0.075 mmol, 5 mol %), and the mixture was stirred at room temperature for 6 hours. After completion of the reaction, a saturated aqueous solution of sodium thiosulfate and a saturated aqueous solution of sodium bicarbonate (2:1 (v/v)) were added, followed by extraction with ethyl acetate and then washing with water and saturated saline. After drying over anhydrous sodium sulfate, the solvent was distilled away under reduced pressure to afford compound 26 (1.08 g) as a yellow foamy solid. Compound 26 was immediately used for the next reaction without purification.

(4) Synthesis of Compound 27

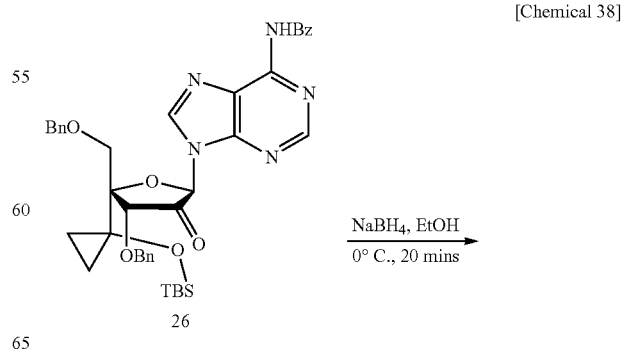

[Chemical 38]

-continued

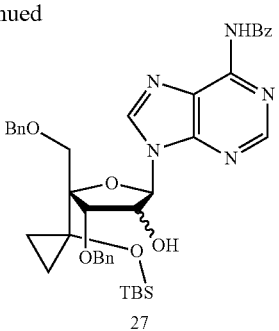

27

To a solution of compound 26 (1.08 g) in ethanol (15 mL) was added sodium borohydride (79.4 mg, 2.10 mmol), and the mixture was stirred at room temperature for 20 minutes. After completion of the reaction, water was added, followed by extraction with ethyl acetate and then washing with saturated saline and water. After drying over anhydrous sodium sulfate, the solvent was distilled away under reduced pressure. The resultant crude product was purified by silica-gel column chromatography (hexane:ethyl acetate=1:1 (v/v)) to afford compound 27 (773 mg, 70%, 2 steps, R:S=2.6:1) as a yellow foamy solid. The obtained compound 27 was a mixture from which it was difficult to separate diastereomers, and thus the mixture was used for the next reaction as is.

(5) Synthesis of Compound 28

[Chemical 39]

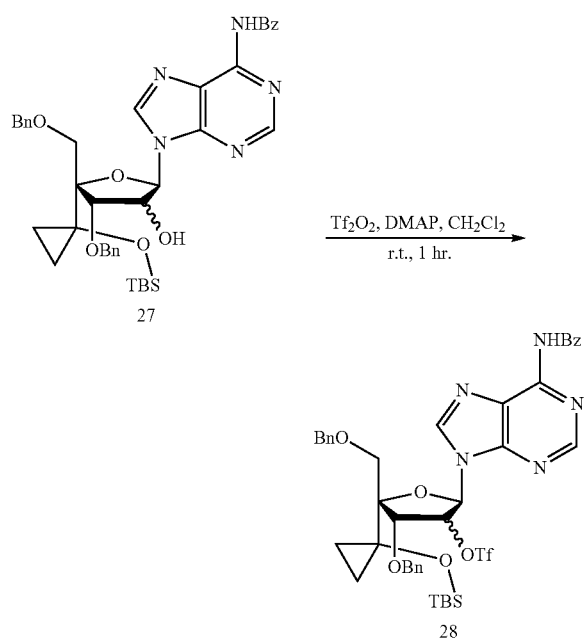

Under nitrogen stream, to a solution of compound 27 (773 mg, 1.07 mmol) in dichloromethane (10 mL) were added 4-dimethylaminopyridine (653 mg, 5.35 mmol) and trifluoromethanesulfonic anhydride (0.22 mL, 1.39 mmol), and the mixture was stirred at room temperature for 1 hour. After completion of the reaction, a saturated aqueous solution of sodium bicarbonate was added, followed by extraction with ethyl acetate and then washing with a saturated aqueous solution of ammonium chloride, water, and saturated saline. After drying over anhydrous sodium sulfate, the solvent was distilled away under reduced pressure to afford compound 28 (869 mg, R:S=2.6:1) as a yellow foamy solid. Compound 28 was immediately used for the next reaction without purification.

(6) Synthesis of Compound 29

[Chemical 40]

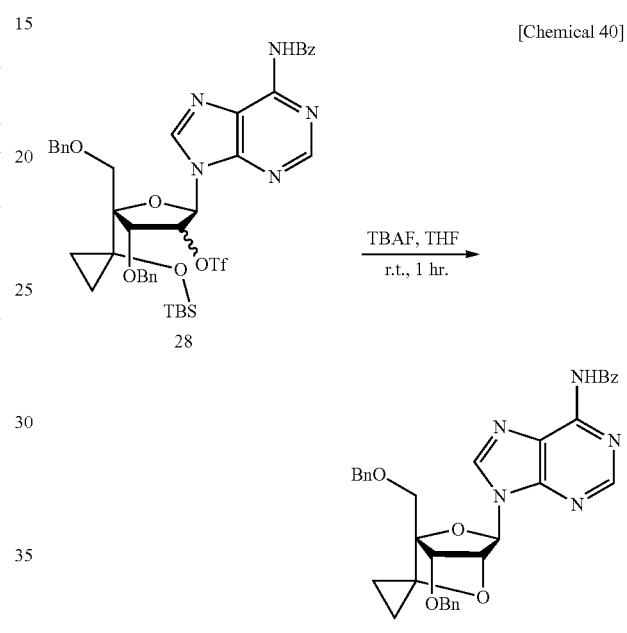

To a solution of compound 28 (869 mg) in tetrahydrofuran (10 mL) was added tetrabutylammonium fluoride (1 M tetrahydrofuran solution, 3.21 mL, 3.21 mmol), and the mixture was stirred at room temperature for 1 hour. After completion of the reaction, the solvent was distilled away under reduced pressure. The resultant crude product was purified by silica-gel column chromatography (hexane:ethyl acetate=1:1 (v/v)) to afford compound 29 (90 mg, 14%, 2 steps) as a white foamy solid.

Table 28 shows the physical property data of the obtained compound 29.

TABLE 28

| Physical property data of the obtained compound 29 |
| --- |
| M.P. 57-59° C.; $^1$H NMR (300 MHz, CDCl$_3$) δ 0.74-0.79 (m, 1H), 0.85-1.03 (m, 3H), 3.56 (d, J = 10.8 Hz, 1H), 3.66 (d, J = 10.8 Hz, 1H), 4.38 (s, 1H), 4.58 (s, 2H), 4.58 (d, J = 12.0 Hz, 1H), 4.66 (d, J = 11.7 Hz, 1H), 4.82 (s, 1H), 6.21 (s, 1H), 7.24-7.38 (m, 10H), 7.52-7.63 (m, 3H), 8.03 (dd, J = 1.2, 6.9 Hz, 2H), 8.26 (s, 1H), 8.76 (s, 1H), 8.93 (s, 1H); $^{13}$C NMR (75 MHz, CDCl$_3$) δ 5.8, 10.0, 64.5, 69.1, 72.4, 74.0, 79.2, 86.7, 87.4, 123.7, 127.6, 127.7, 128.0, 128.1, 128.5, 128.7, 129.0, 132.9, 133.6, 137.4, 137.4, 141.1, 149.6, 151.0, 152.8, 164.8; IR (KBr): 3062, 2929, 1610, 1580, 1454, 1248, 1048, 1030, 700 cm$^{-1}$; $[α]_D^{23}$ −5.4 (c 1.00, CHCl$_3$). |

(7) Synthesis of Compound 30

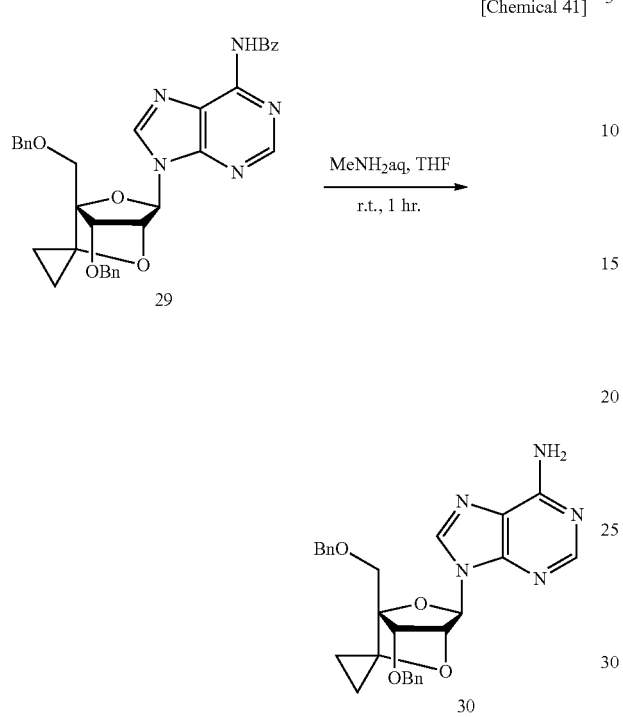

[Chemical 41]

To a solution of compound 29 (60 mg, 0.102 mmol) in tetrahydrofuran (1 mL) was added an aqueous solution of methylamine (40 wt %, 0.42 mL, 5.09 mmol), and the mixture was stirred at room temperature for 1 hour. After completion of the reaction, the solvent was distilled away under reduced pressure. The resultant crude product was purified by silica-gel column chromatography (ethyl acetate:hexane=3:1 (v/v)) to afford compound 30 (41 mg, 83%) as a white foamy solid.

Table 29 shows the physical property data of the obtained compound 30.

TABLE 29

Physical property data of the obtained compound 30

$^1$H NMR (300 MHz, CDCl$_3$) δ 0.71-0.78 (m, 1H), 0.85-1.04 (m, 3H), 3.56 (d, J = 11.1 Hz, 1H), 3.66 (d, J = 11.1 Hz, 1H), 4.36 (s, 1H), 4.57(s, 2H), 4.57 (d, J = 11.7 Hz, 1H), 4.66 (d, J = 12.0 Hz, 1H), 4.80 (s, 1H), 5.58 (s, 2H), 6.15 (s, 1H), 7.23-7.39 (m, 10H), 8.00 (s, 1H), 8.33 (s, 1H); $^{13}$C NMR (75 MHz, CDCl$_3$) δ 5.8, 9.9, 64.7, 69.0, 72.3, 73.9, 79.2, 86.5, 87.1, 120.1, 127.6, 127.7, 128.0, 128.5, 128.6, 137.4, 137.5, 138.4, 149.0, 153.2, 155.7; IR (KBr): 3317, 3149, 3031, 2871, 1651, 1599, 1471, 1298, 1041, 739, 698 cm$^{-1}$; [α]$_D^{26}$ −0.3 (c 1.02, CHCl$_3$); HRMS (MALDI) Calculated for C$_{27}$H$_{27}$N$_5$O$_4$Na: 508.1955, Found: 508.1954.

(8) Synthesis of Compound 31

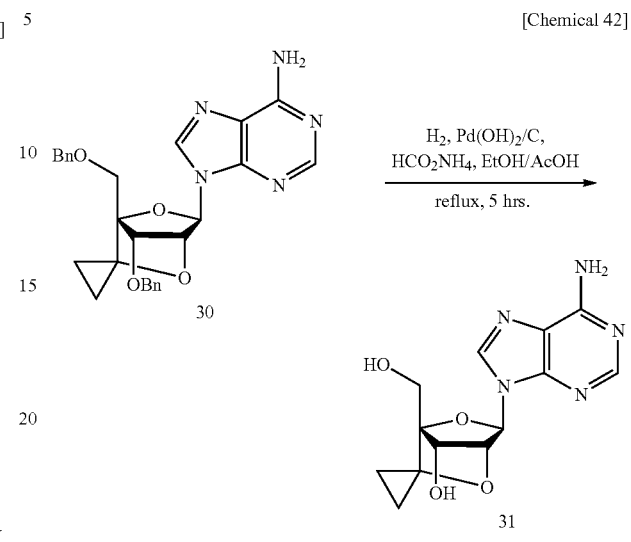

[Chemical 42]

To a solution of compound 30 (450 mg, 0.927 mmol) in ethanol-acetic acid (30.9 mL, 100:3 (v/v)) were added 20% palladium hydroxide/carbon (palladium 20%, 198 mg) and ammonium formate (3.5 g, 55.6 mmmol), and the mixture was heated at reflux for 5 hours. After the reaction solution was filtered through a pleated filter paper, the solvent was distilled away under reduced pressure. The resultant crude product was purified by silica-gel column chromatography (chloroform:methanol=10:1 (v/v)) to afford compound 31 (130 mg, 46%) as a white foamy solid.

Table 30 shows the physical property data of the obtained compound 31.

TABLE 30

Physical property data of the obtained compound 31

$^1$H NMR (300 MHz, CD$_3$OD) δ 0.69-1.00 (m, 4H), 3.63 (d, J = 12.6 Hz, 1H), 3.80 (d, J = 12.6 Hz, 1H), 4.49 (s, 1H), 5.57 (s, 1 H), 6.10 (s, 1H), 8.00 (s, 1H), 8.33 (s, 1H); $^{13}$C NMR (75 MHz, CD$_3$OD) δ 5.5, 10.0, 57.3, 69.1, 73.0, 81.2, 87.3, 89.6, 120.4, 139.8, 149.6, 153.9, 157.3; HRMS (MALDI) Calculated for C$_{13}$H$_{16}$N$_5$O$_4$: 306.1197, Found: 306.1197.

(9) Synthesis of Compound 32

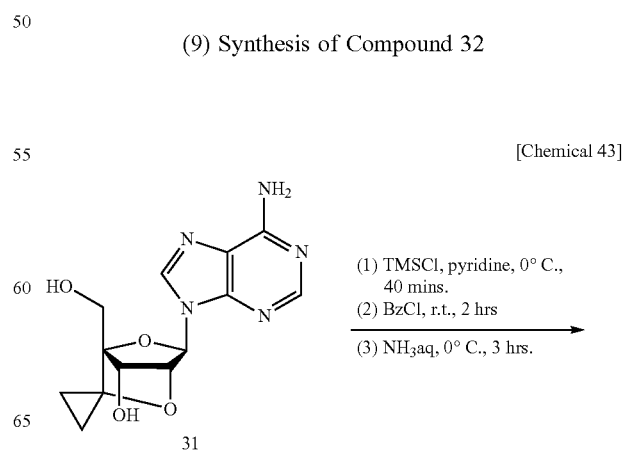

[Chemical 43]

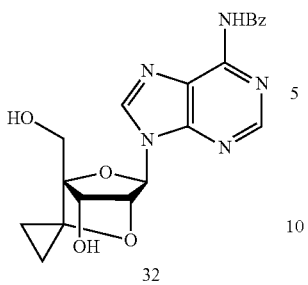

32

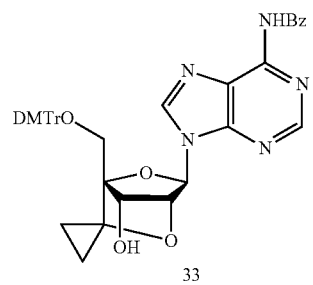

33

Under nitrogen stream, to a solution of compound 31 (81.0 mg, 0.265 mmol) in anhydrous pyridine (2 mL) was added chlorotrimethylsilane (67.0 µL, 0.531 mmol), and the mixture was stirred at 0° C. for 40 minutes. Then, benzoyl chloride (92.0 µL, 0.795 mmol) was added, and the mixture was stirred at room temperature for 2 hours. Furthermore, an aqueous solution of ammonia (28 wt %, 1.2 mL, 18.6 mmol) was added, and the mixture was stirred at 0° C. for 3 hours. The reaction solution was distilled away under reduced pressure, and the resultant crude product was purified by silica-gel column chromatography (chloroform:methanol=30:1 (v/v)→10:1 (v/v)) to afford compound 32 (66 mg, 61%) as a white foamy solid.

Table 31 shows the physical property data of the obtained compound 32.

TABLE 31

Physical property data of the obtained compound 32

$^1$H NMR (300 MHz, CD$_3$OD) δ 0.80-0.97 (m, 4H), 3.65 (d, J = 12.6 Hz, 1H), 3.81 (d, J = 12.6 Hz, 1H), 4.51 (s, 1H), 4.68 (s, 1 H), 6.23 (s, 1H), 7.55-7.69 (m, 3H), 8.09 (d, J = 7.2 Hz, 2H), 8.60 (s, 1H), 8.73 (s, 1H); $^{13}$C NMR (75 MHz, CD$_3$OD) δ 5.5, 10.1, 57.3, 69.2, 73.1, 81.1, 87.6, 89.8, 125.4, 129.5, 129.8, 133.9, 134.9, 143.1, 151.1, 152.5, 153.3, 168.1; IR (KBr): 3321, 1615, 1458, 1259, 1043 cm$^{-1}$; [α]$_D^{25}$ −48.1 (c 0.34, CH$_3$OH); HRMS (MALDI) Calculated for C$_{20}$H$_{19}$N$_5$O$_5$Na: 432.1278, Found: 432.1280.

Under nitrogen stream, to a solution of compound 32 (16 mg, 39.0 µmol) in anhydrous pyridine (0.5 mL) was added 4,4'-dimethoxychloride (19.9 mg, 59.0 µmol), and the mixture was stirred at room temperature for 15 hours. After that, 4,4'-dimethoxychloride (23 mg, 67.9 µmol) was added, and the mixture was stirred at room temperature for 4 hours. Furthermore, 4,4'-dimethoxychloride (223 mg, 0.18 mmol) was added, and the mixture was stirred at room temperature for 1 hour. Then, a saturated aqueous solution of sodium bicarbonate was added, followed by extraction with ethyl acetate and then washing with saturated saline and water. After drying over anhydrous sodium sulfate, the solvent was distilled away under reduced pressure. The resultant crude product was purified by silica-gel column chromatography (ethyl acetate:hexane=1:1 (v/v)) to afford compound 33 (20 mg, 72%) as a white foamy solid.

Table 32 shows the physical property data of the obtained compound 33.

TABLE 32

Physical property data of the obtained compound 33

$^1$H NMR (300 HMz, CDCl3) δ 0.57-0.65 (m, 1H), 0.89-1.02 (m, 3H), 2.60 (s, 1H), 3.23 (d, J = 10.8 Hz, 1H), 3.49 (d, J = 10.8 Hz, 1H), 3.79 (s, 6H), 4.49 (s, 1H), 4.72 (s, 1H), 6.28 (s, 1H), 6.84 (d, J = 9.0 Hz, 4H), 7.20-7.64 (m, 12H), 8.03 (d, J = 7.2 Hz, 1H), 8.31 (s, 1H), 8.79 (s, 1H), 9.10 (s, 1H); $^{13}$C NMR (75 MHz, CDCl$_3$) δ 5.8, 9.7, 55.4, 59.0, 68.5, 74.2, 79.8, 86.2, 86.9, 87.5, 113.4, 113.4, 123.7, 127.2, 128.0, 128.1, 128.2, 129.0, 130.0, 130.1, 133.0, 133.6, 135.1, 135.5, 140.6, 144.3, 149.6, 151.0, 152.9, 158.7, 158.7, 164.8; IR (KBr): 3271, 3058, 3004, 2836, 1609, 1509, 1455, 1251, 1033, 751 cm$^{-1}$; [α]$_D^{24}$ −44.4 (c 1.00, CHCl$_3$); HRMS (MALDI) Calculated for C$_{41}$H$_{37}$N$_5$O$_7$Na: 734.2585, Found: 734.2581.

(10) Synthesis of Compound 33

[Chemical 44]

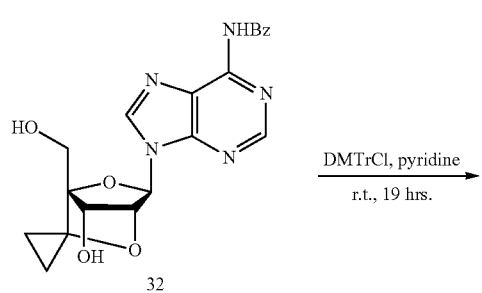

(11) Synthesis of Compound 34

[Chemical 45]

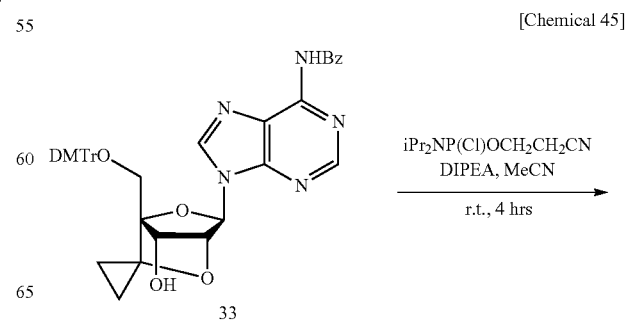

59
-continued

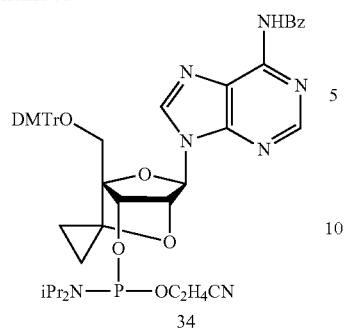
34

Under nitrogen stream, to a solution of compound 33 (52 mg, 73.1 μmol) in anhydrous acetonitrile (1 mL) were added N,N-diisopropylethylamine (38 μL, 21.9 μmol) and 2-cyanoethyl-N,N-diisopropyl phosphorochloridate (24 μL, 11.0 μmol), and the mixture was stirred at room temperature for 2 hours. After that, N,N-diisopropylethylamine (76 μL, 43.8 μmol) and 2-cyanoethyl-N,N-diisopropyl phosphorochloridate (24 μL, 11.0 μmol) were added, and the mixture was stirred at room temperature for 1 hour. Furthermore, 2-cyanoethyl-N,N-diisopropyl phosphorochloridate (24 μL, 11.0 μmol) was added, and the mixture was stirred at room temperature for 1 hour. A saturated aqueous solution of sodium bicarbonate was added, followed by extraction with ethyl acetate and then washing with saturated saline and water. After drying over anhydrous sodium sulfate, the solvent was distilled away under reduced pressure. The resultant crude product was purified by silica-gel column chromatography (0.5% triethylamine-containing ethyl acetate:hexane=2:1 (v/v)) to afford compound 34 (45 mg, 67%: scpBNA-A amidite block) as a white foamy solid.

Table 33 shows the physical property data of the obtained compound 34.

TABLE 33

Physical property data of the obtained compound 34

$^1$H NMR (300 HMz, CDCl3) δ 0.41-0.54 (m, 1H), 0.80-1.03 (m, 3 H), 0.90 (d, J = 6.9 Hz, 3H), 0.97 (d, J = 6.6 Hz, 3H), 1.07 (d, J = 6.3 Hz, 3H), 1.10 (d, J = 6.6 Hz, 3H), 3.18 (m, 1H), 3.42-3.75 (m, 6H), 3.79 (s, 3H), 3.80 (s, 3H), 4.53 (d, J = 6.9 Hz, 1/2H), 4.56 (d, J = 8.7 Hz, 1/2H), 4.91 (s, 1/2H), 4.92 (s, 1/2H), 6.30 (s, 1/2H), 6.30 (s, 1/2H), 6.82-6.86 (m, 4H), 7.19-7.37 (m, 7H), 7.45-7.48 (m, 2H), 7.52-7.65 (m, 3H), 8.04 (d, J = 7.2 Hz, 2H), 8.37(s, 1/2H), 8.40 (s, 1/2H), 8.81 (s, 1/2H), 8.82 (s, 1/2H), 8.98 (s, 1H); $^{31}$P NMR (121.7 MHz, CDCl$_3$) δ 148.8, 148.9; HRMS (MALDI) Calculated for C$_{50}$H$_{54}$N$_7$O$_8$NaP: 934.3664, Found: 934.3657.

Example 10

Synthesis of 2',4'-Bridged Nucleoside (4): Synthesis of Spirocyclopropane BNA-G (scpBNA-G) Amidite Block

[Chemical 46]

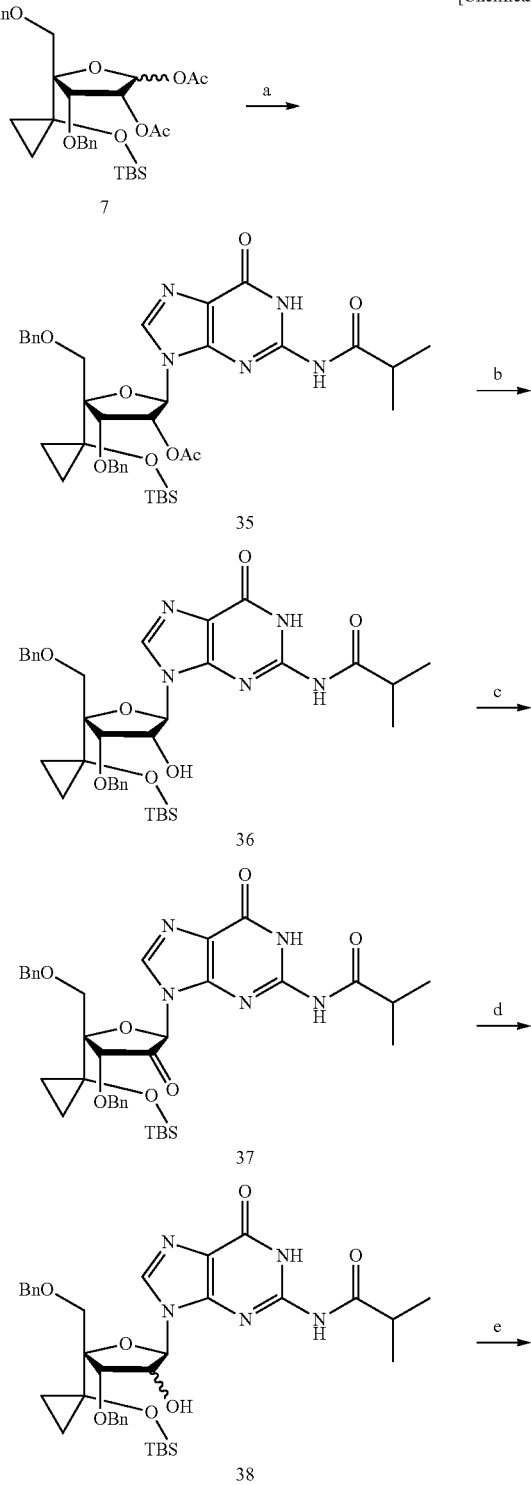

-continued

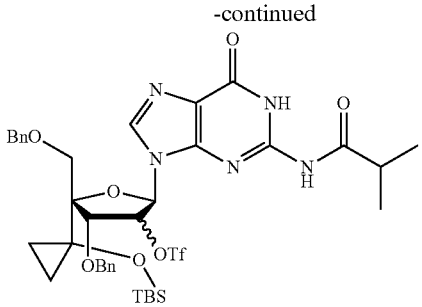
39

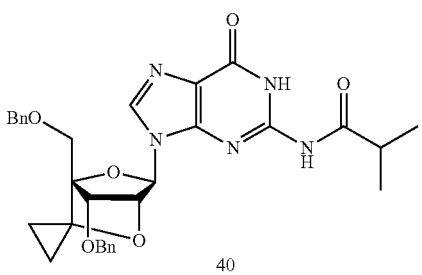
40

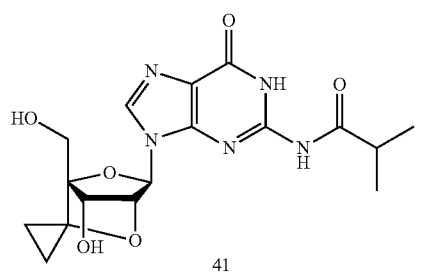
41

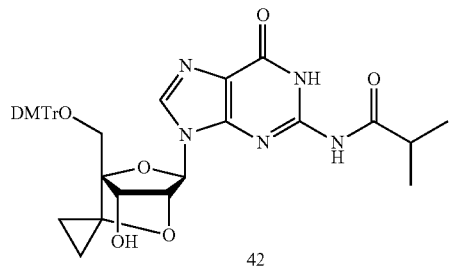
42

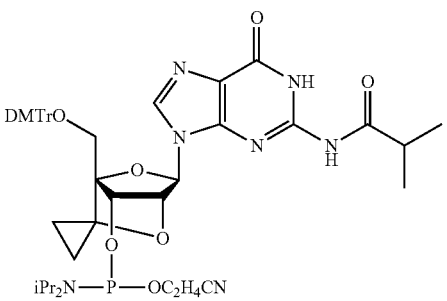
43

(1) Synthesis of Compound 35

[Chemical 47]

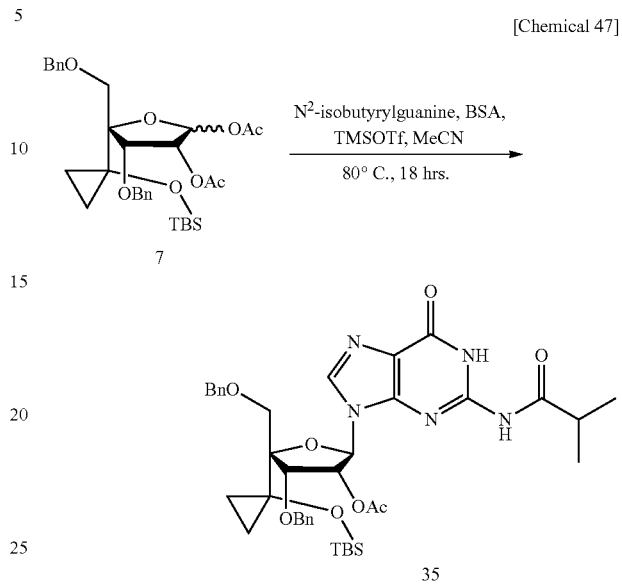

Under nitrogen stream, to a solution of compound 7 (77 mg, 0.132 mmol) obtained in Example 1 in anhydrous acetonitrile (1.5 mL) were added $N^2$-isobutyrylguanine (41 mg, 0.184 mmol) and N,O-bis(trimethylsilyl)acetamide (97.0 μL, 0.395 mmol) at 80° C., and the mixture was stirred for 20 minutes. Then, trimethylsilyl trifluoromethanesulfonate (48.0 μL, 0.263 mmol) was added at 0° C., and the mixture was stirred at 80° C. for 18 hours. After completion of the reaction, a saturated aqueous solution of sodium bicarbonate was added at 0° C., followed by extraction with ethyl acetate and then washing with water and saturated saline. After drying over anhydrous sodium sulfate, the solvent was distilled away under reduced pressure. The resultant crude product was purified by silica-gel column chromatography (ethyl acetate:hexane:methanol=2:10:1 (v/v/v)) to afford compound 35 (48 mg, 49%) as a white foamy solid.

Table 34 shows the physical property data of the obtained compound 35.

TABLE 34

Physical property data of the obtained compound 35

$^1$H NMR (500 MHz, CDCl$_3$) δ 0.00 (s, 3H), 0.01 (s, 3H), 0.63-0.79 (m, 12H), 0.99-1.03 (m, 1H), 1.27 (d, J = 7.0 Hz, 6H), 1.93 (s, 3H), 2.53-2.56 (m, 1H), 3.53 (d, J = 10.0 Hz, 1H), 3.98 (d, J = 9.5 Hz, 1H), 4.45 (d, J = 10.5 Hz, 1H), 4.54 (d, J = 11.5 Hz, 1H), 4.54 (d, J = 4.5 Hz, 1H), 4.80 (d, J = 12.0 Hz, 1H), 5.00 (d, J = 10.5 Hz, 1H), 5.82 (dd, J = 4.5, 8.5 Hz, 1H), 6.00 (d, J = 8.5 Hz, 1H), 7.31-7.45 (m, 10H), 7.97 (s, 1H), 8.02 (s, 1 H), 11.9 (s, 1H); $^{13}$C NMR (126 MHz, CDCl$_3$) δ −3.4, −3.0, 7.2, 10.6, 18.0, 19.1, 20.7, 25.8, 36.7, 58.0, 73.7, 74.0, 75.3, 77.0, 81.1, 84.2, 88.5, 121.0, 127.7, 128.3, 128.4, 128.4, 128.9, 137.1, 137.5, 138.7, 147.4, 148.8, 155.6, 170.2, 178.0; HRMS (MALDI) Calculated for $C_{39}H_{51}N_5O_8NaS$: 768.3399, Found: 768.3398.

(2) Synthesis of Compound 36

(3) Synthesis of Compound 37

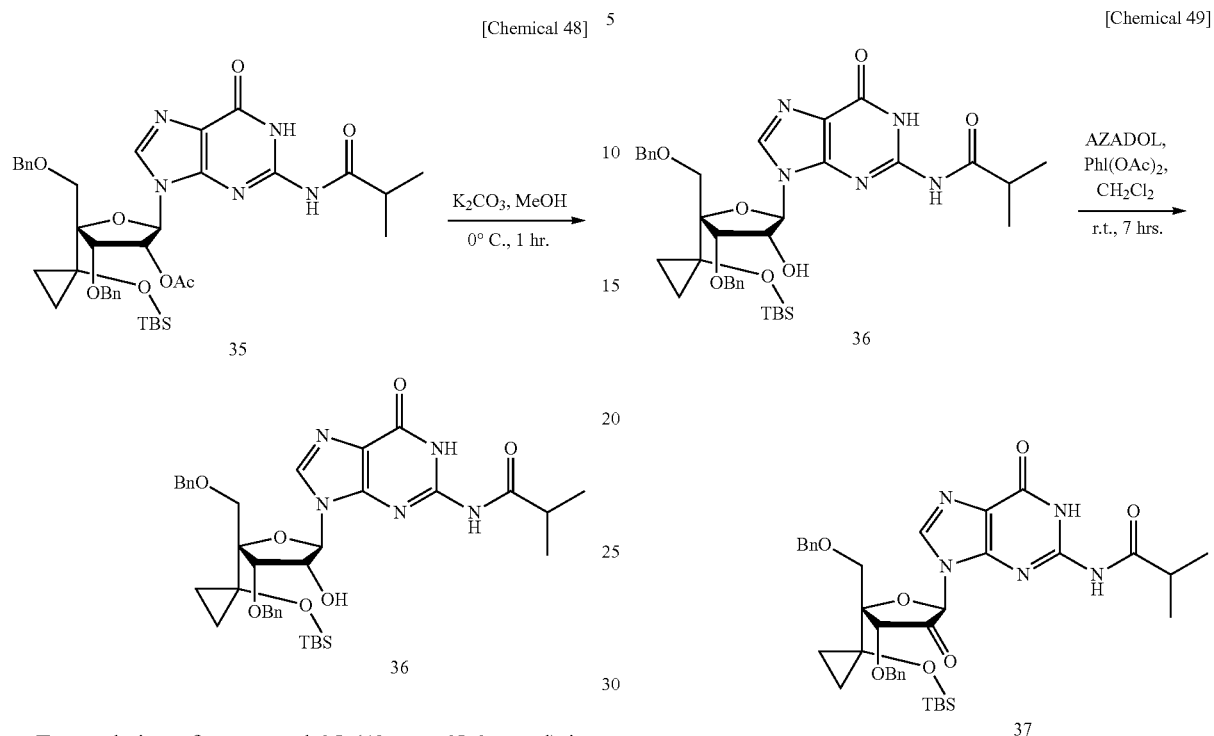

[Chemical 48]

[Chemical 49]

To a solution of compound 35 (48 mg, 65.6 mmol) in methanol (1.5 mL) was added potassium carbonate (27 mg, 0.197 mmol), and the mixture was stirred at 0° C. for 1 hour. After completion of the reaction, water was added at 0° C., followed by extraction with ethyl acetate and then washing with water and saturated saline. After drying over anhydrous sodium sulfate, the solvent was distilled away under reduced pressure. The resultant crude product was purified by silica-gel column chromatography (ethyl acetate:hexane=2:1 (v/v)) to afford compound 36 (44 mg, 95%) as a white foamy solid.

Table 35 shows the physical property data of the obtained compound 36.

TABLE 35

| Physical property data of the obtained compound 36 |
|---|
| $^1$H NMR (300 MHz, CDCl$_3$) δ 0.00 (s, 3H), 0.03 (s, 3H), 0.68-1.02 (m, 12H), 1.23 (d, J = 2.1 Hz, 3H), 1.26 (d, J = 2.1 Hz, 3H), 2.50-2.55 (m, 1H), 3.03 (d, J = 11.4 Hz, 1H), 3.52 (d, J = 9.6 Hz, 1H), 3.98 (d, J = 9.6 Hz, 1H), 4.24 (d, J = 5.1 Hz, 1H), 4.49 (d, J = 11.4 Hz, 1H), 4.56 (d, J = 10.8 Hz, 1H), 4.77 (d, J = 11.7 Hz, 1H), 4.86 (m, 1H), 5.22 (d, J = 10.2 Hz, 1H), 5.57 (d, J = 7.8 Hz, 1H), 7.31-7.43 (m, 10H), 8.00 (s, 1H), 8.05 (s, 1H), 11.9 (s, 1H); $^{13}$C NMR (126 MHz, CDCl$_3$) δ −3.3, −2.9, 7.4, 10.7, 18.0, 18.9, 19.1, 25.8, 36.6, 58.0, 74.0, 74.1, 75.9, 76.9, 83.2, 87.9, 88.3, 121.0, 128.1, 128.3, 128.5, 128.6, 128.9, 137.1, 137.3, 138.0, 147.4, 148.5, 155.7, 178.2; HRMS (MALDI) Calculated for C$_{37}$H$_{49}$N$_5$O$_7$NaSi: 726.3294, Found: 768.3293. |

To a solution of compound 36 (6.5 g, 9.23 mmol) in dichloromethane (100 mL) were added diacetoxyiodobenzene (4.46 g, 13.8 mmol) and 2-hydroxy-2-azaadamantane (71 mg, 0.462 mmol, 5 mol %), and the mixture was stirred at room temperature for 7 hours. After completion of the reaction, a saturated aqueous solution of sodium thiosulfate and a saturated aqueous solution of sodium bicarbonate were added, followed by extraction with ethyl acetate and then washing with water and saturated saline. After drying over anhydrous sodium sulfate, the solvent was distilled away under reduced pressure to afford compound 37 (7.0 g) as a yellow foamy solid. Compound 37 was immediately used for the next reaction without purification.

(4) Synthesis of Compound 38

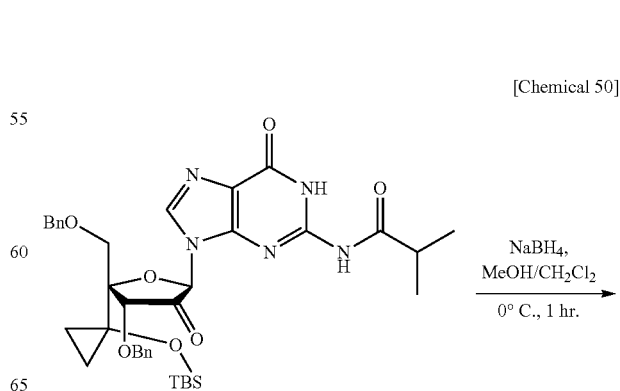

[Chemical 50]

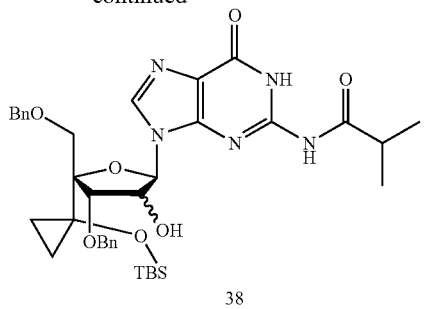

38

To a solution of compound 37 (7.0 g) in methanol-dichloromethane (90 mL, 1:2 (v/v)) was added sodium borohydride (489 mg, 12.9 mmol), and the mixture was stirred at 0° C. for 1 hour. After completion of the reaction, a saturated aqueous ammonium chloride solution was added, followed by extraction with ethyl acetate and then washing with saturated saline and water. After drying over anhydrous sodium sulfate, the solvent was distilled away under reduced pressure. The resultant crude product was purified by silica-gel column chromatography (chloroform:methanol=30:1 (v/v)) to afford compound 38 (5.2 g, 80%, 2 steps, R:S=2:1) as a yellow foamy solid. The obtained compound 38 was a mixture from which it was difficult to separate diastereomers, and thus the mixture was used for the next reaction as is.

(5) Synthesis of Compound 39

[Chemical 51]

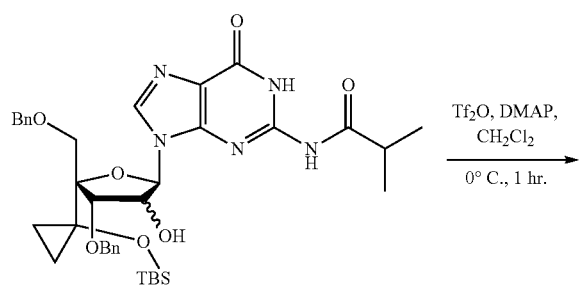

Under nitrogen stream, to a solution of compound 38 (300 mg, 0.43 mmol) in anhydrous dichloromethane (5 mL) were added 4-dimethylaminopyridine (156 mg, 1.28 mmol) and trifluoromethanesulfonic anhydride (90 μL, 0.55 mmol), and the mixture was stirred at 0° C. for 1 hour. After completion of the reaction, a saturated aqueous solution of sodium bicarbonate was added, followed by extraction with ethyl acetate and then washing with water and saturated saline. After drying over anhydrous sodium sulfate, the solvent was distilled away under reduced pressure to afford compound 39 (408 mg) as a yellow foamy solid. Compound 39 was immediately used for the next reaction without purification.

(6) Synthesis of Compound 40

[Chemical 52]

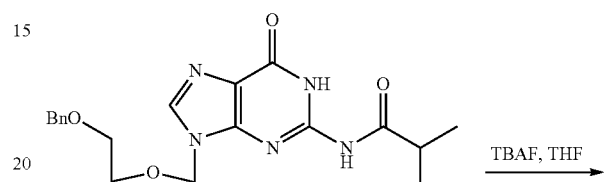

40

To a solution of compound 39 (408 mg) in tetrahydrofuran (4 mL) was added tetrabutylammonium fluoride (1 M tetrahydrofuran solution, 1.28 mL, 1.28 mmol), and the mixture was stirred at room temperature for 30 minutes. After completion of the reaction, the solvent was distilled away under reduced pressure, and the resultant crude product was purified by silica-gel column chromatography (ethyl acetate:hexane:methanol=2:7:1) to afford compound 40 (9 mg, 4% (2 steps)) as a white foamy solid.

Table 36 shows the physical property data of the obtained compound 40.

TABLE 36

Physical property data of the obtained compound 40

$^1$H NMR (300 MHz, CDCl$_3$) δ 0.72-0.97 (m, 12H), 1.27 (d, J = 0.9 Hz, 3H), 1.29 (d, J = 1.5 Hz, 3H), 2.57-2.64 (m, 1H), 3.53 (d, J = 11.4 Hz, 1H), 3.63 (d, J = 11.1 Hz, 1H), 3.98 (d, J = 9.6 Hz, 1H), 4.24 (s, 1H), 4.44 (s, 1H), 4.53-4.63 (m, 4H), 5.92 (s, 1H), 7.23-7.40 (m, 10H), 7.82 (s, 1H), 8.27 (s, 1H), 12.0 (s, 1H); HRMS (MALDI) Calculated for C$_{31}$H$_{33}$N$_5$O$_6$Na: 594.2323, Found: 594.2323.

(7) Synthesis of Compound 41

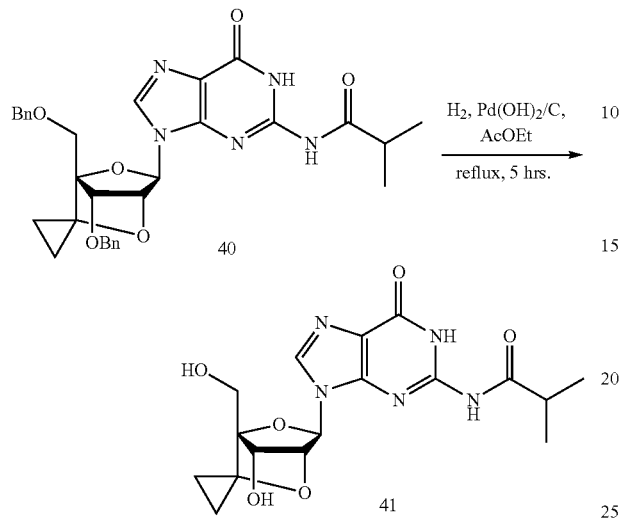

[Chemical 53]

To a solution of compound 40 in ethyl acetate was added 20% palladium hydroxide/carbon (palladium 20%), and the mixture was stirred under hydrogen stream for 5 hours. After the reaction solution was filtered through a pleated filter paper, the solvent was distilled away under reduced pressure. The resultant crude product was purified by silica-gel column chromatography (chloroform:methanol) to afford compound 41 in a suitable yield.

(8) Synthesis of Compound 42

[Chemical 54]

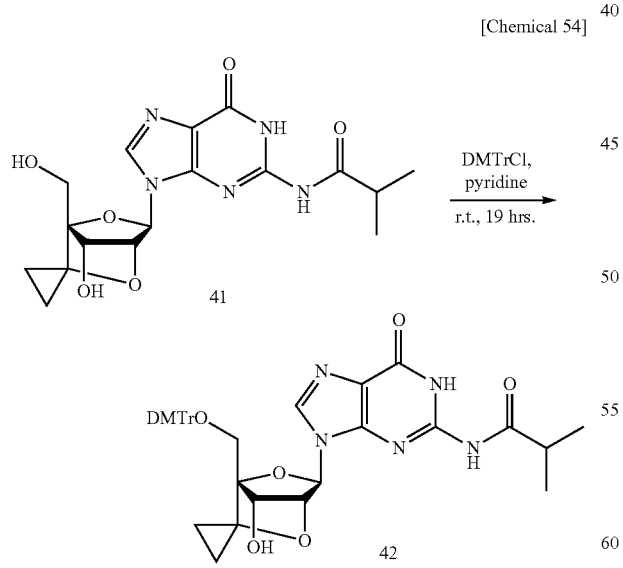

Under nitrogen stream, to a solution of compound 41 in anhydrous pyridine was added 4,4'-dimethoxychloride, and the mixture was stirred at room temperature for 19 hours. A saturated aqueous solution of sodium bicarbonate was added, followed by extraction with ethyl acetate and then washing with saturated saline and water. After drying over anhydrous sodium sulfate, the solvent was distilled away under reduced pressure. The resultant crude product was purified by silica-gel column chromatography (ethyl acetate:hexane) to afford compound 42 in a suitable yield.

(9) Synthesis of Compound 43

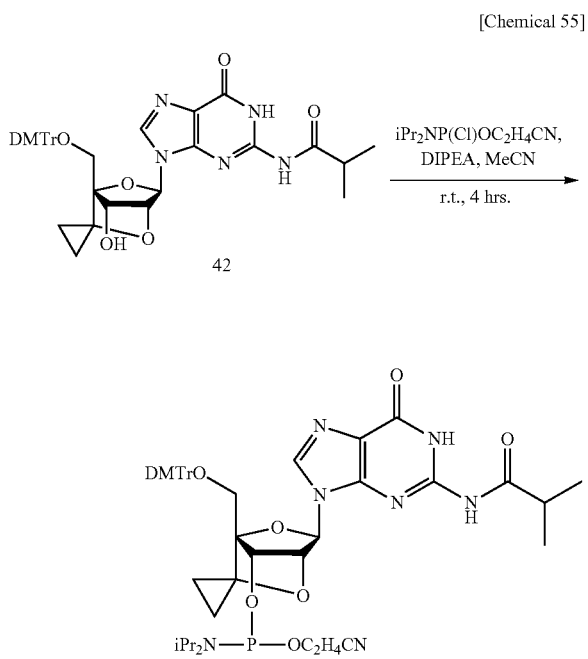

[Chemical 55]

Under nitrogen stream, to a solution of compound 42 in anhydrous acetonitrile were added N,N-diisopropylethylamine and 2-cyanoethyl-N,N-diisopropyl phosphorochloridate, and the mixture was stirred at room temperature for 2 hours. A saturated aqueous solution of sodium bicarbonate was added, followed by extraction with ethyl acetate and then washing with saturated saline and water. After drying over anhydrous sodium sulfate, the solvent was distilled away under reduced pressure. The resultant crude product was purified by silica-gel column chromatography (0.5% triethylamine-containing ethyl acetate:hexane) to afford compound 43 (scpBNA-G amidite block) in a suitable yield.

INDUSTRIAL APPLICABILITY

According to the present invention, novel 2',4'-bridged nucleosides and nucleotides with a spirocyclopropane group at the position 6' are provided. An oligonucleotide containing the 2',4'-bridged artificial nucleotide has a binding affinity for single-stranded RNA comparable to that of known 2',4'-BNA/LNA and higher nuclease resistance than LNA. Oligonucleotides of the present invention are useful as, for example, materials for nucleic acid drugs.

The invention claimed is:

1. A compound represented by formula I below or a salt thereof:

[Chemical 1]

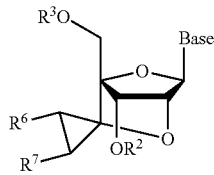

(I)

wherein Base represents a purine-9-yl group or a 2-oxo-1,2-dihydropyrimidine-1-yl group that may have any one or more substituents selected from group α, where the group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio group, an amino group, a $C_1$ to $C_6$ linear alkylamino group, an amino group protected by a protective group for nucleic acid synthesis, and a halogen atom;

$R^2$ and $R^3$ each independently represent a hydrogen atom, a protective group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the group α and that may contain a hetero atom, an aralkyl group having a $C_3$ to $C_{12}$ aryl moiety that may have any one or more substituents selected from the group α and that may contain a hetero atom, an acyl group that may have any one or more substituents selected from the group α, a silyl group that may have any one or more substituents selected from the group α, a phosphate group that may have any one or more substituents selected from the group α, a phosphate group protected by a protective group for nucleic acid synthesis, or —P($R^4$)$R^5$, where $R^4$ and $R^5$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group; and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$—, where n is an integer from 2 to 5.

2. The compound or salt thereof according to claim 1, wherein the Base in the formula I is a 6-aminopurine-9-yl group, a 2,6-diaminopurine-9-yl group, a 2-amino-6-chloropurine-9-yl group, a 2-amino-6-fluoropurine-9-yl group, a 2-amino-6-bromopurine-9-yl group, a 2-amino-6-hydroxypurine-9-yl group, a 6-amino-2-methoxypurine-9-yl group, a 6-amino-2-chloropurine-9-yl group, a 6-amino-2-fluoropurine-9-yl group, a 2,6-dimethoxypurine-9-yl group, a 2,6-dichloropurine-9-yl group, a 6 mercaptopurine-9-yl group, a 2-oxo-4-amino-1,2-dihydropyrimidine-1-yl group, a 4-amino-2-oxo-5-fluoro-1,2-dihydropyrimidine-1-yl group, a 4-amino-2-oxo-5-chloro-1,2-dihydropyrimidine-1-yl group, a 2-oxo-4-methoxy-1,2-dihydropyrimidine-1-yl group, a 2-oxo-4 mercapto-1,2-dihydropyrimidine-1-yl group, a 2-oxo-4-hydroxy-1,2-dihydropyrimidine-1-yl group, a 2-oxo-4-hydroxy-5-methyl-1,2-dihydropyrimidine-1-yl group, or a 4-amino-5-methyl-2-oxo-1,2-dihydropyrimidine-1-yl group.

3. The compound or salt thereof according to claim 2, wherein the Base in the formula I is a 2-oxo-4-hydroxy-5-methyl-1,2-dihydropyrimidine-1-yl group.

4. The compound or salt thereof according to claim 3, wherein $R^6$ and $R^7$ in the formula I are both hydrogen atoms.

5. The compound or salt thereof according to claim 2, wherein $R^6$ and $R^7$ in the formula I are both hydrogen atoms.

6. The compound or salt thereof according to claim 1, wherein the Base in the formula I is a 2-oxo-4-hydroxy-5-methyl-1,2-dihydropyrimidine-1-yl group.

7. The compound or salt thereof according to claim 6, wherein $R^6$ and $R^7$ in the formula I are both hydrogen atoms.

8. The compound or salt thereof according to claim 1, wherein $R^6$ and $R^7$ in the formula I are both hydrogen atoms.

9. An oligonucleotide containing at least one nucleoside structure represented by formula II below or a pharmacologically acceptable salt thereof:

[Chemical 2]

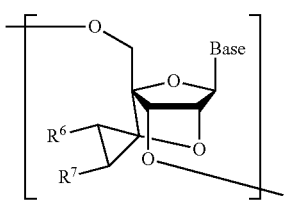

(II)

wherein Base represents a purine-9-yl group or a 2-oxo-1,2-dihydropyrimidine-1-yl group that may have any one or more substituents selected from group α, wherein the group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio groups, an amino group, a $C_1$ to $C_6$ linear alkylamino group, an amino group protected by a protective group for nucleic acid synthesis, and a halogen atom; and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$—, where n is an integer from 2 to 5.

10. The oligonucleotide or pharmacologically acceptable salt thereof according to claim 9, wherein $R^6$ and $R^7$ in the formula II are both hydrogen atoms.

11. A method for producing the oligonucleotide or pharmacologically acceptable salt thereof according to claim 9, comprising:

synthesizing an oligonucleotide using a compound represented by formula I below or a pharmacologically acceptable salt thereof:

[Chemical 3]

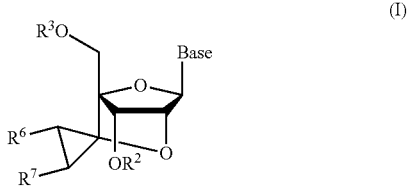

(I)

wherein Base represents a purine-9-yl group or a 2-oxo-1,2-dihydropyrimidine-1-yl group that may have any one or more substituents selected from group α, wherein group α consists of a hydroxyl group, a hydroxyl group protected by a protective group for nucleic acid synthesis, a $C_1$ to $C_6$ linear alkyl group, a $C_1$ to $C_6$ linear alkoxy group, a mercapto group, a mercapto group protected by a protective group for nucleic acid synthesis, a $C_1$ to $C_6$ linear alkylthio group, an amino group, a $C_1$ to $C_6$ linear alkylamino group, an amino group protected by a protective group for nucleic acid synthesis, and a halogen atom;

$R^2$ and $R^3$ each independently represent a hydrogen atom, a protective group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{10}$ aryl group that may have any one or more substituents selected from the group α and that may contain a hetero atom, an aralkyl group having a $C_3$ to $C_{12}$ aryl moiety that may have any one or more substituents selected from the group α and that may contain a hetero atom, an acyl group that may have any one or more substituents selected from the group α, a silyl group that may have any one or more substituents selected from the group α, a phosphate group that may have any one or more substituents selected from the group α, a phosphate group protected by a protective group for nucleic acid synthesis, or —$P(R^4)R^5$, where $R^4$ and $R^5$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group; and $R^6$ and $R^7$ each independently represent a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom; or $R^6$ and $R^7$ are taken together to represent —$(CH_2)_n$—, where n is an integer from 2 to 5.

* * * * *

UNITED STATES PATENT AND TRADEMARK OFFICE
CERTIFICATE OF CORRECTION

PATENT NO. : 9,611,479 B2
APPLICATION NO. : 15/118546
DATED : April 4, 2017
INVENTOR(S) : Satoshi Obika et al.

Page 1 of 1

It is certified that error appears in the above-identified patent and that said Letters Patent is hereby corrected as shown below:

In the Specification

Column 17, Line 16, Reagents and conditions under each step should be added:
Reagents and conditions under each step: (a) DMP, $CH_2Cl_2$, r.t., 40 mins., quantitative.; (b) $H_2O_2$aq., $NaClO_2$, $NaH_2PO_4$aq., MeCN, r.t., 1 hr., 96%; (c) MeI, $NaHCO_3$, DMF, r.t., 20 hrs., 93%; (d) EtMgBr, $Ti(O^iPr)_4$, THF, r.t., 18 hrs., 89%; (e) TBSOTf, 2, 6-lutidine, $CH_2Cl_2$, r.t., 2 hrs., 90%; (f) $Ac_2O$, TFA, AcOH, r.t., 5 hrs.; (g) tymine, BSA, TMSOTf, MeCN, 80 °C, 2 hrs.; (h) $MeNH_2$, THF, r.t., 4 hrs.; (i) MsCl, pyridine, r.t., 4 hrs., 72% (4 steps); (j) NaOHaq., THF-EtOH, 70 °C, 8 hrs.; ($j_2$) TBAF, THF, r.t., 5 hrs., 91%; ($j_3$) $K_2CO_3$, DMF, 90 °C, 20 hrs., 77%; (k) $Tf_2O$, pyridine, r.t., 14 hrs.; (l) TBAF, THF, r.t., 2 hrs., 32% (3 steps); (m) $H_2$, $Pd(OH)_2/C$, EtOH, r.t., 2 hrs.; (n) DMTrCl, pyridine, r.t., 14 hrs., 60% (2 steps); (o) $^iPr_2NP(Cl)OC_2H_4CN$, DIPEA, MeCN, r.t., 2 hrs., 60%.

Column 42, Line 61, the portion of the formula reading
"$iPr_2NP(Cl)OCH_2CH_2$" should read
-- $iPr_2NP(Cl)OCH_2CH_2CN$ --

Column 61, Line 66, Reagents and conditions under each step should be added:
Reagents and conditions under each step: (a) $N^2$-isobutyrylguanine, BSA, TMSOTf, MeCN, 80 °C, 18 hrs., 49%; (b) $K_2CO_3$, MeOH, 0 °C, 1 hr., 95%; (c) AZADOL, PhI(OAc)$_2$, $CH_2Cl_2$, r.t., 7 hrs; (d) $NaBH_4$, $MeOH/CH_2Cl_2$, 0 °C, 1 hr., 80% (2 steps, $R:S$ = 2:1); (e) $Tf_2O$, DMAP, $CH_2Cl_2$, 0 °C, 1 hr.; (f) TBAF, THF, r.t., 30 mins., 4% (2 steps); (g) $H_2$, $Pd(OH)_2/C$, AcOEt, reflux, 5 hrs.; (h) DMTrCl, pyridine, r.t., 19 hrs.; (i) $iPr_2NP(Cl)OC_2H_4CN$, DIPEA, MeCN, r.t., 4 hrs.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Target strand

<400> SEQUENCE: 1
agcaaaaaac gc                                                          12

<210> SEQ ID NO 2
<211> LENGTH: 14
<212> TYPE: RNA
<213> ORGANISM: Artificial Sequence
<220> FEATURE:
<223> OTHER INFORMATION: fragment of nt 60 to 73 from mouse Pten mRNA

<400> SEQUENCE: 2
agcugcagcc auga                                                        14
```